US009835851B2

(12) United States Patent
Funakubo et al.

(10) Patent No.: US 9,835,851 B2
(45) Date of Patent: Dec. 5, 2017

(54) OPTICAL FIBER SCANNER

(71) Applicant: OLYMPUS CORPORATION, Tokyo (JP)

(72) Inventors: Tomoki Funakubo, Nagano (JP); Hiroshi Tsuruta, Sagamihara (JP); Morimichi Shimizu, Hachioji (JP); Yasuaki Kasai, Saitama (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/676,128

(22) Filed: Apr. 1, 2015

(65) Prior Publication Data
US 2015/0205050 A1 Jul. 23, 2015

Related U.S. Application Data

(63) Continuation of application No. PCT/JP2013/076242, filed on Sep. 27, 2013.

(30) Foreign Application Priority Data

Oct. 1, 2012 (JP) ................................. 2012-219640
Jan. 18, 2013 (JP) ................................. 2013-007550

(51) Int. Cl.
*G02B 6/00* (2006.01)
*A61B 1/06* (2006.01)
(Continued)

(52) U.S. Cl.
CPC .......... *G02B 26/101* (2013.01); *G02B 26/103* (2013.01); *H01L 41/083* (2013.01);
(Continued)

(58) Field of Classification Search
CPC .................. A61B 1/00172; A61B 1/0062; G02B 26/101; G02B 26/103; G02B 6/3578;
(Continued)

(56) References Cited

U.S. PATENT DOCUMENTS 5,416,876 A 5/1995 Ansley et al.
5,727,098 A 3/1998 Jacobson
(Continued)

FOREIGN PATENT DOCUMENTS

CN 101923218 A 12/2010
JP S62-119515 A 5/1987
(Continued)

OTHER PUBLICATIONS

"Introduction to piezo transducers", Piezo Systems catalog #8, pp. 22-25 and 62-64, 2011.*
(Continued)

*Primary Examiner* — Robert Tavlykaev
(74) *Attorney, Agent, or Firm* — Scully, Scott, Murphy & Presser, P.C.

(57) ABSTRACT

The force of a piezoelectric element is efficiently transferred to an optical fiber without attenuation, so that the vibration of the optical fiber becomes large. Provided is an optical fiber scanner including an optical fiber which has an elongated cylindrical shape in which illumination light emitted from a light source is guided and can emerge from a distal end thereof and whose distal end can be vibrated in a direction intersecting the longitudinal direction thereof; and at least one piezoelectric element which have a plate shape polarized in a thickness direction thereof and which are separately bonded to an outer circumferential surface of the optical fiber closer to a base side than to a distal end thereof.

11 Claims, 39 Drawing Sheets

(51) Int. Cl.
*A61B 5/00* (2006.01)
*A61B 6/00* (2006.01)
*G02B 26/10* (2006.01)
*H01L 41/083* (2006.01)
*H01L 41/09* (2006.01)
*A61B 1/00* (2006.01)

(52) U.S. Cl.
CPC ...... H01L 41/0913 (2013.01); H01L 41/0966 (2013.01); *A61B 1/00165* (2013.01)

(58) Field of Classification Search
CPC .............. H01L 41/083; H01L 41/0913; H01L 41/0966; H01L 41/0926
USPC ...................... 385/12, 13; 600/182, 342, 478
See application file for complete search history.

(56) References Cited

U.S. PATENT DOCUMENTS

| | | | |
|---|---|---|---|
| 6,222,302 | B1 | 4/2001 | Imada et al. |
| 8,226,551 | B2 | 7/2012 | Sugimoto |
| 8,553,337 | B2* | 10/2013 | Webb ...................... A61B 1/043 359/722 |
| 8,655,431 | B2* | 2/2014 | Joos ....................... A61B 18/20 600/108 |
| 2001/0055462 | A1* | 12/2001 | Seibel ................ A61B 1/00048 385/147 |
| 2002/0064341 | A1* | 5/2002 | Fauver ................... G02B 6/241 385/25 |
| 2010/0261958 | A1 | 10/2010 | Webb et al. |
| 2012/0013576 | A1 | 1/2012 | Chung et al. |
| 2013/0257222 | A1* | 10/2013 | Funakubo ............. H01L 41/047 310/317 |

FOREIGN PATENT DOCUMENTS

| | | |
|---|---|---|
| JP | H11-168246 A | 6/1999 |
| JP | 2003-315702 A | 11/2003 |
| JP | 2008-504557 A | 2/2008 |
| JP | 2008-511039 A | 4/2008 |
| WO | WO 2006/004743 A2 | 1/2006 |
| WO | WO 2006/022557 A1 | 3/2006 |
| WO | WO 2012/073958 A1 | 6/2012 |

OTHER PUBLICATIONS

International Search Report dated Oct. 29, 2013 issued in PCT/JP2013/076242.
Extended Supplementary European Search Report dated May 23, 2016 in related European Application No. 13 84 4203.3.
Japanese Office Action dated Aug. 9, 2016 in related Japanese Patent Application No. 2012-219640.

* cited by examiner

OPTICAL FIBER SCANNER

CROSS-REFERENCE TO RELATED APPLICATIONS

This is a continuation of International Application PCT/JP2013/076242 which is hereby incorporated by reference herein in its entirety.

This application is based on Japanese Patent Application No. 2012-219640 and 2013-007550, the contents of which are incorporated herein by reference.

TECHNICAL FIELD

The present invention relates to an optical fiber scanner.

BACKGROUND ART

In the medical field, there is a known optical fiber scanner in the related art that scans illumination light on a subject by causing illumination light to emerge from an optical fiber while vibrating the optical fiber at high speed using a piezoelectric element (for example, see Patent Literature 1). The optical fiber scanner described in Patent Literature 1 is provided with a tube-shaped piezoelectric element (PZT tube), four electrodes which are arranged on the surface of this PZT tube with equal gaps therebetween in the circumferential direction, and an optical fiber that is inserted inside the PZT tube, and the distal end portion of the optical fiber is fixed to the PZT tube by a coupling member.

In the optical fiber scanner described in Patent Literature 1, when the PZT tube deforms in a bent shape, a force in a perpendicular direction acts on the optical fiber via the coupling member, and this force causes the optical fiber to undergo bending vibrations. Thus, by combining the bending vibrations occurring in two orthogonal directions in the optical fiber, it is possible to make the distal end of the optical fiber vibrate in a spiral fashion and to two-dimensionally scan the illumination light.

CITATION LIST

Patent Literature

{PTL 1} Japanese Translation of PCT International Application, Publication No. 2008-504557

SUMMARY OF INVENTION

Solution to Problem

A first aspect of the present invention is an optical fiber scanner including an elongated optical fiber in which illumination light is guided and can emerge from a distal end thereof; and at least one piezoelectric element having a plate shape polarized in a thickness direction thereof and being individually bonded to an outer circumferential surface of the optical fiber closer to a base side than to the distal end thereof.

DESCRIPTION OF EMBODIMENTS

First Embodiment

An optical fiber scanner 10 according to a first embodiment of the present invention will be described below with reference to the drawings.

Figure 1:
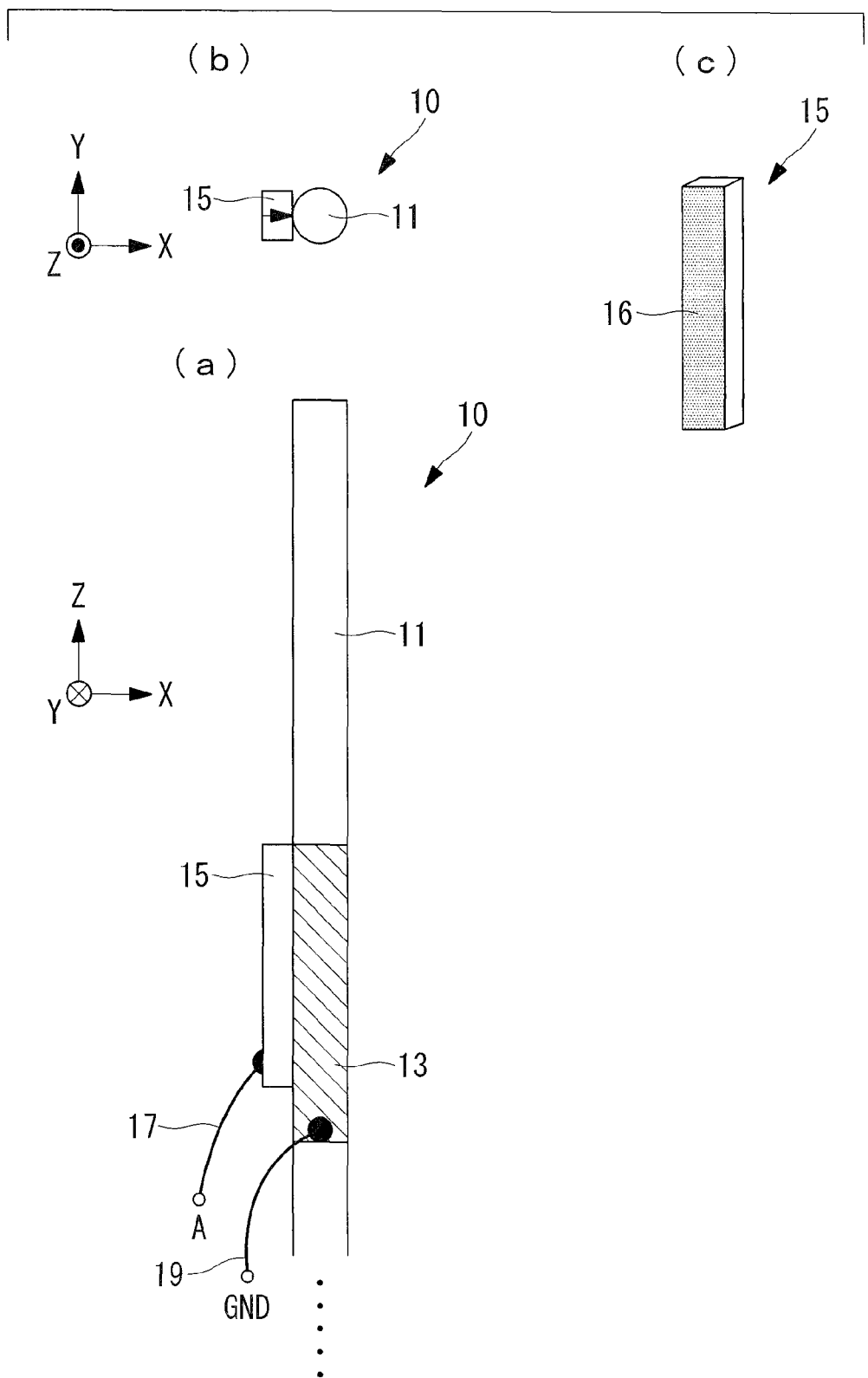
In FIG. 1, (a) is a diagram showing, in outline, the configuration of an optical fiber scanner according to a first embodiment of the present invention, viewed in a direction perpendicular to the longitudinal direction, (b) is a view of (a) in the longitudinal direction from the forward side of the optical fiber, and (c) is a perspective view in which only a piezoelectric element in (a) has been picked out.

As shown in FIGS. 1(a) and (b), the optical fiber scanner 10 according to this embodiment includes an elongated, cylindrical optical fiber 11 made from glass material, a conductive electrode member (hereinafter referred to as conductive electrode) 13 provided on the outer circumferential surface of the optical fiber 11, and a piezoelectric element 15 in the form of a single rectangular plate which is bonded to the outer circumferential surface of the optical fiber 11, with the conductive electrode 13 disposed therebetween.

The optical fiber 11 is configured so as to be able to guide illumination light emitted from a light source (not illustrated) and make the light emerge from the distal end thereof.

As the conductive electrode 13, it is possible to use sputtered metal, conductive silver paste, or a conductive adhesive, etc. The conductive electrode 13 is formed on part of the outer circumferential surface of the optical fiber 11, closer to the base side than to the distal end, and around the entire circumference thereof. This conductive electrode 13 has high hardness and a thickness on the order of several micrometers.

The piezoelectric element 15 is formed of lead zirconate titanate (PZT). Also, as shown in FIG. 1(c), the piezoelectric element 15 has electrodes 16 disposed on the two surfaces that face each other in the thickness direction (hereinafter defined as the front surface and the rear surface) and exhibits polarization in the thickness direction in response to a prescribed DC voltage. The polarization vector is defined as being directed from the positive surface (front surface) to the negative surface (rear surface) of the piezoelectric element 15.

The piezoelectric element 15 has its rear surface joined to the conductive electrode 13 with adhesive and is bonded to the outer circumferential surface of the optical fiber 11 over the entire length of the piezoelectric element 15. More specifically, a thin layer of epoxy adhesive is applied to the rear surface of the piezoelectric element 15 and the front surface of the conductive electrode 13, and after the piezoelectric element 15 and the conductive electrode 13 are aligned under a stereomicroscope, the epoxy adhesive is subjected to thermal curing at a prescribed temperature while pressing the piezoelectric element 15 to the conductive electrode 13 by using heat-shrink tubing, thus joining the piezoelectric element 15 to the conductive electrode 13. Joining of the piezoelectric element 15 and the conductive electrode 13 may be performed via a welding technique using solder or the like. By bonding the piezoelectric element 15 over the entire length thereof, expansion and contraction over the entire length of the piezoelectric element 15 can be transferred to the optical fiber 11 without any loss.

A lead wire 17 that constitutes an A-phase for applying an alternating voltage to the piezoelectric element 15 is joined to the front surface of the piezoelectric element 15, in other words, to the surface opposite from the rear surface which is joined to the conductive electrode 13, by using a conductive adhesive. In addition, a common GND line 19 is joined to the conductive electrode 13 by using a conductive adhesive. By electrically connecting the electrode 16 on the rear surface of the piezoelectric element 15 and the conductive electrode 13, it becomes possible to use the conductive electrode 13 as a GND electrode.

The operation of the thus-configured optical fiber scanner 10 will be described below.

To scan illumination light emitted from a light source on a subject with the optical fiber scanner 10 according to this embodiment, first, an alternating voltage corresponding to the frequency of the bending resonance vibration is applied to the A-phase of the piezoelectric element 15 via the lead wire 17.

When the alternating voltage is applied to the piezoelectric element 15 in the thickness direction thereof, the piezoelectric element 15 expands and contracts in a direction perpendicular to the polarization direction, in other words, in a direction perpendicular to the thickness direction. Accordingly, as shown in FIG. 2(a), a bending resonance vibration is excited in the optical fiber 11, so that the distal end vibrates in a direction (X direction) that intersects the longitudinal direction (Z direction).

Figure 2:
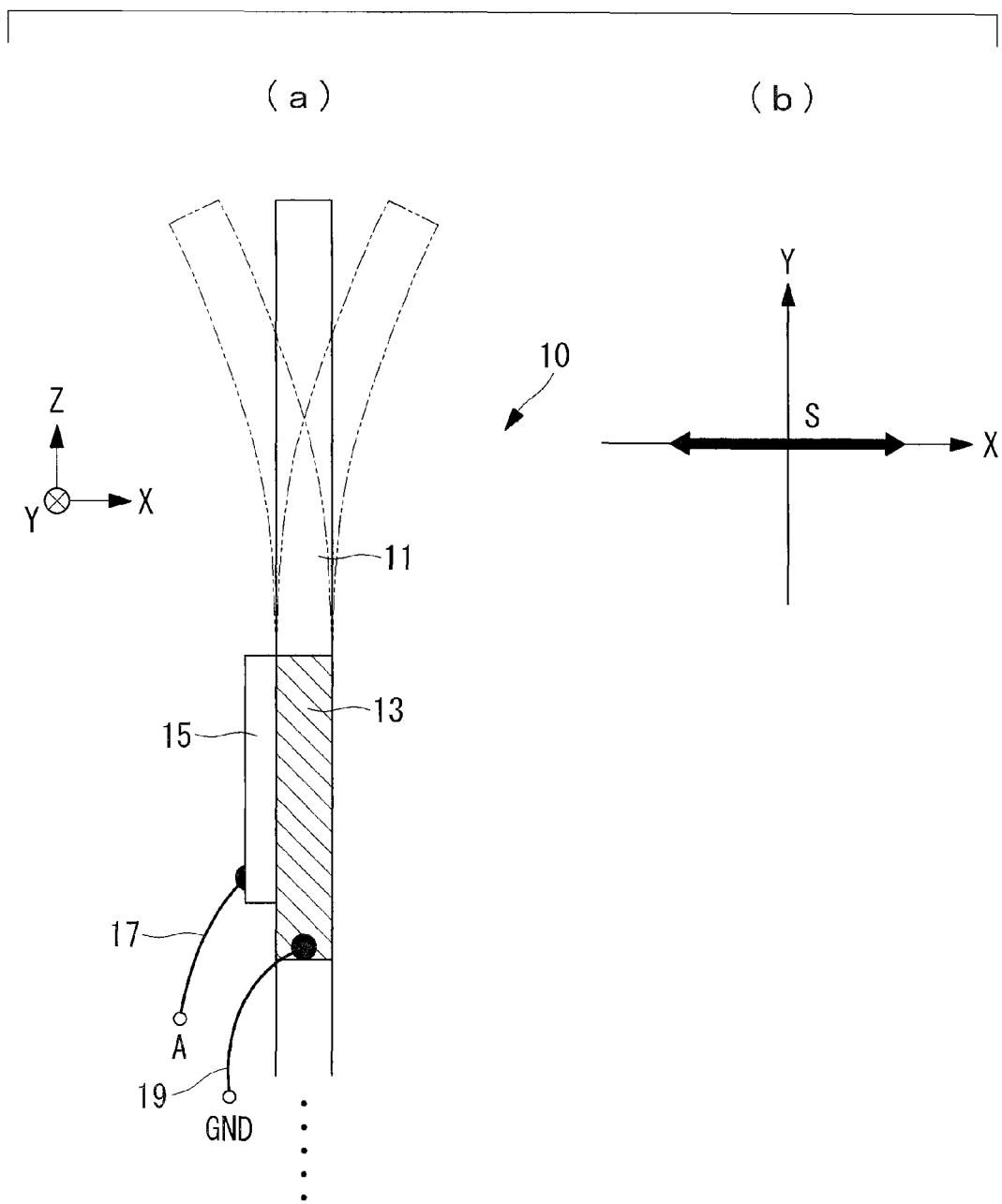
In FIG. 2, (a) is a diagram showing a state in which the distal end of the optical fiber in FIG. 1 is vibrated in the X direction, and (b) is a diagram showing the path traced out by the vibration of the distal end of the optical fiber in (a).

In this state, when the illumination light emitted from the light source is guided in the optical fiber 11 and emerges from the distal end thereof, as shown in FIG. 2(b), the illumination light can be scanned on the subject in a reciprocating manner in the X direction in association with the linear vibration of the distal end of the optical fiber 11. In FIG. 2(b), arrow S shows the path traced out by the distal end of the vibrating optical fiber 11.

In this case, with the optical fiber scanner 10 according to this embodiment, by bonding the piezoelectric element 15 in the form of a single plate to the outer circumferential surface of the optical fiber 11, it is possible to make the piezoelectric element 15 adhere to the outer circumferential surface of the optical fiber 11 with good precision. Accordingly, the expansion and contraction of the piezoelectric element 15 can be transferred to the optical fiber 11 with high efficiency, and the optical fiber 11 can thus be made to undergo a large bending vibration.

In addition, since the conductive electrode 13 has high hardness and a thickness on the order of several micrometers, the force transferred from the piezoelectric element 15 to the optical fiber 11 undergoes almost no attenuation in the conductive electrode 13. Therefore, by directly bonding the piezoelectric element 15 to the outer circumferential surface of the optical fiber 11, with the conductive electrode 13 disposed therebetween, attenuation of the force, as in the case where a resin material exists between the optical fiber 11 and the piezoelectric element 15, can be avoided, and the bending vibration of the optical fiber 11 can thus be made larger.

Furthermore, by providing the conductive electrode 13 between the optical fiber 11 and the piezoelectric element 15, it is not necessary to extend the common GND line 19 from the electrode 16 on the rear surface of the piezoelectric element 15, which is joined to the optical fiber 11; instead, the common GND line 19 can be extended from any position on the conductive electrode 13. Therefore, routing of the lead wire 17 and the common GND line 19 can be simplified.

This embodiment can be modified in the following way.

Figure 3:
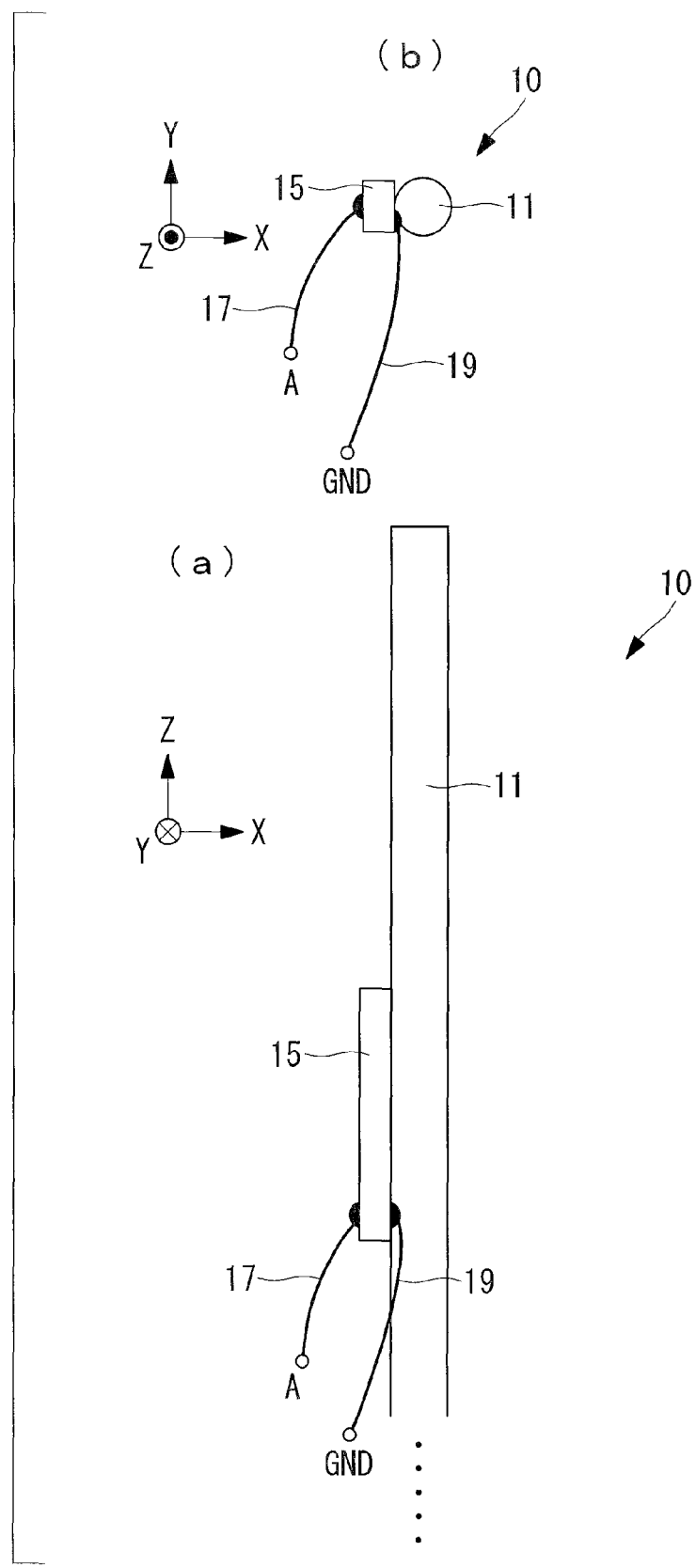
In FIG. 3, (a) is diagram showing, in outline, the configuration of an optical fiber scanner according to a first modification of the first embodiment of the present invention, viewed in a direction perpendicular to the longitudinal direction, and (b) is a view of the optical fiber in (a) in the longitudinal direction from the forward side thereof.

As a first modification, instead of disposing the conductive electrode 13 between the optical fiber 11 and the piezoelectric element 15, as shown in FIGS. 3(a) and (b), the electrode 16 on the rear surface of the piezoelectric element 15 may be directly joined to the outer circumferential surface of the optical fiber 11. In this case, the common GND line 19 should be joined at a position on the rear surface of the piezoelectric element 15 where the electrode 16 is exposed, by using a conductive adhesive. With this modification, it is possible to directly transfer the force from the piezoelectric element 15 to the optical fiber. Also, it is possible to simplify the structure by virtue of the elimination of the conductive electrode 13.

Second Embodiment

Next, an optical fiber scanner 20 according to a second embodiment of the present invention will be described below with reference to the drawings.

Figure 4:
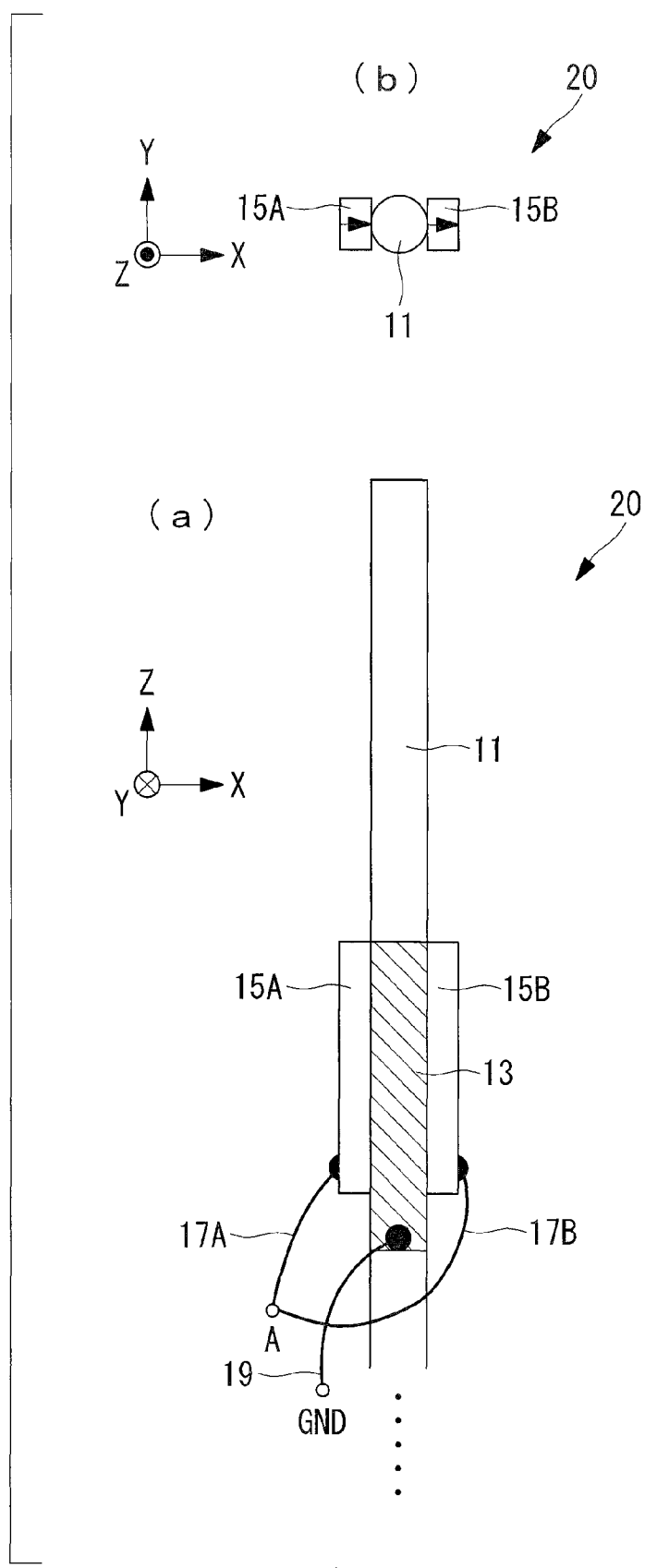
In FIG. 4, (a) is a diagram showing, in outline, the configuration of an optical fiber scanner according to a second embodiment of the present invention, viewed in a direction perpendicular to the longitudinal direction, and (b) is a view of the optical fiber in (a) in the longitudinal direction from the forward side thereof.

As shown in FIGS. 4(a) and (b), the optical fiber scanner 20 according to this embodiment differs from the first embodiment in that a pair of piezoelectric elements 15A and 15B, which are disposed parallel to and opposing each other so as to flank the optical fiber 11, are provided.

In the following, parts having the same configuration as those in the optical fiber scanner 10 according to the first embodiment are assigned the same reference signs, and a description thereof will be omitted.

The pair of piezoelectric elements 15A and 15B are joined to the outer circumferential surface of the optical fiber 11 using adhesives, with the conductive electrode 13 disposed therebetween. More specifically, the piezoelectric element 15A has its rear surface joined to the conductive electrode 13, and the piezoelectric element 15B has its front surface joined to the conductive electrode 13. Therefore, the polarization directions of the piezoelectric element 15A and the piezoelectric element 15B are the same direction as each other.

In addition, on the pair of piezoelectric elements 15A and 15B, lead wires 17A and 17B are joined to the electrodes 16 on the surfaces that are on the opposite sides from the surfaces that are joined to the conductive electrode 13, using conductive adhesive. These two lead wires 17A and 17B are joined together so as to form an A-phase. Also, a single common GND line 19 is joined to the conductive electrode 13 with conductive adhesive.

Figure 5:
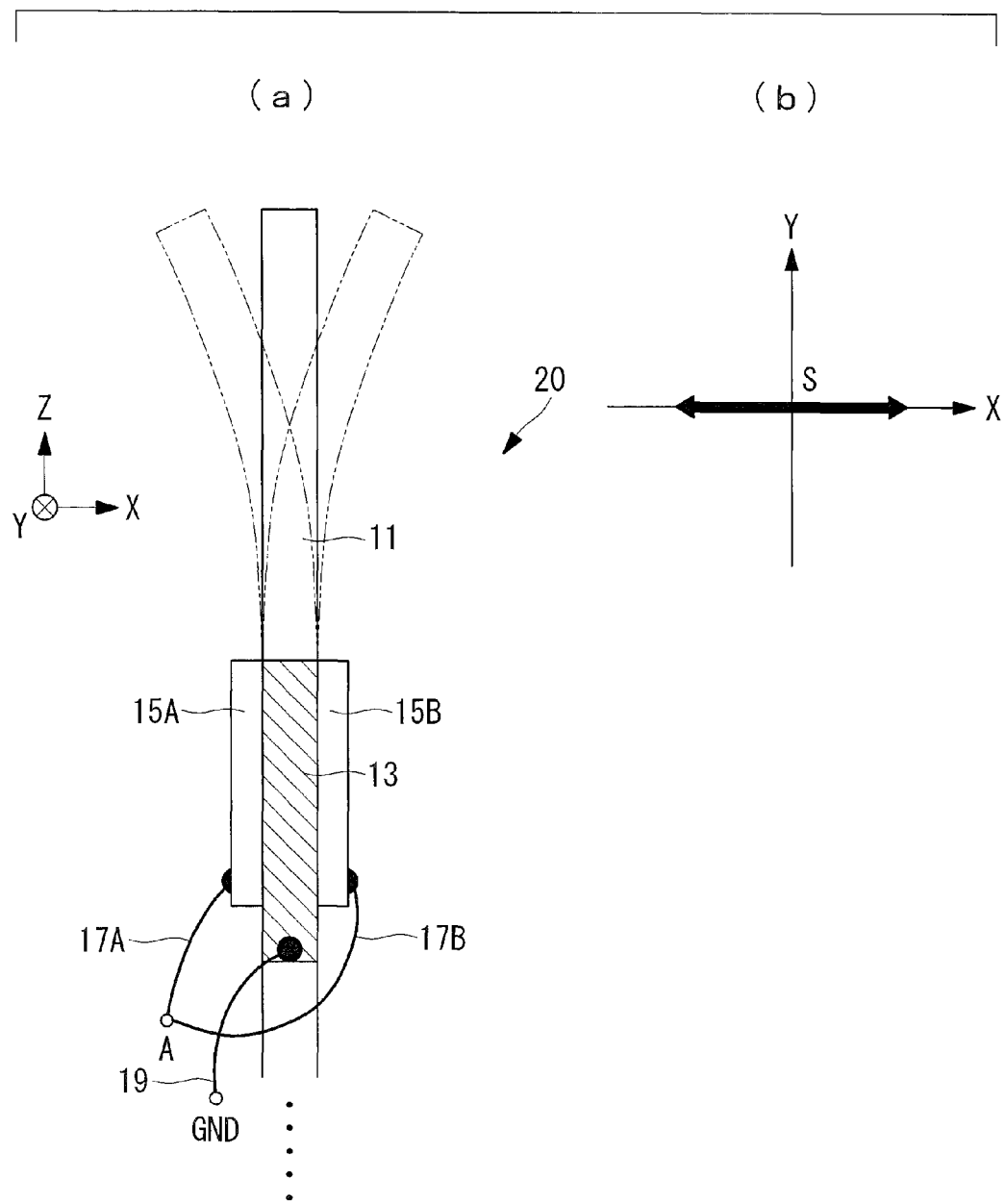
In FIG. 5, (a) is a diagram showing a state in which the distal end of the optical fiber in FIG. 4 is vibrated in the X direction, and (b) is a diagram showing the path traced out by the vibration of the distal end of the optical fiber in (a).

In the optical fiber scanner 20 according to this embodiment, when an alternating voltage corresponding to the frequency of the bending resonance vibration is applied to the A-phase of the pair of piezoelectric elements 15A and 15B via the lead wires 17A and 17B, the piezoelectric elements 15A and 15B together expand and contract in a direction perpendicular to the polarization direction, thereby exciting a bending resonance vibration in the optical fiber 11 so that the distal end thereof vibrates in a direction intersecting the longitudinal direction (Z direction). Accordingly, as shown by the arrow S in FIG. 5(b), the distal end of the optical fiber 11 can be vibrated in the X direction.

As described above, with the optical fiber scanner 20 according to this embodiment, by using the two piezoelectric elements 15A and 15B, it is possible to increase the amplitude of the vibration excited in the optical fiber 11 compared with the case in which the single piezoelectric element 15 is used.

Figure 6:
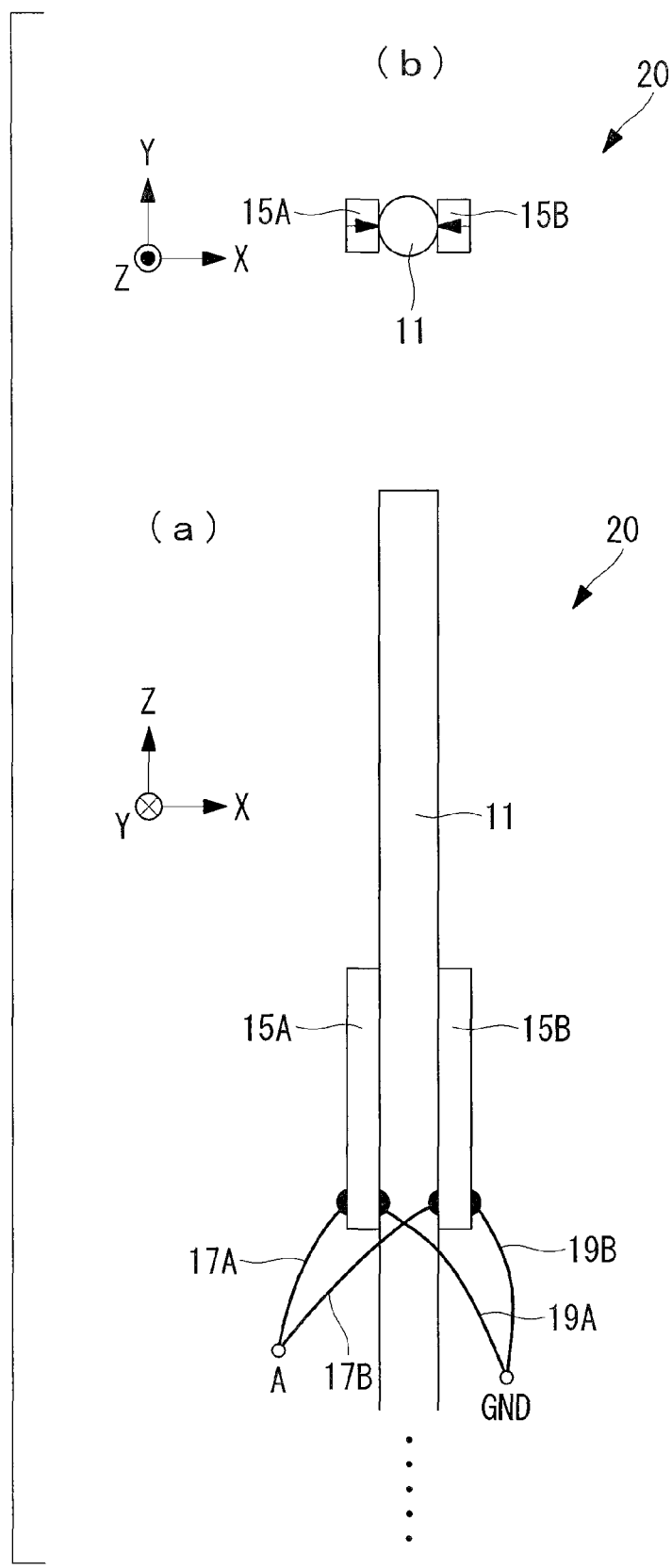
In FIG. 6, (a) is a diagram showing, in outline, the configuration of an optical fiber scanner according to a first modification of the second embodiment of the present invention, viewed in a direction perpendicular to the longitudinal direction, and (b) is a view of the optical fiber in (a) in the longitudinal direction from the forward side thereof.

In this embodiment, as a first modification, similarly to the first modification of the first embodiment, the conductive electrode 13 may be omitted, and the pair of piezoelectric elements 15A and 15B may be directly joined to the outer circumferential surface of the optical fiber 11. For example, FIGS. 6(a) and (b) show a state in which the rear surfaces of each of the piezoelectric elements 15A and 15B are joined to the outer circumferential surface of the optical fiber 11. The polarization directions of the piezoelectric elements 15A and 15B (see arrows) are different directions from each other; that is to say, they are both directions that point towards the optical fiber 11.

In this case, in the piezoelectric element 15A, for example, a common GND line 19A should be joined to the electrode 16 on the surface that is joined to the optical fiber 11 (the rear surface), and the lead wire 17A should be joined to the electrode 16 on the surface at the opposite side (the front surface). Also, in the piezoelectric element 15B, the lead wire 17B should be joined to the electrode 16 on the surface that is joined to the optical fiber 11 (the rear surface), and a common GND line 19B should be joined to the electrode 16 on the surface at the opposite side (the front surface).

With this modification, the structure can be simplified by virtue of the elimination of the conductive electrode 13.

Third Embodiment

Next, an optical fiber scanner 30 according to a third embodiment of the present invention will be described below with reference to the drawings.

Figure 7:
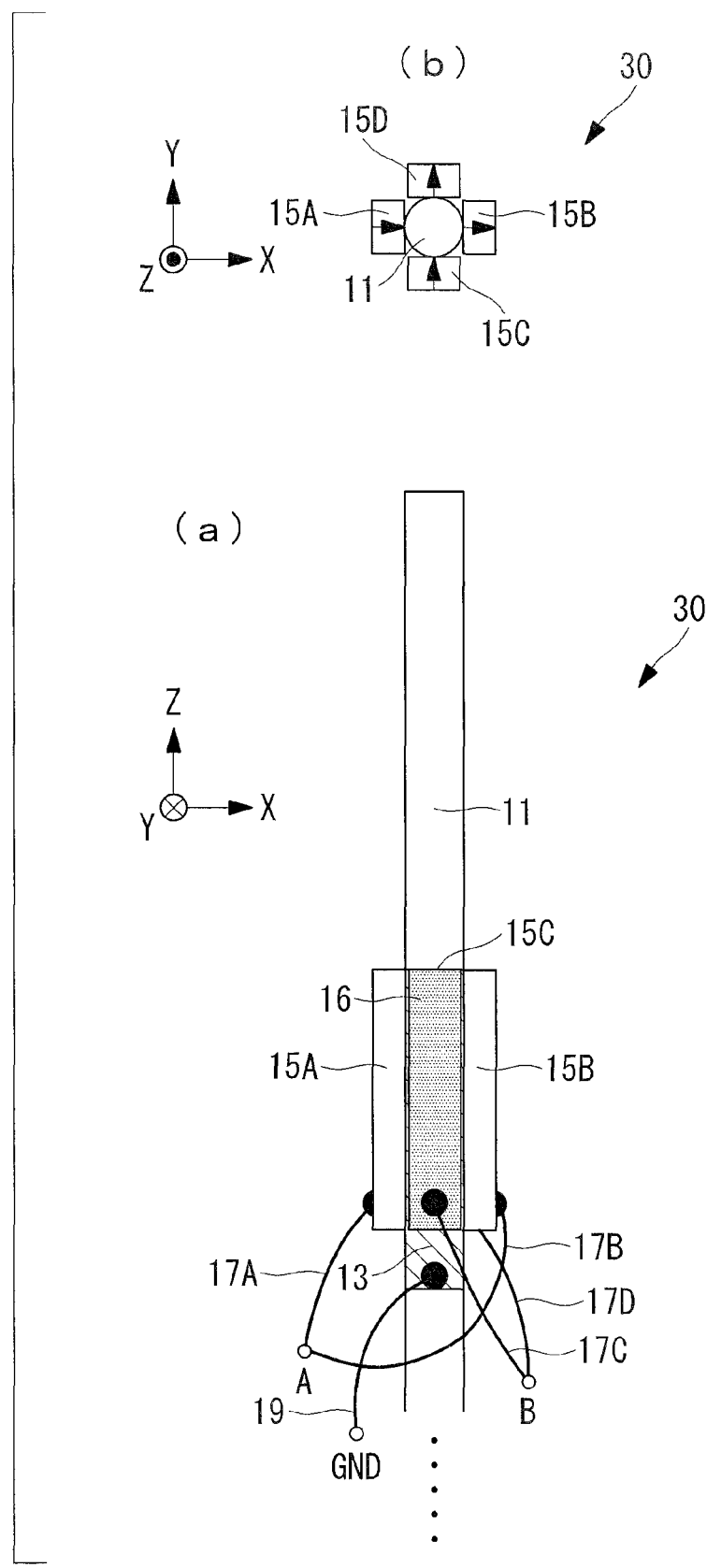
In FIG. 7, (a) is a diagram showing, in outline, the configuration of an optical fiber scanner according to a third embodiment of the present invention, viewed in a direction perpendicular to the longitudinal direction, and (b) is a view of the optical fiber in (a) in the longitudinal direction from the forward side thereof.

As shown in FIGS. 7(a) and (b), the optical fiber scanner 30 according to this embodiment differs from the second embodiment in that another pair of piezoelectric elements 15C and 15D, which are disposed so as to be shifted relative to the pair of piezoelectric elements 15A and 15B in the circumferential direction of the optical fiber 11, are provided.

In the following, parts having the same configuration as those in the optical fiber scanner 20 according to the second embodiment are assigned the same reference signs, and a description thereof will be omitted.

The pair of piezoelectric elements 15C and 15D, similarly to the pair of piezoelectric elements 15A and 15B, are disposed parallel to and opposing each other so as to flank the optical fiber 11 and are joined to the outer circumferential surface of the optical fiber 11 using adhesives, with the conductive electrode 13 disposed therebetween. In this embodiment, the rear surface of the piezoelectric element 15A and the front surface of the piezoelectric element 15B are joined to the conductive electrode 13, and the rear surface of the piezoelectric element 15C and the front surface of the piezoelectric element 15D are joined to the conductive electrode 13. Accordingly, the polarization directions of the piezoelectric element 15A and the piezoelectric element 15B are the same direction as each other, and the polarization directions of the piezoelectric element 15C and the piezoelectric element 15D are the same direction as each other.

In addition, the pair of piezoelectric elements 15A and 15B and the pair of piezoelectric elements 15C and 15D are disposed at positions that are shifted by 90° in the circumferential direction of the optical fiber 11. For example, the pair of piezoelectric elements 15A and 15B are disposed so as to face each other in the X direction, and the pair of piezoelectric elements 15C and 15D are disposed so as to face each other in the Y direction. These four piezoelectric elements 15A, 15B, 15C, and 15D each have width dimensions that are substantially equal to the diameter dimension of the optical fiber 11.

In the pair of piezoelectric elements 15A and 15B, driving lead wires 17A and 17B that constitute an A-phase are joined to the electrodes 16 on the surfaces at the opposite sides from the surfaces that are joined to the conductive electrode 13, using conductive adhesive. In the pair of piezoelectric elements 15C and 15D, driving lead wires 17C and 17D that constitute a B-phase are joined to the electrodes 16 at the opposite sides from the surfaces that are joined to the conductive electrode 13, using conductive adhesive. The common GND line 19 is joined to the conductive electrode 13 with conductive adhesive.

The operation of the thus-configured optical fiber scanner 30 will now be described.

Figure 8:
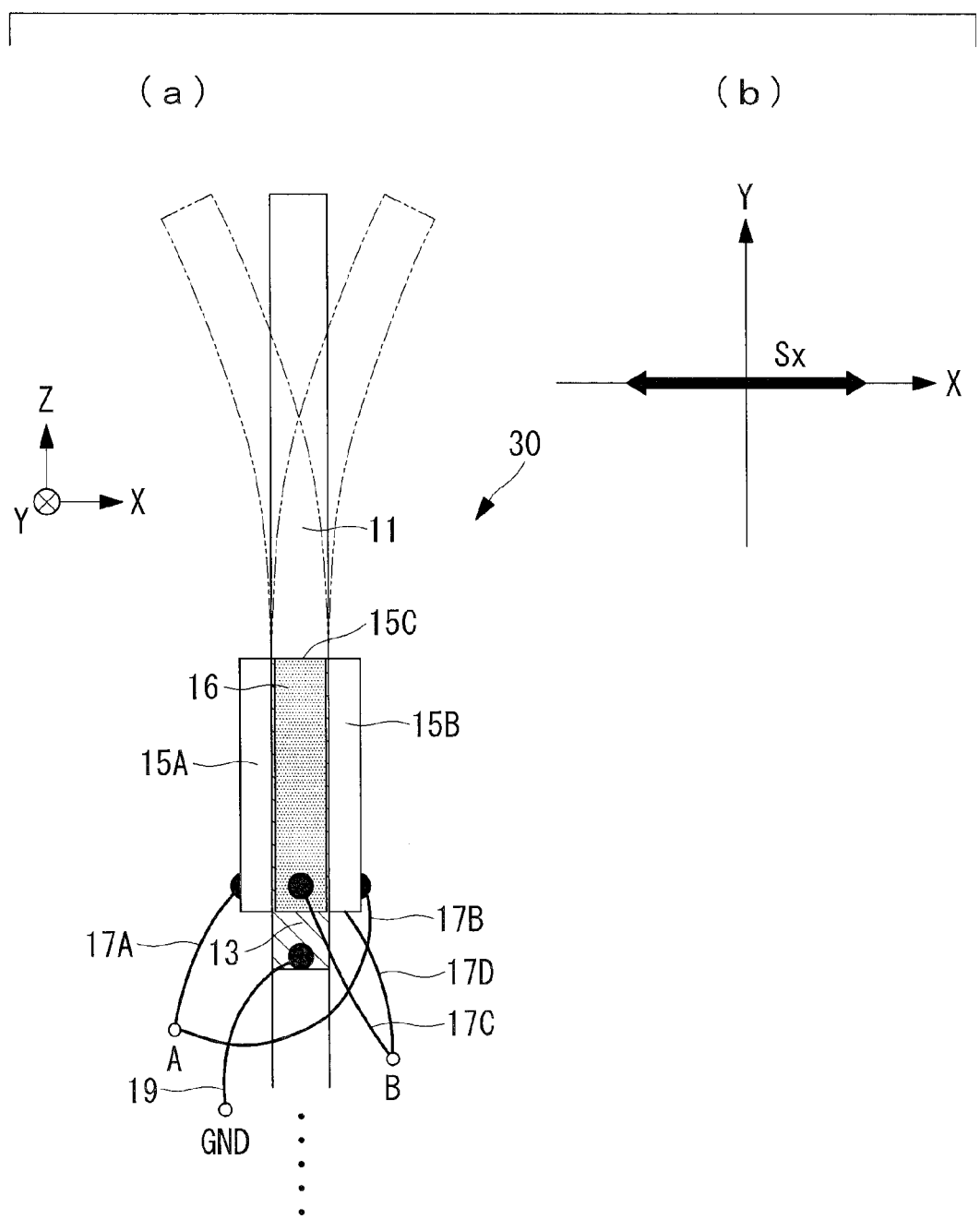
In FIG. 8, (a) is a diagram showing a state in which the distal end of the optical fiber in FIG. 7 is vibrated in the X direction, and (b) is a diagram showing the path traced out by the vibration of the distal end of the optical fiber in (a).

In the optical fiber scanner 30 according to this embodiment, when an alternating voltage corresponding to the frequency of the bending resonance vibration is applied to the A-phase of the pair of piezoelectric elements 15A and 15B via the lead wires 17A and 17B, the piezoelectric elements 15A and 15B together expand and contract in a direction perpendicular to the polarization directions, thereby exciting a bending resonance vibration in the optical fiber 11, as shown in FIG. 8(a). In this bending resonance vibration, the vicinity of the ends at the forward side of the piezoelectric elements 15A and 15B is a node, and the distal end of the optical fiber 11 is an antinode. Accordingly, as shown by the arrow Sx in FIG. 8(b), the distal end of the optical fiber 11 can be vibrated in a linear fashion in the X direction.

Figure 9:
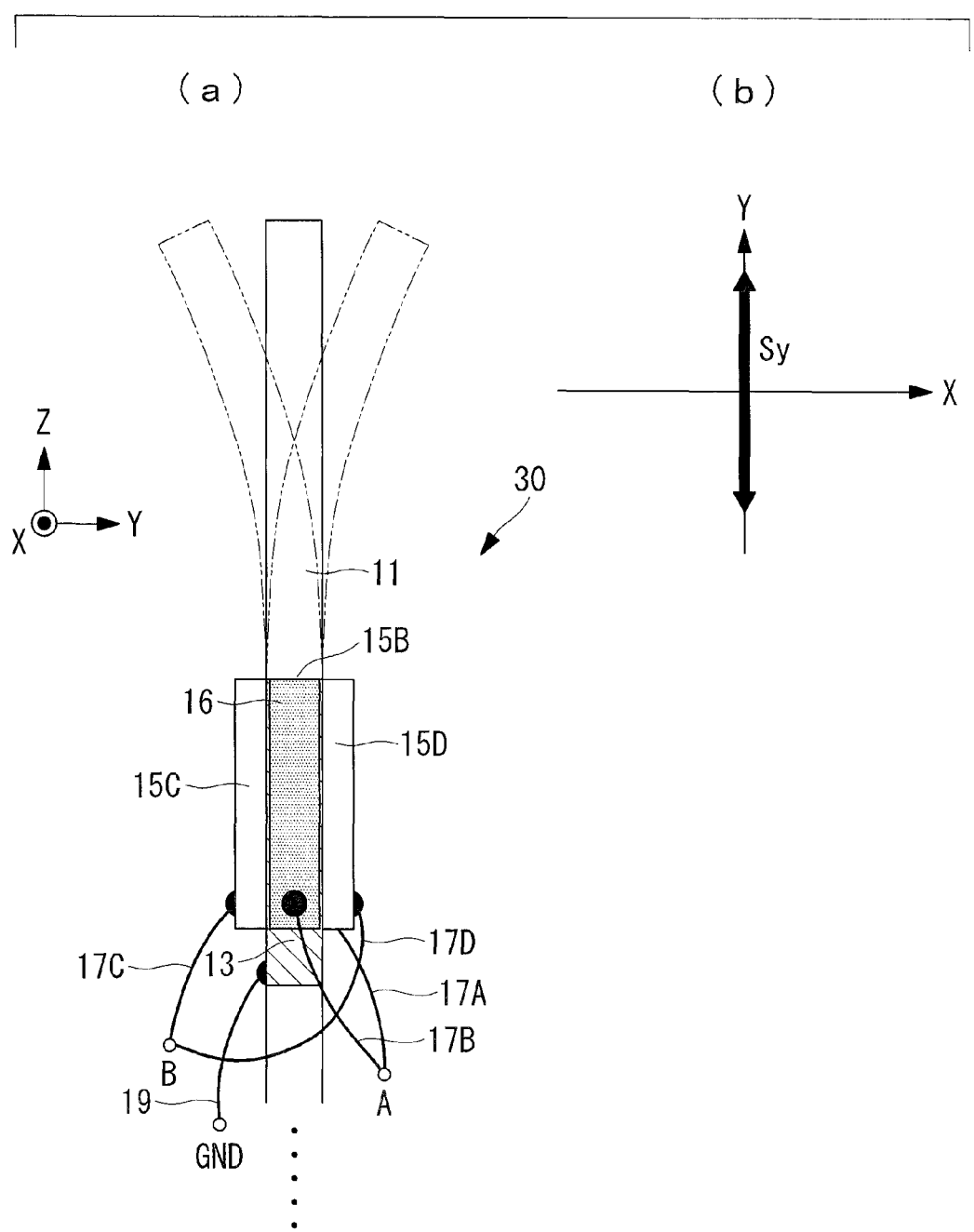
In FIG. 9, (a) is a diagram showing a state in which the distal end of the optical fiber in FIG. 7 is vibrated in the Y direction, and (b) is a diagram showing the path traced out by the vibration of the distal end of the optical fiber in (a).

On the other hand, when an alternating voltage corresponding to the frequency of the bending resonance vibration is applied in the thickness direction to the B-phase of the pair of piezoelectric elements 15C and 15D via the lead wires 17C and 17D, the piezoelectric elements 15C and 15D together expand and contract in a direction perpendicular to the polarization directions, thereby exciting a bending resonance vibration in the optical fiber 11, as shown in FIG. 9(a). In this bending resonance vibration, the vicinity of the ends at the forward side of the piezoelectric elements 15C and 15D is a node, and the distal end of the optical fiber 11 is an antinode. Accordingly, as shown by the arrow Sy in FIG. 9(b), the distal end of the optical fiber 11 can be vibrated in a linear fashion in the Y direction.

Figure 10:
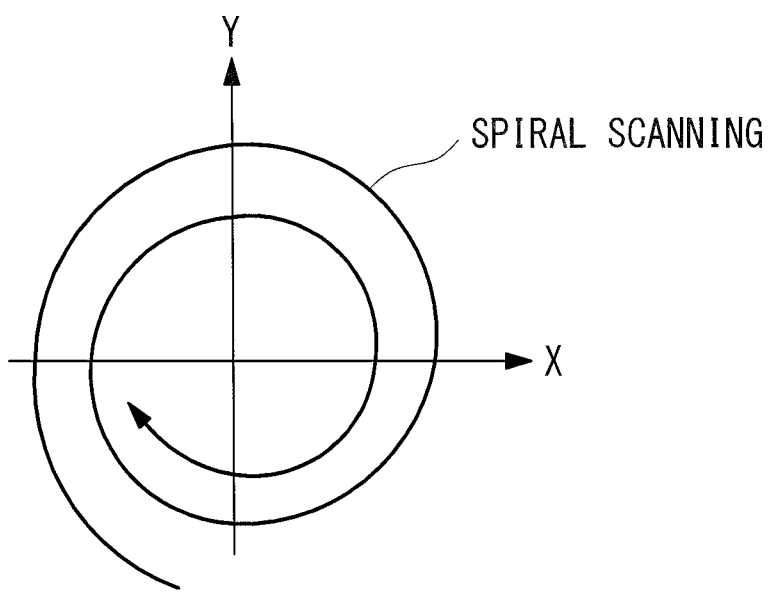
FIG. 10 is a diagram showing spiral scanning of the distal end of the optical fiber.

Thus, when an X-direction vibration and a Y-direction vibration are simultaneously generated in the optical fiber 11, and the phase of the alternating voltage applied to the piezoelectric elements 15A and 15B and the phase of the alternating voltage applied to the piezoelectric elements 15C and 15D are shifted by $\pi/2$, the distal end of the optical fiber 11 vibrates along a circular path. Then, as the magnitude of the alternating voltage is gradually increased or decreased, as shown in FIG. 10, the distal end of the optical fiber 11 vibrates along a spiral path (spiral scanning). Accordingly, it is possible to scan the illumination light on the subject two-dimensionally along a spiral path (spiral scanning).

Figure 11:
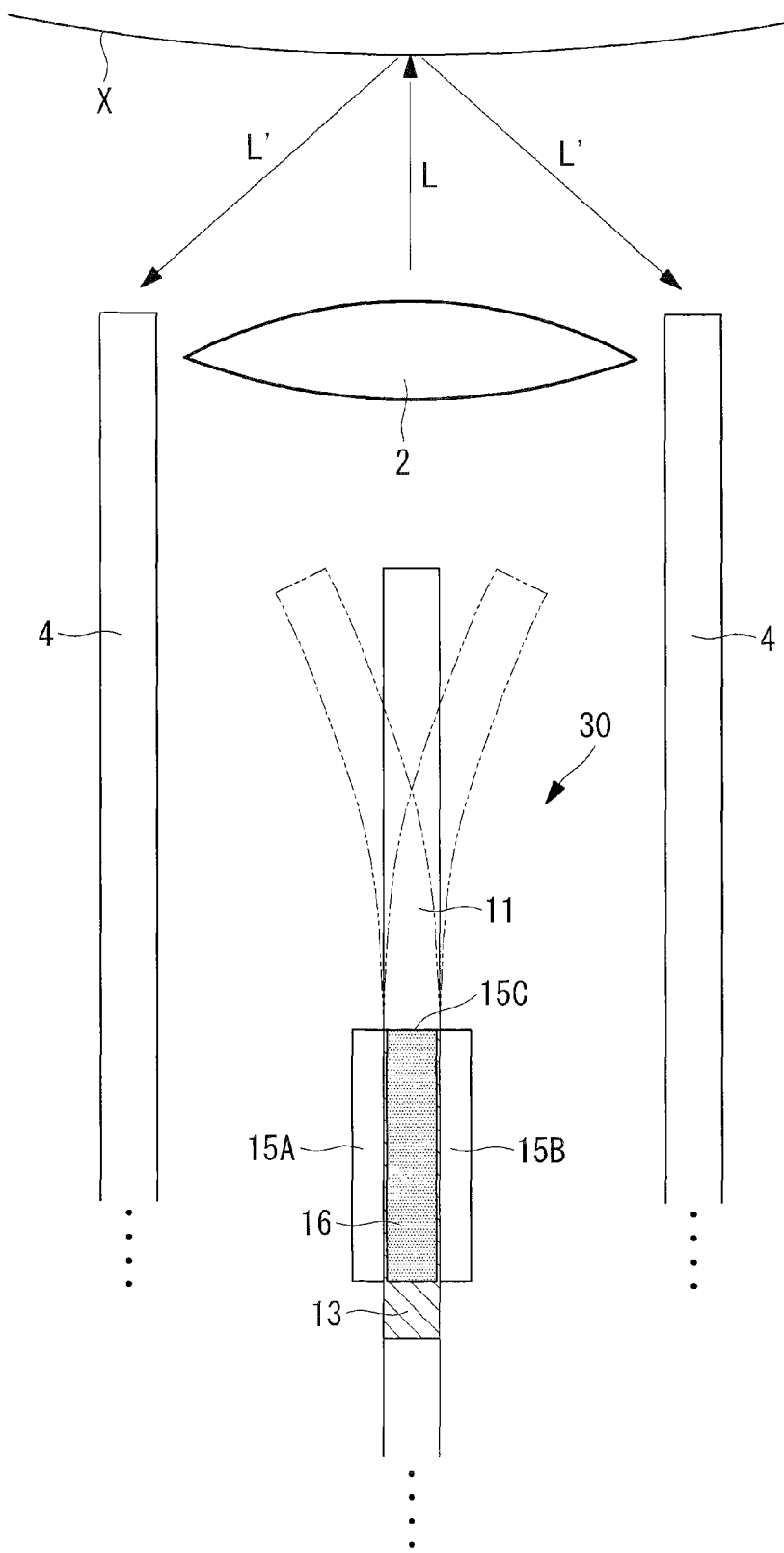
FIG. 11 is a diagram showing the application of the optical fiber scanner in FIG. 7 to an image forming apparatus.

A case in which the optical fiber scanner 30 according to this embodiment is applied to an image forming apparatus, as shown in FIG. 11, for example, will now be described. When the distal end of the optical fiber 11 is spirally vibrated in the state where a lens 2 is disposed facing the subject X, and the illumination light L that has propagated inside the optical fiber 11 is made to emerge from the distal end thereof, the illumination light L is collected by the lens 2, is radiated onto the subject X, and is two-dimensionally scanned on the subject X.

Reflected light L' from the subject X irradiated with the illumination light L is detected by a plurality of detection fibers 4. The image forming apparatus can form an image of the state at the front surface in the scanning region of the illumination light L on the subject X by detecting the reflected light L' using the detection fibers 4 in synchronization with the scanning period of the illumination light L.

This embodiment can be modified in the following ways.

Figure 12:
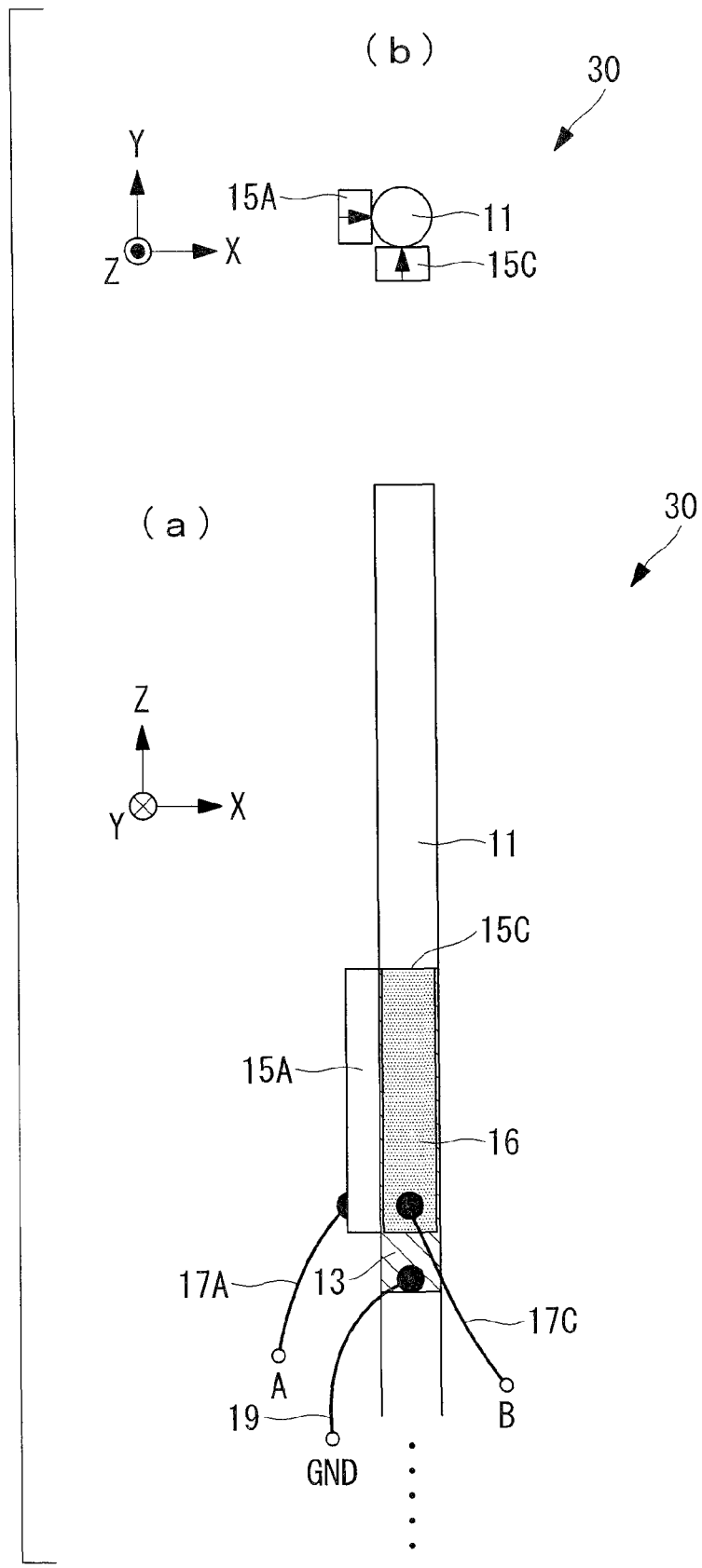
In FIG. 12, (a) is a diagram showing, in outline, the configuration of an optical fiber scanner according to a first modification of the third embodiment of the present invention, viewed in a direction perpendicular to the longitudinal direction, and (b) is a view of the optical fiber in (a) in the longitudinal direction from the forward side thereof.

As a first modification, instead of providing the four piezoelectric elements 15A, 15B, 15C, and 15D, as shown in FIGS. 12(a) and (b), the two piezoelectric elements 15A and 15C may be provided. The piezoelectric elements 15A and 15C are disposed at positions shifted by 90° in the circumferential direction of the optical fiber 11 so that their polarization directions are oriented perpendicular to each other.

With this modification, by applying alternating voltages to the two piezoelectric elements 15A and 15C with phases that are shifted by $\pi/2$, the distal end of the optical fiber 11 can be made to vibrate in a spiral fashion, and thus, it is possible to two-dimensionally scan the illumination light on the subject. Therefore, although an alternating voltage is still necessary, the configuration can be simplified compared with the case in which the four piezoelectric elements 15A, 15B, 150, and 15D are used.

Figure 13:
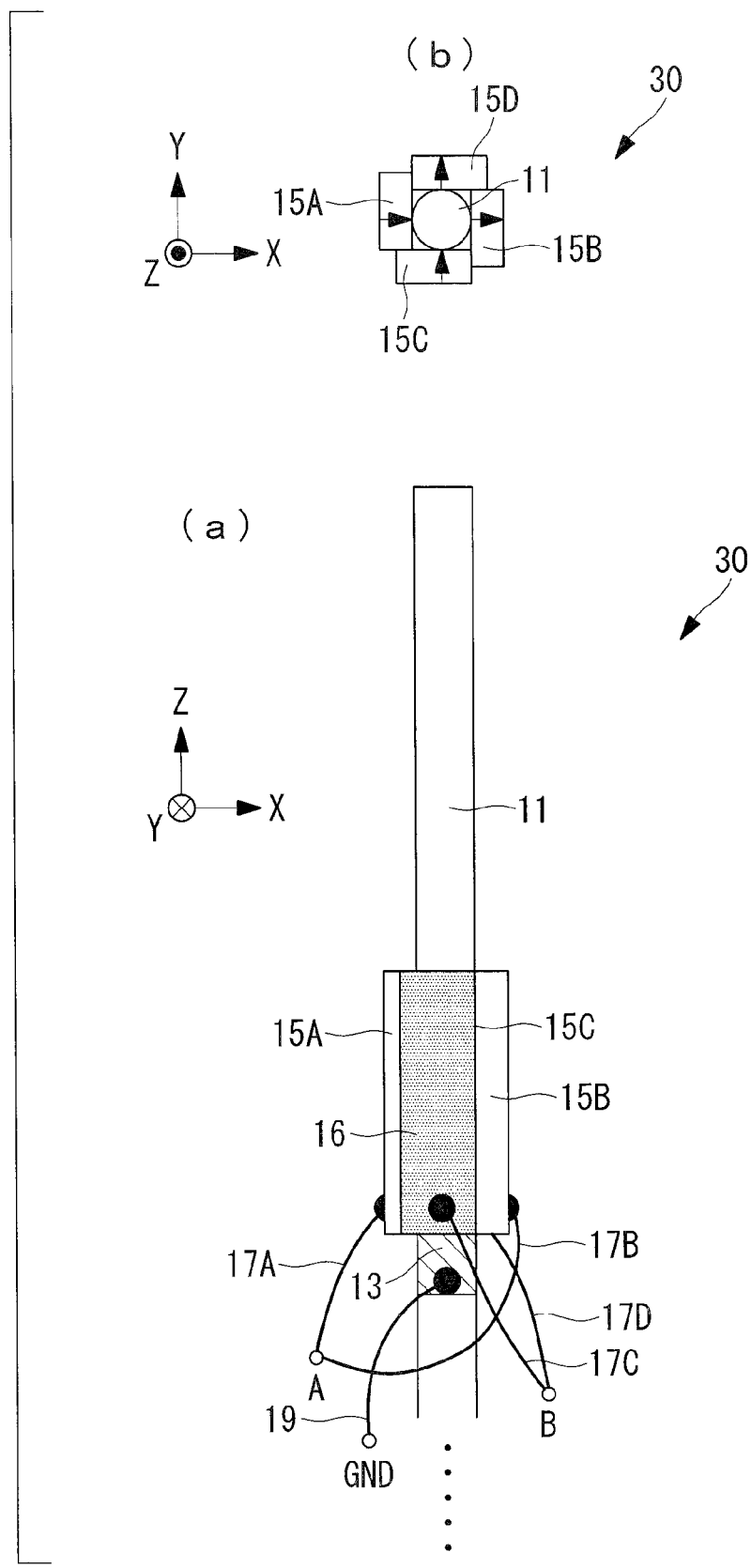
In FIG. 13, (a) is a diagram showing, in outline, the configuration of an optical fiber scanner according to a second modification of the third embodiment of the present invention, viewed in a direction perpendicular to the longitudinal direction, and (b) is a view of the optical fiber in (a) in the longitudinal direction from the forward side thereof.

As a second modification, as shown in FIGS. 13(a) and (b), the width dimension of each of the piezoelectric elements 15A, 15B, 15C, and 15D may be larger than the diameter dimension of the optical fiber 11. In this case, as shown in the same figure, each of the piezoelectric elements 15A, 15B, 15C, and 15D should be joined to the optical fiber 11 so as to be slightly shifted in the width direction thereof, so that either the front surfaces or rear surfaces and the side surfaces of neighboring piezoelectric elements 15A, 15B, 15C, and 15D in the circumferential direction of the optical fiber 11 are alternately in contact.

With this modification, the four piezoelectric elements 15A, 15B, 15C, and 15D can be positioned relative to each other in the circumferential direction of the optical fiber 11, thus simplifying assembly. In addition, the effective volumes of the piezoelectric elements 15A, 15B, 15C, and 15D are increased, and therefore, the amount of displacement in the expansion and contraction of the piezoelectric elements 15A, 15B, 15C, and 15D can be increased by inputting more energy thereto, and it is thus possible to increase the vibration amplitude of the optical fiber 11.

Figure 14:
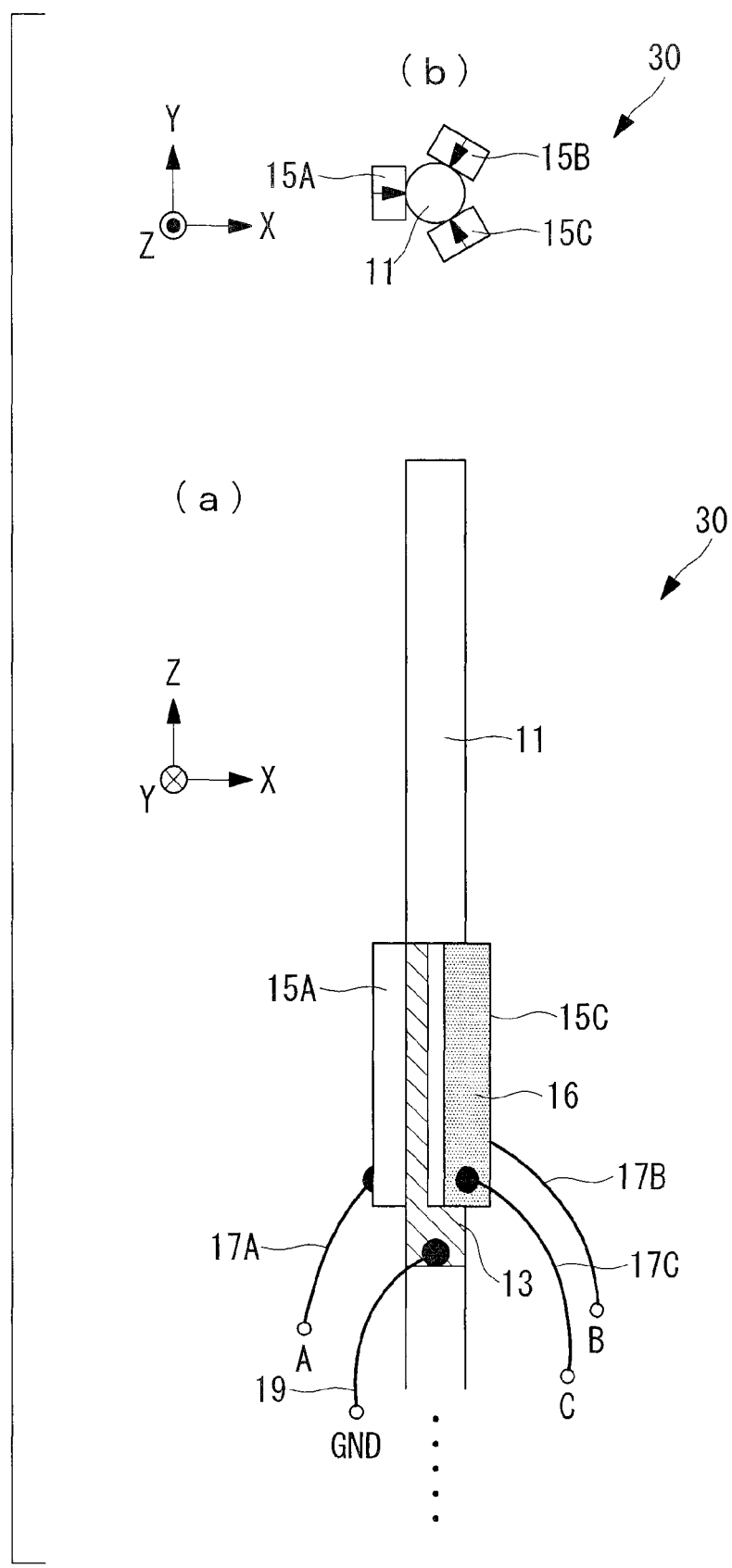
In FIG. 14, (a) is a diagram showing, in outline, the configuration of an optical fiber scanner according to a third modification of the third embodiment of the present invention, viewed in a direction perpendicular to the longitudinal direction thereof, and (b) is a view of the optical fiber in (a) in the longitudinal direction from the forward side thereof.

As a third modification, as shown in FIGS. 14(a) and (b), three piezoelectric elements 15A, 15B, and 15C may be disposed at positions 120° apart in the circumferential direction of the optical fiber 11 and joined to the optical fiber 11. In this case, the piezoelectric elements 15A, 15B, and 15C have their polarization directions pointing towards the optical fiber 11 and are joined to the conductive electrode 13 at the rear surfaces thereof. Also, driving lead wires 17A, 17B, and 17C that respectively constitute an A-phase, a B-phase, and a C-phase are joined to the electrodes 16 on surfaces (front surfaces) at the opposite sides from the surfaces of the piezoelectric elements 15A, 15B, and 15C that are joined to the conductive electrode 13, by using a conductive adhesive.

Thus, alternating voltages that are electrically shifted in phase by 120° from each other should be applied to the A-phase of the piezoelectric element 15A, the B-phase of the piezoelectric element 15B, and the C-phase of the piezoelectric element 15C. By doing so, the number of piezoelectric elements is reduced from 4 to 3, the distal end of the optical fiber 11 can be vibrated in a spiral manner, and thus the illumination light can be two-dimensionally scanned on the subject.

In addition, in this embodiment and the modifications thereof, the piezoelectric elements 15A, 15B, 15C, and 15D may each be directly joined to the outer circumferential surface of the optical fiber 11, without providing the conductive electrode 13. In this case, a common GND line 19B should be joined to the electrodes 16 on the surfaces (rear surfaces) of the piezoelectric elements 15A, 15B, 15C, and 15D that are joined to the optical fiber 11. By doing so, it is possible to simplify the configuration by virtue of the elimination of the conductive electrode 13.

Fourth Embodiment

Next, an optical fiber scanner 40 according to a fourth embodiment of the present invention will be described below with reference to the drawings.

Figure 15:
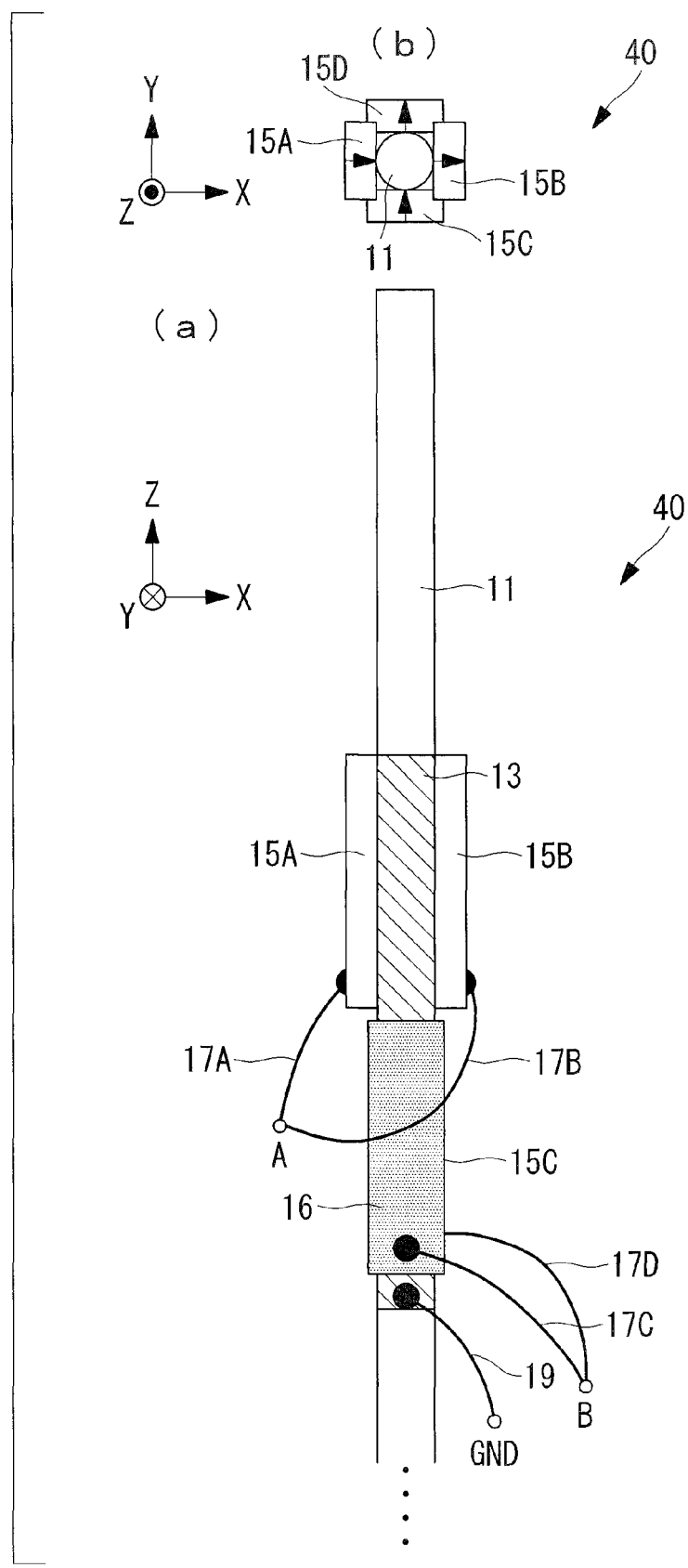
In FIG. 15, (a) is a diagram showing, in outline, the configuration of an optical fiber scanner according to a fourth embodiment of the present invention, viewed in a direction perpendicular to the longitudinal direction thereof, and (b) is a view of the optical fiber in (a) in the longitudinal direction from the forward side thereof.

As shown in FIGS. 15(a) and (b), the optical fiber scanner 40 according to this embodiment differs from the third embodiment in that another pair of piezoelectric elements 15C and 15D are disposed at positions shifted relative to the pair of piezoelectric elements 15A and 15B in the longitudinal direction of the optical fiber 11.

In the following, parts having the same configuration as those in the optical fiber scanner 30 according to the third embodiment are assigned the same reference signs, and a description thereof will be omitted.

In this embodiment, the piezoelectric elements 15A and 15B and the piezoelectric elements 15C and 15D are disposed at positions shifted also in the longitudinal direction of the optical fiber 11 so as not to overlap each other in the longitudinal direction of the optical fiber 11. FIGS. 15(a) and (b) show a configuration in which the pair of piezoelectric elements 15A and 15B, which constitute the A-phase, are disposed towards the distal end of the optical fiber 11, and the other pair of piezoelectric elements 15C and 15D, which constitute the B-phase, are disposed towards the base end of the optical fiber 11.

The rear surface of the piezoelectric element 15A and the front surface of the piezoelectric element 15B are joined to the conductive electrode 13, and the rear surface of the piezoelectric element 15C and the front surface of the piezoelectric element 15D are also joined to the conductive electrode 13. Accordingly, the polarization directions of the piezoelectric element 15A and the piezoelectric element 15B are the same direction as each other, and the polarization directions of the piezoelectric element 15C and the piezoelectric element 15D are the same direction as each other.

Then, lead wires 17A and 17B constituting the A-phase are joined to the surfaces of the piezoelectric elements 15A and 15B on the opposite sides from the surfaces that are joined to the conductive electrode 13, lead wires 17C and 17D constituting the B-phase are joined to the surfaces of the piezoelectric elements 15C and 15D on the opposite sides from the surfaces that are joined to the conductive electrode 13, and the common GND line 19 is joined to the conductive electrode 13.

The operation of the thus-configured optical fiber scanner 40 will now be described.

Figure 16:
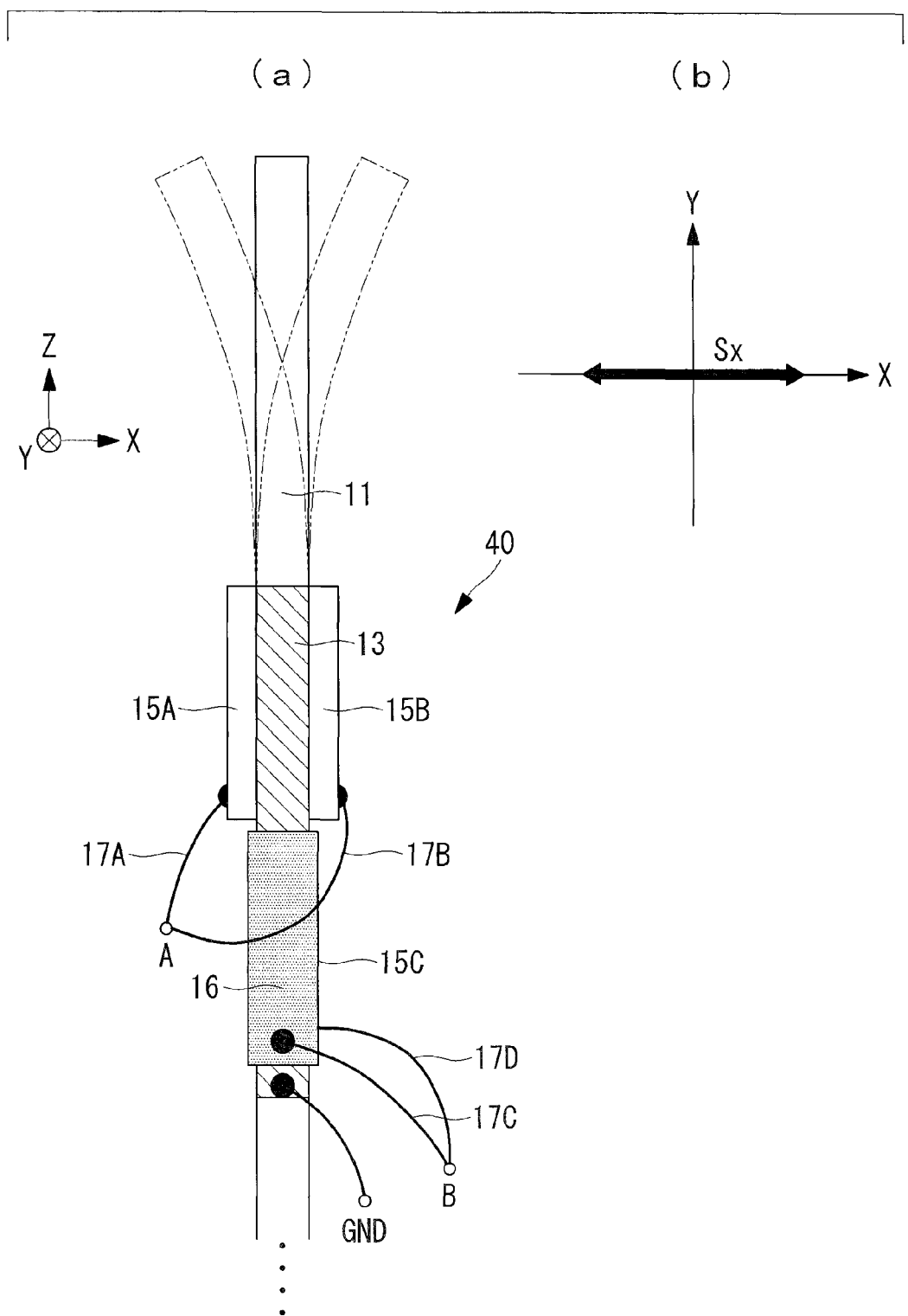
In FIG. 16, (a) is a diagram showing a state in which the distal end of the optical fiber in FIG. 15 is vibrated in the X direction, and (b) is a diagram showing the path traced out by the vibration of the distal end of the optical fiber in (a).

When an alternating voltage corresponding to the frequency of the bending resonance vibration is applied to the A-phase of the pair of piezoelectric elements 15A and 15B via the lead wires 17A and 17B, the piezoelectric elements 15A and 15B together expand and contract in a direction perpendicular to the polarization directions thereof, thereby exciting a bending resonance vibration in the optical fiber 11, as shown in FIG. 16(a). In this bending resonance vibration, the vicinity of the top ends of the piezoelectric elements 15A and 15B is a node, and the distal end of the optical fiber 11 is an antinode. Accordingly, as shown by arrow Sx in FIG. 16(b), the distal end of the optical fiber 11 can be vibrated in a linear fashion in the X direction.

Figure 17:
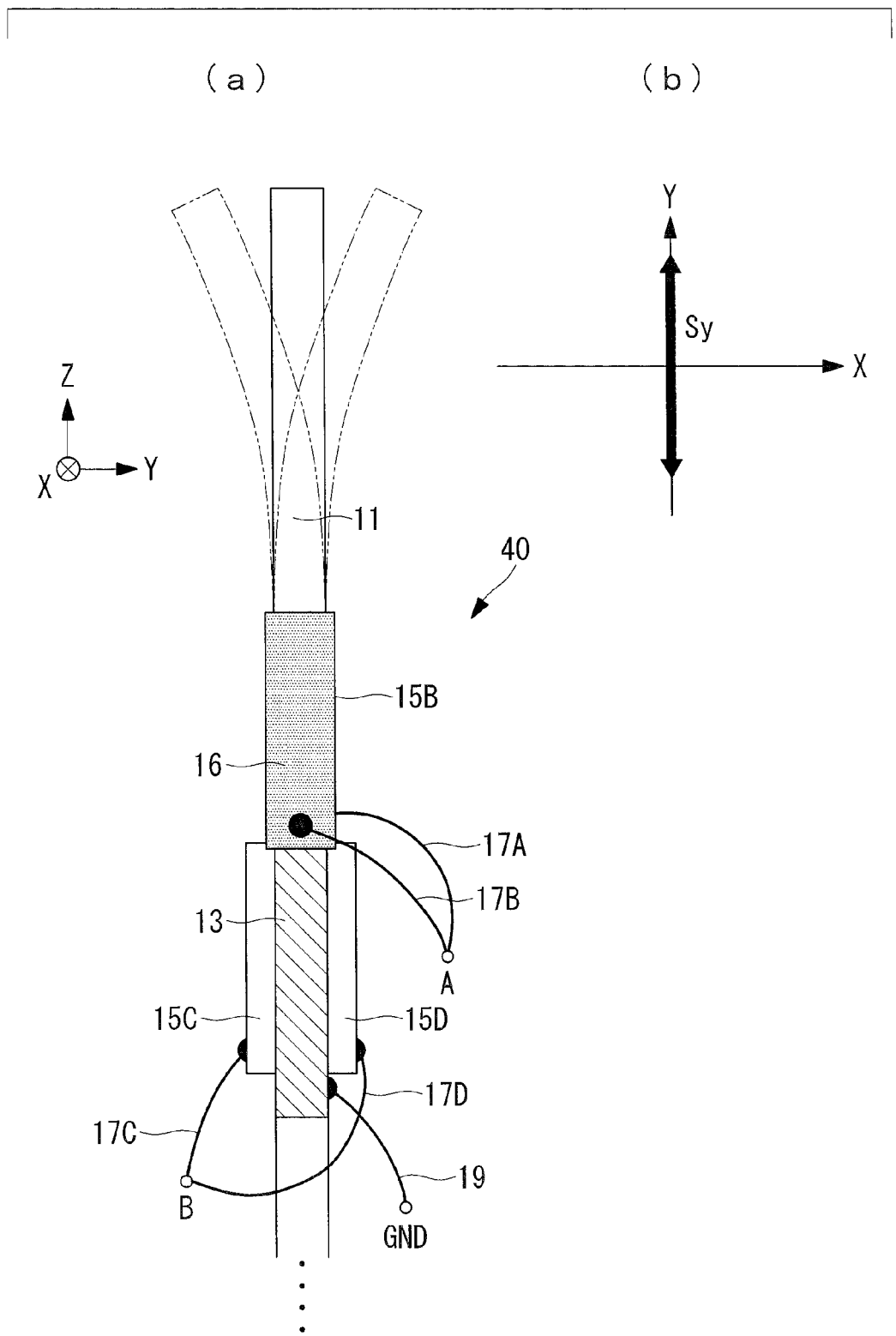
In FIG. 17, (a) is a diagram showing a state in which the distal end of the optical fiber in FIG. 15 is vibrated in the Y direction, and (b) is a diagram showing the path traced out by the vibration of the distal end of the optical fiber in (a).

On the other hand, when an alternating voltage corresponding to the frequency of the bending resonance vibration is applied to the B-phase of the other pair of piezoelectric elements 15C and 15D via the lead wires 17C and 17D, the piezoelectric elements 15C and 15D together expand and contract in a direction perpendicular to the polarization directions thereof, thereby exciting a bending resonance vibration in the optical fiber 11, as shown in FIG. 17(a). In this bending resonance vibration, the vicinity of the top ends of the piezoelectric elements 15C and 15D is a node, and the distal end of the optical fiber 11 is an antinode. Accordingly, as shown by arrow Sy in FIG. 17(b), the distal end of the optical fiber 11 can be vibrated in a linear fashion in the Y direction.

Thus, when an X-direction vibration and a Y-direction vibration are simultaneously generated in the optical fiber 11, and the phase of the alternating voltage applied to the piezoelectric elements 15A and 15B and the phase of the alternating voltage applied to the piezoelectric elements 15C and 15D are shifted by $\pi/2$, the distal end of the optical fiber 11 vibrates along a circular path. Then, when the magnitude of the alternating voltage is gradually increased or decreased, the distal end of the optical fiber 11 vibrates along a spiral path. Accordingly, the illumination light can be two-dimensionally scanned along a spiral path on the subject.

With the optical fiber scanner 40 according to this embodiment, by disposing the pair of piezoelectric elements 15A and 15B and the other pair of piezoelectric elements 15C and 15D on the outer circumferential surface of the optical fiber 11 at positions shifted so as not to overlap each other in the longitudinal direction thereof, the piezoelectric elements 15A, 15B, 15C, and 15D do not overlap each other in the circumferential direction and the longitudinal direction of the optical fiber 11, and therefore, it is possible to use large-volume, wide piezoelectric elements 15A, 15B, 15C, and 15D without increasing the overall size of the optical fiber scanner 40. Accordingly, a large amount of energy can be output from the piezoelectric elements 15A, 15B, 15C, and 15D, and the optical fiber 11 can be vibrated with a large amplitude.

Figure 18:
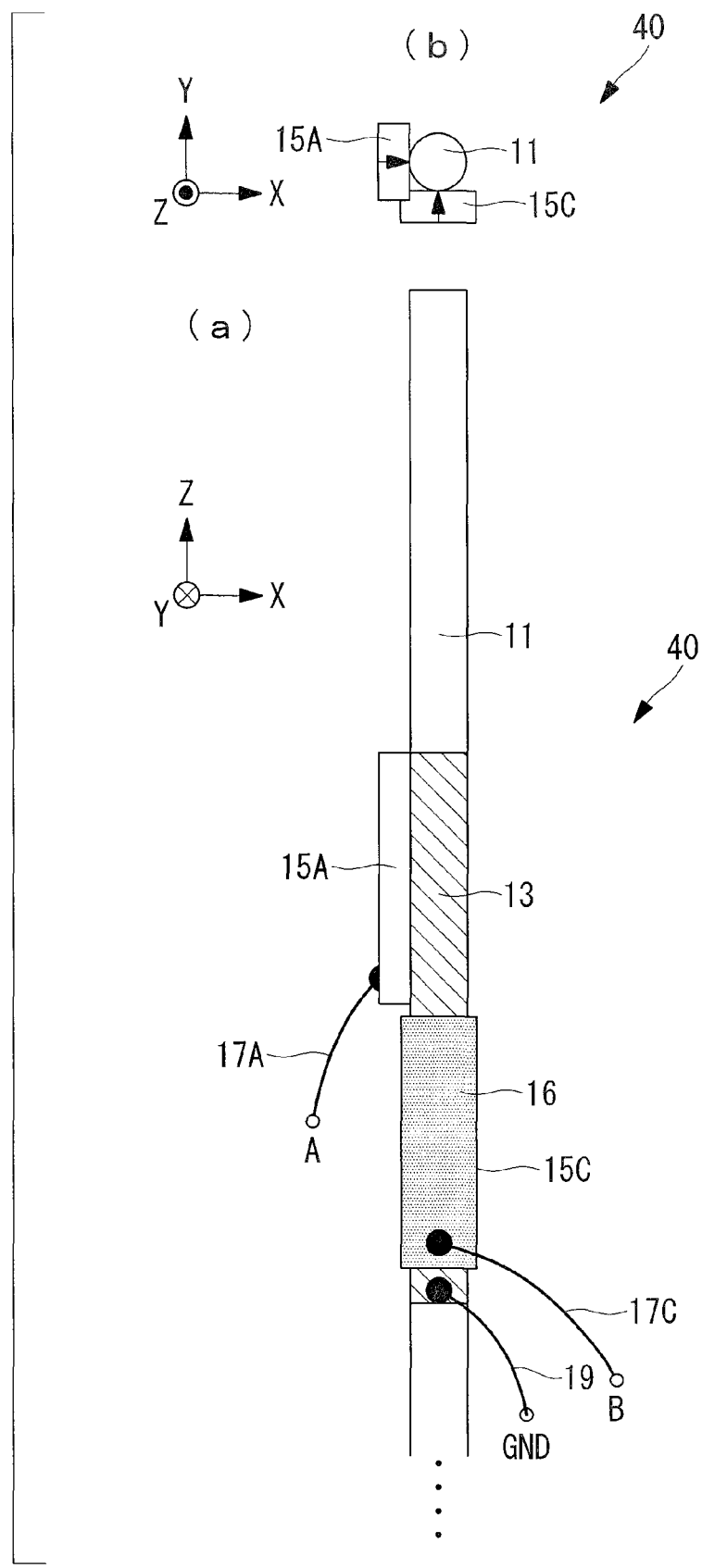
In FIG. 18, (a) is a diagram showing, in outline, the configuration of an optical fiber scanner according to a first modification of the fourth embodiment of the present invention, viewed in a direction perpendicular to the longitudinal direction thereof, and (b) is a view of the optical fiber in (a) in the longitudinal direction from the forward side thereof.

Although it has been assumed that the four piezoelectric elements 15A, 15B, 15C, and 15D are used in this embodiment, as shown in FIGS. 18(a) and (b), as a first modification, the two piezoelectric elements 15A and 15C may be used, and these two piezoelectric elements 15A and 15C may be shifted by 90° in the circumferential direction of the optical fiber 11, and may be disposed at positions that are also shifted in the longitudinal direction of the optical fiber 11 so as not to overlap in the longitudinal direction of the optical fiber 11. By doing so, although an alternating voltage is still necessary, the configuration can be simplified compared with the case in which the four piezoelectric elements 15A, 15B, 15C, and 15D are used.

In addition, in this embodiment and the modification thereof, the piezoelectric elements 15A, 15B, 15C, and 15D may each be directly joined to the outer circumferential surface of the optical fiber 11, without providing the conductive electrode 13. In this case, the common GND line 19B should be joined to the electrodes 16 on the surfaces (rear surfaces) of the piezoelectric elements 15A, 15B, 15C, and 15D that are joined to the optical fiber 11. By doing so, it is possible to simplify the structure by virtue of the elimination of the conductive electrode 13.

Fifth Embodiment

An optical fiber scanner 50 according to a fifth embodiment of the present invention will be described below with reference to the drawings.

Figure 19:
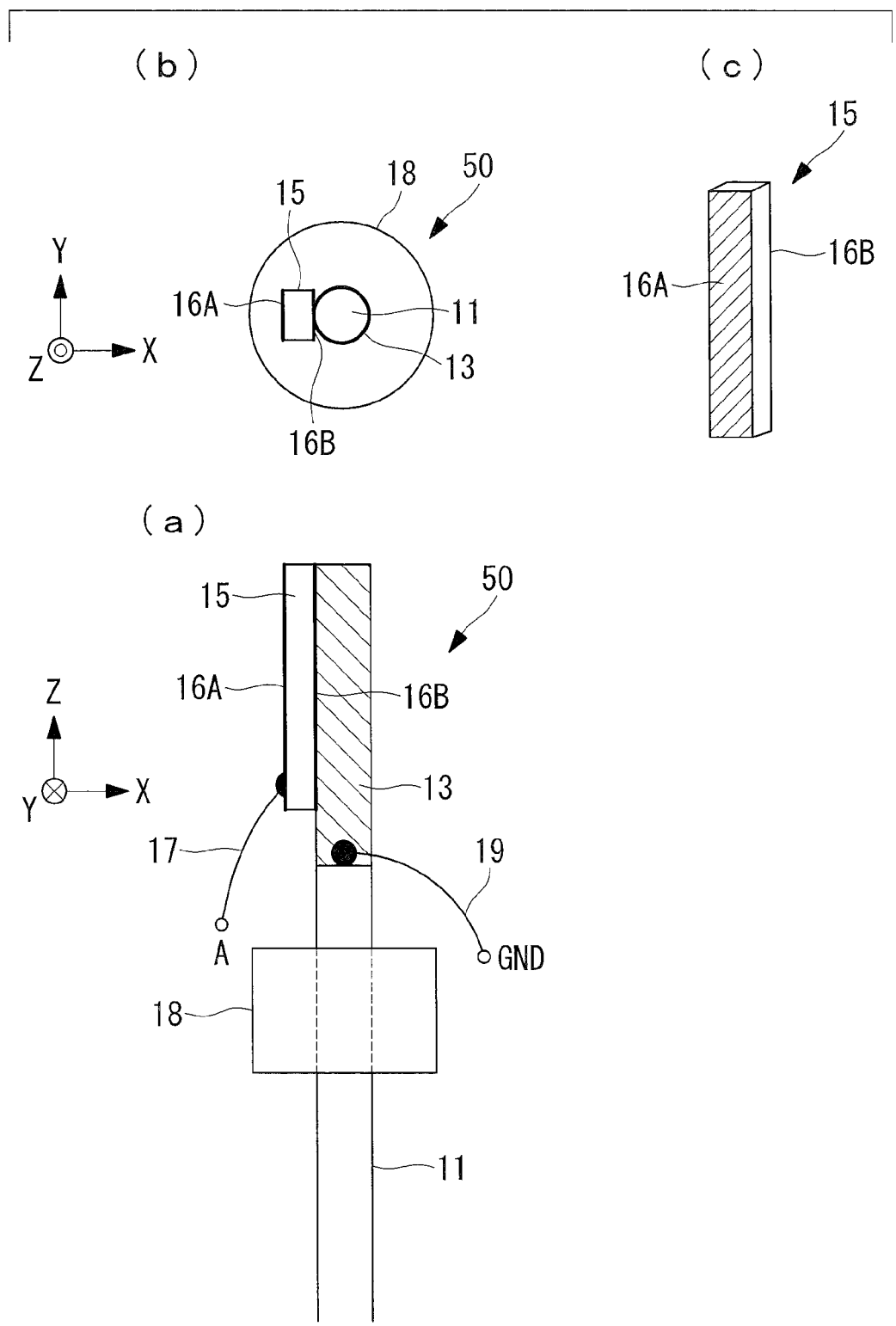
In FIG. 19, (a) is a diagram showing, in outline, the configuration of an optical fiber scanner according to a fifth embodiment of the present invention, viewed in a direction perpendicular to the longitudinal direction thereof, (b) is a view of (a) in the longitudinal direction from the forward side of the optical fiber, and (c) is a perspective view in which only a piezoelectric element in (a) is picked out.

As shown in FIGS. 19(a) and (b), the optical fiber scanner 50 according to this embodiment differs from the first embodiment in that a holding member 18 is provided, and in that the piezoelectric element 15 is bonded to the optical fiber 11 so that the position of the distal end of the piezoelectric element 15 is aligned with the position of the distal end of the optical fiber 11.

In the following, parts having the same configuration as those in the optical fiber scanner 10 according to the first embodiment are assigned the same reference signs, and a description thereof will be omitted.

The conductive electrode 13 is provided over a predetermined length in the longitudinal direction of the optical fiber 11, from the distal end of the optical fiber 11, and around the entire circumference thereof.

As shown in FIG. 19(c), the piezoelectric element 15 has electrodes 16A and 16B provided on the front surface and the rear surface thereof, respectively, and is subjected to polarization in the thickness direction thereof by a predetermined DC voltage. The piezoelectric element 15 is bonded to the optical fiber 11 so that the thickness direction thereof is directed in a diameter direction of the optical fiber 11 and so that the position of the distal end thereof is aligned with the position of the distal end of the optical fiber 11.

The holding member 18 is for keeping a position on the optical fiber 11 that is farther towards the base side than the conductive electrode 13 is at a fixed position. More concretely, the holding member 18 is a ring-shaped member into which the optical fiber 11 is inserted, and the inner surface thereof is joined to the outer circumferential surface of the optical fiber 11 with an adhesive. The holding member 18 is formed of a comparatively high-density metal such as stainless steel or a ceramic and has a mass that is sufficiently large relative to that of the distal end portion of the optical fiber 11 and the piezoelectric element 15, which are disposed farther towards the forward side than the holding member 18 is.

The operation of the thus-configured optical fiber scanner 50 will be described below.

To scan illumination light emitted from the light source on the subject by using the optical fiber scanner 50 according to this embodiment, first, an alternating voltage corresponding to the frequency of the bending resonance vibration is applied to the A-phase of the piezoelectric element 15 via the lead wire 17.

Figure 20:
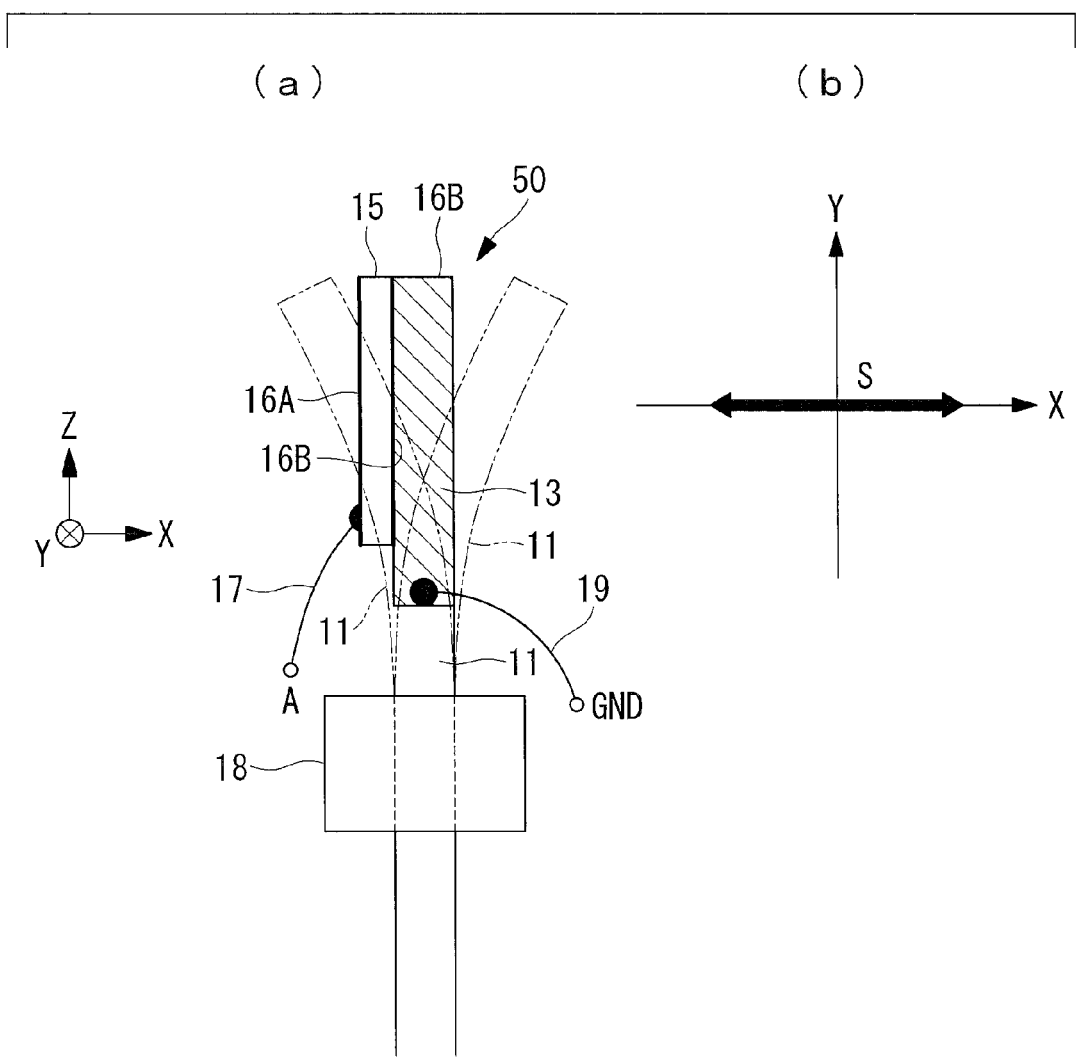
In FIG. 20, (a) is a diagram showing a state in which the distal end of the optical fiber in FIG. 19 is vibrated in the X direction, and (b) is a diagram showing the path traced out by the vibration of the distal end of the optical fiber in (a).

When the alternating voltage is applied to the piezoelectric element 15 in the thickness direction thereof, the piezoelectric element 15 expands and contracts in a direction perpendicular to the polarization direction, in other words, in a direction perpendicular to the thickness direction. Accordingly, as shown in FIG. 20(a), in a portion of the optical fiber 11 farther towards the forward side than the holding member 18 is, a bending resonance vibration is excited so that the distal end vibrates in a direction (X direction) that intersects the longitudinal direction (Z direction). At this time, since the holding member 18 is sufficiently heavy relative to the mass of the distal end portion of the optical fiber 11, a first-order bending vibration in which the vicinity of the distal end of the holding member 18 is a fixed end is stably excited in the optical fiber 11.

In this state, when the illumination light emitted from the light source is guided by the optical fiber 11 and emerges from the distal end thereof, as shown in FIG. 20(b), the illumination light can be scanned on the subject in a reciprocating manner in the X direction in accordance with the linear vibration of the distal end of the optical fiber 11. The arrow S in FIG. 20(b) shows the path traced out by the distal end of the vibrating optical fiber 11.

In this case, with the optical fiber scanner 50 according to this embodiment, by joining the piezoelectric element 15 directly to the optical fiber 11 over a predetermined length from the distal end of the optical fiber 11 by using the adhesive, the expansion and contraction motion of the piezoelectric element 15 is directly transferred to the distal end of the optical fiber 11. Accordingly, the distal end of the optical fiber 11 is made to forcedly vibrate in the X direction according to the expansion and contraction motion of the piezoelectric element 15. As a result, the light emerging from the distal end of the optical fiber 11 can be scanned in the intended reciprocating manner along a straight-line path in the X direction.

In addition, since the conductive electrode 13 has high hardness and a thickness on the order of several micrometers, the force transferred from the piezoelectric element 15 to the optical fiber 11 undergoes almost no attenuation in the conductive electrode 13. Therefore, the optical fiber 11 can be made to undergo a bending vibration with high efficiency.

Furthermore, by providing the conductive electrode 13 between the optical fiber 11 and the piezoelectric element 15, it is not necessary to extend the common GND line 19 from the electrode 16B on the rear surface of the piezoelectric element 15, which is joined to the optical fiber 11; instead, the common GND line 19 can be extended from any position on the conductive electrode 13. Therefore, routing of the lead wire 17 and the common GND line 19 can be simplified.

This embodiment can be modified in the following ways.

Figure 21:
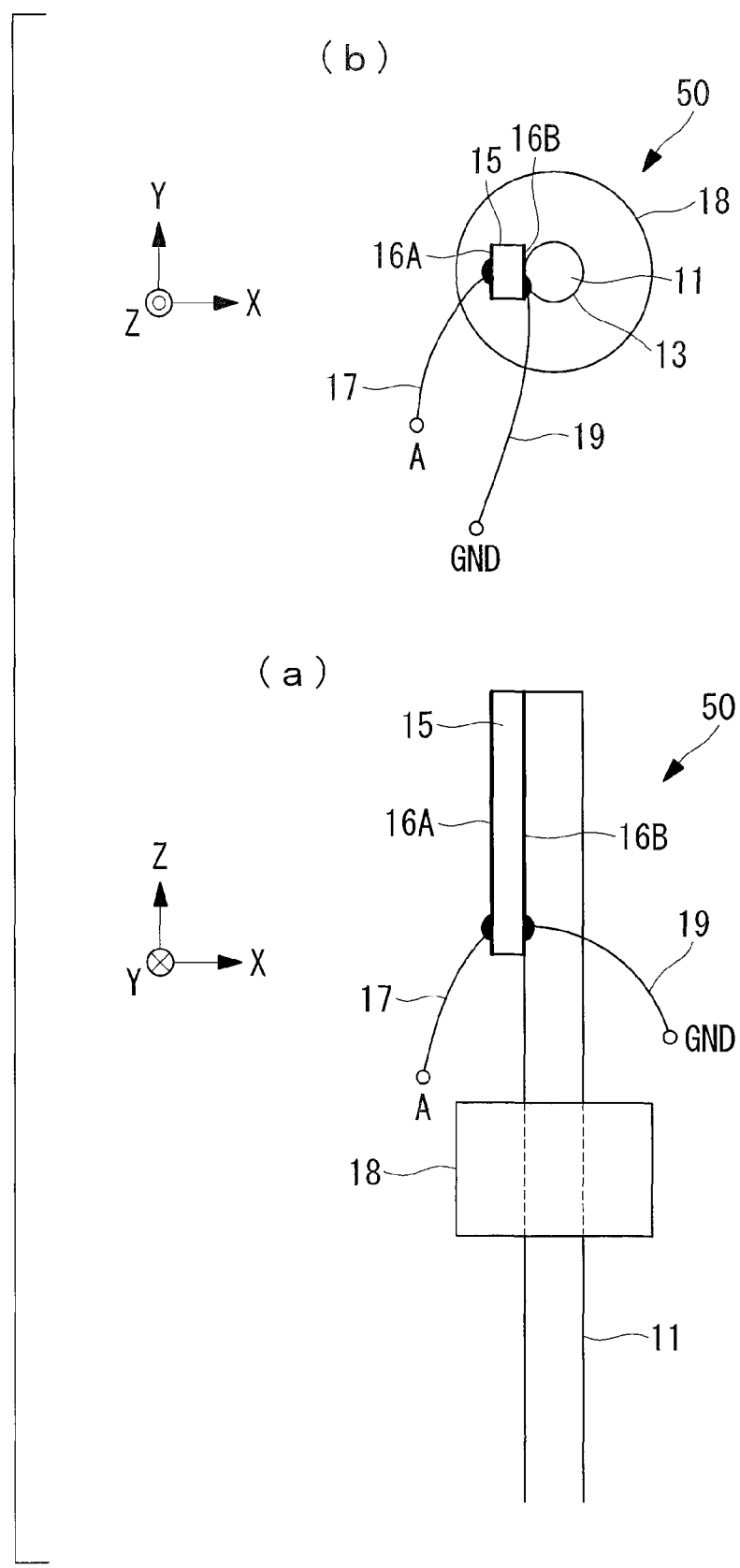
In FIG. 21, (a) is a diagram showing, in outline, the configuration of an optical fiber scanner according to a first modification of the fifth embodiment of the present invention, viewed in a direction perpendicular to the longitudinal direction thereof, and (b) is a view of the optical fiber in (a) in the longitudinal direction from the forward side thereof.

As a first modification, instead of disposing the conductive electrode 13 between the optical fiber 11 and the piezoelectric element 15, as shown in FIGS. 21(a) and (b), the electrode 16B on the rear surface of the piezoelectric element 15 may be directly joined to the outer circumferential surface of the optical fiber 11, and the common GND line 19 may be connected at a position on the rear surface where this electrode 16B is exposed, by using a conductive adhesive. In other words, the electrode 16B on the rear surface of the piezoelectric element 15 doubles as the conductive electrode.

With this modification, it is possible to directly transfer the force from the piezoelectric element 15 to the optical fiber 11. Also, it is possible to simplify the structure by virtue of the elimination of the conductive electrode 13.

Figure 22:
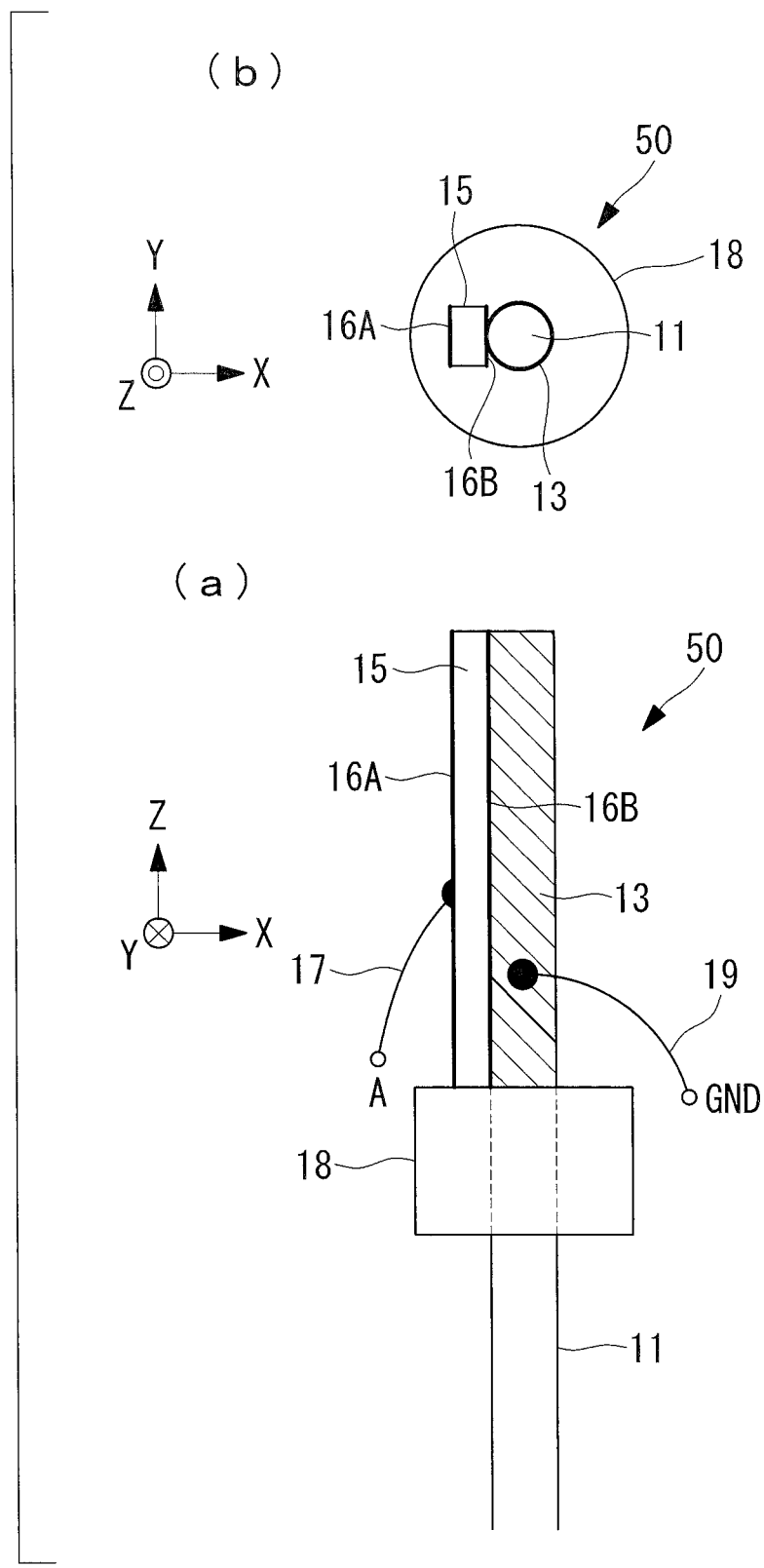
In FIG. 22, (a) is a diagram showing, in outline, the configuration of an optical fiber scanner according to a second modification of the fifth embodiment of the present invention, viewed in a direction perpendicular to the longitudinal direction, and (b) is a view of the optical fiber in (a) in the longitudinal direction from the forward side thereof.

As a second modification, as shown in FIGS. 22(a) and (b), the piezoelectric element 15 may be provided over the entire length from the distal end of the optical fiber 11 to the holding member 18 or the vicinity thereof.

With this modification, the force that the expanding and contracting piezoelectric element 15 exerts on the optical fiber 11 can be made larger.

Figure 23:
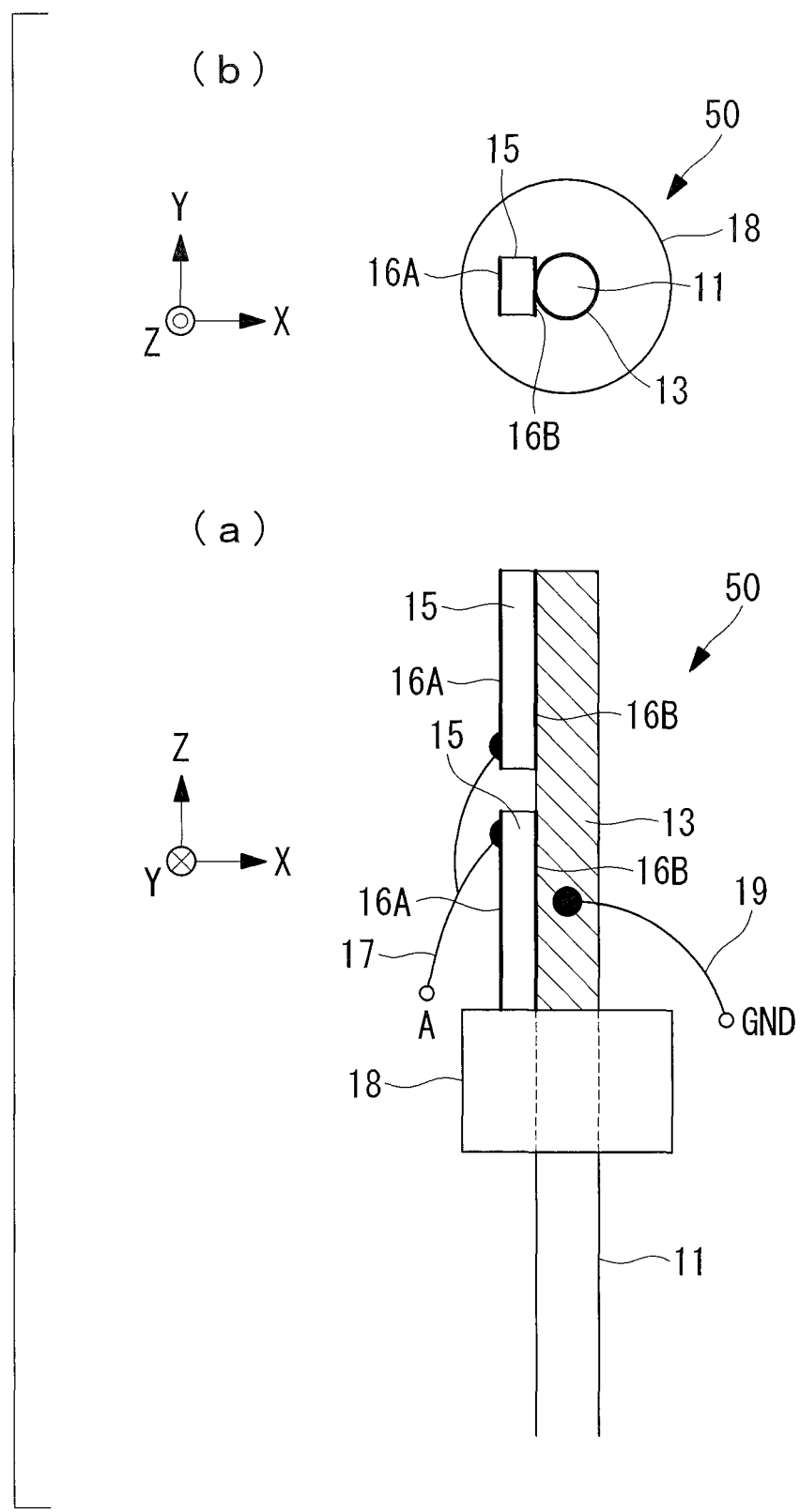
In FIG. 23, (a) is a diagram showing, in outline, the configuration of an optical fiber scanner according to a third modification of the fifth embodiment of the present invention, viewed in a direction perpendicular to the longitudinal direction, and (b) is a view of the optical fiber in (a) in the longitudinal direction from the forward side thereof.

As a third modification, as shown in FIGS. 23(a) and (b), the piezoelectric element 15 of the second modification may be divided into a plurality of parts (two in the illustrated example) in the longitudinal direction of the optical fiber 11.

With this modification, even piezoelectric elements with short dimensions can be effectively used, and the design restrictions of the piezoelectric elements that are used can be relaxed.

Figure 24:
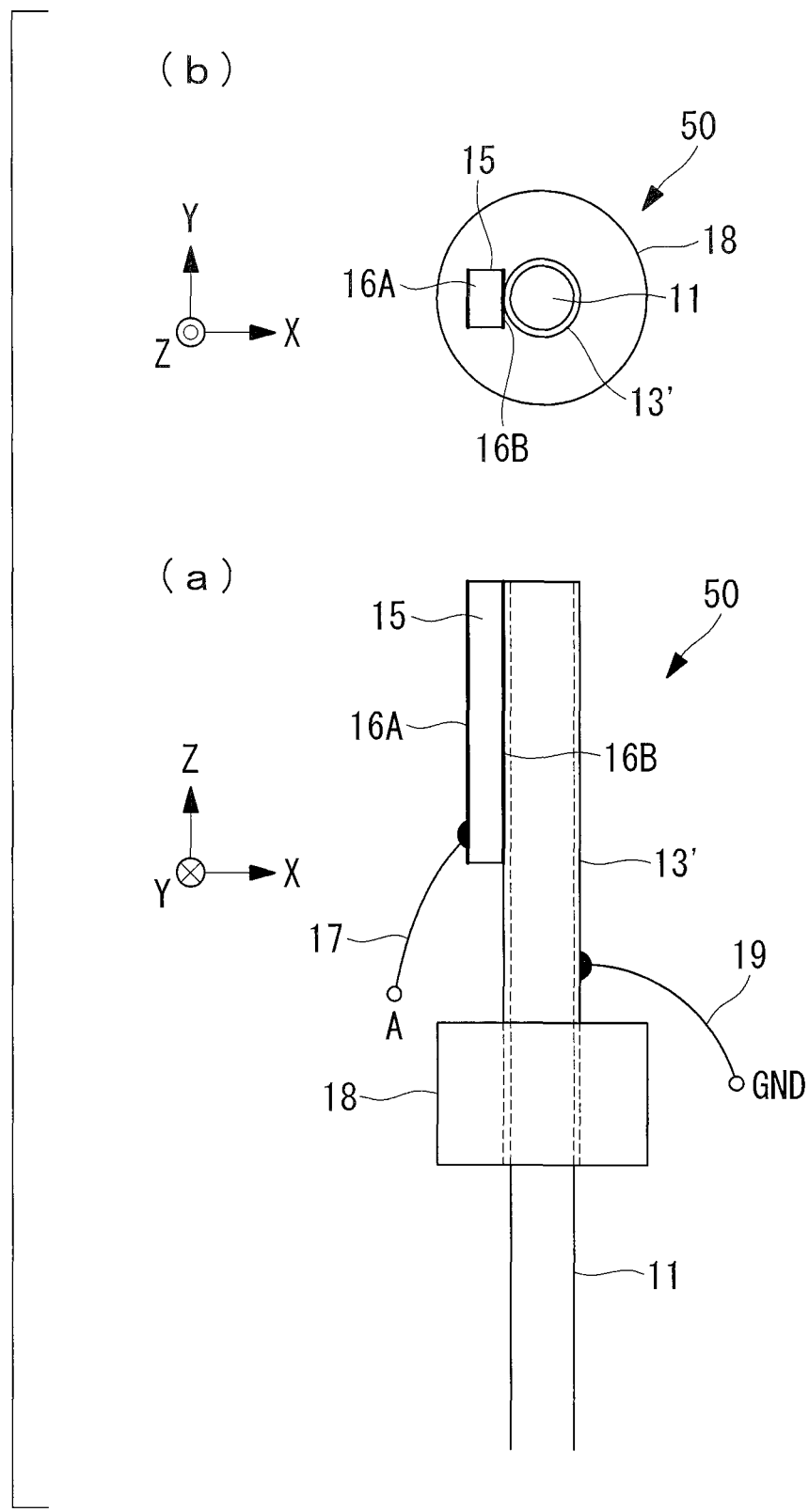
In FIG. 24, (a) is a diagram showing, in outline, the configuration of an optical fiber scanner according to a fourth modification of the fifth embodiment of the present invention, viewed in a direction perpendicular to the longitudinal direction, and (b) is a view of the optical fiber in (a) in the longitudinal direction from the forward side thereof.

As a fourth modification, instead of forming the conductive electrode 13 by covering the outer circumferential surface of the optical fiber 11 with a metal film, as shown in FIGS. 24(a) and (b), a cylindrical microtube (electrode member) 13' that is made of metal may be used as a conductive electrode. Nickel or copper is preferable as the material for the microtube 13'.

With this modification, processing such as sputtering for forming a metal film on the outer circumferential surface of the optical fiber 11 becomes unnecessary, which can simplify the fabrication. In addition, the common GND line 19 can be joined at any position on the microtube 13', allowing the fabrication to be simplified.

Figure 25:
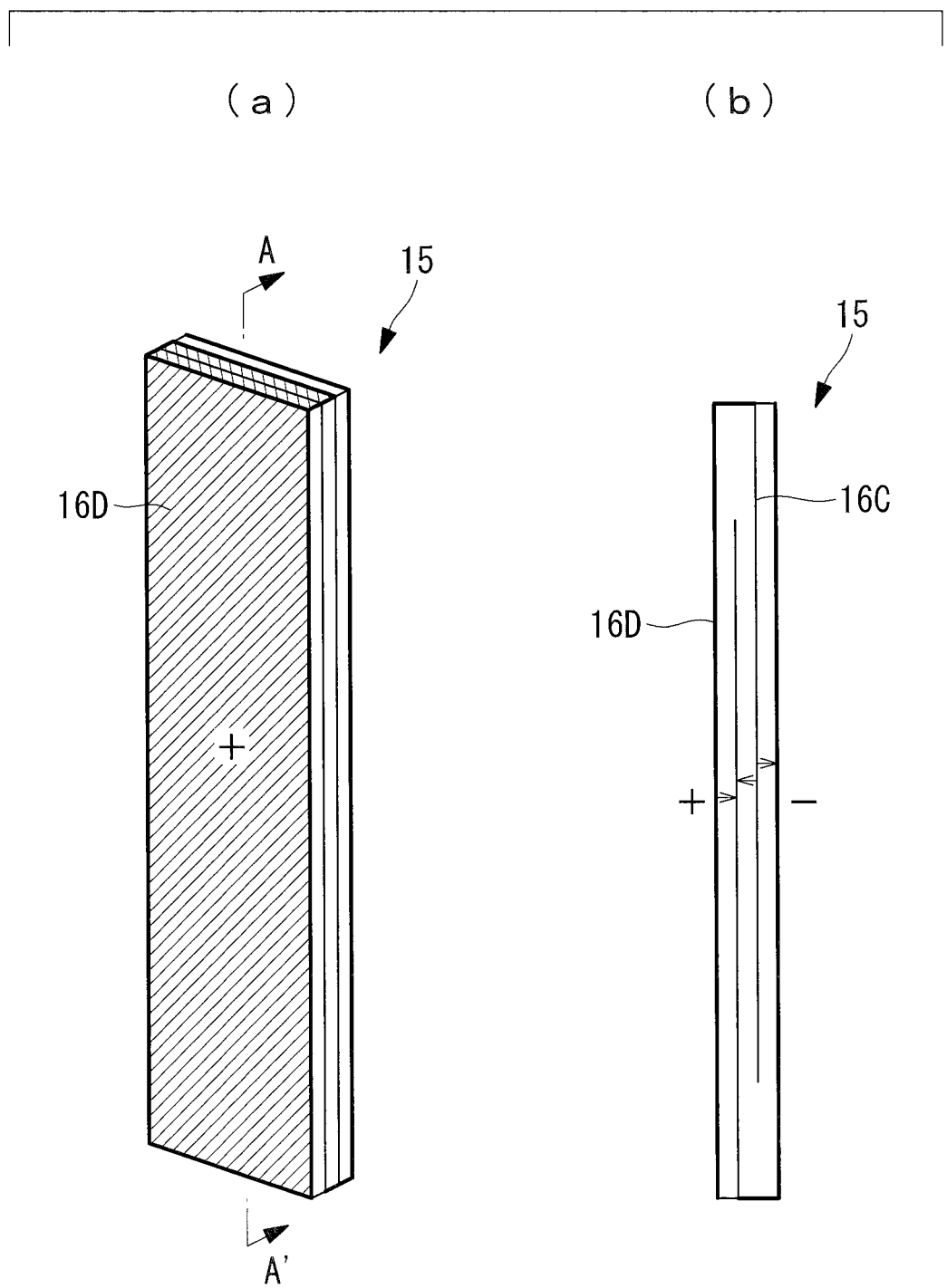
In FIG. 25, (a) is a perspective view showing, in outline, the configuration of a piezoelectric element provided in an optical fiber scanner according to a fifth modification of the fifth embodiment of the present invention, and (b) is a cross-section along A-A' in (a).

As a fifth modification, as shown in FIGS. 25(a) and (b), a stacked-type piezoelectric element in which a plurality of (three in the illustrated example) thin piezoelectric sheets (piezoelectric layers) are stacked in the thickness direction thereof may be used as the piezoelectric element 15. FIG. 25(a) shows the appearance of a stacked-type piezoelectric element 15, and 25(b) shows a cross-section along line A-A' in FIG. 25(a). The piezoelectric sheet disposed at the inner side has an internal electrode 16C, and an external electrode 16D is provided on the front surface at the outer side of the piezoelectric sheet.

With this modification, a larger force can be produced for the same voltage applied to the piezoelectric element 15.

Sixth Embodiment

Next, an optical fiber scanner 60 according to a sixth embodiment of the present invention will be described below with reference to the drawings.

Figure 26:
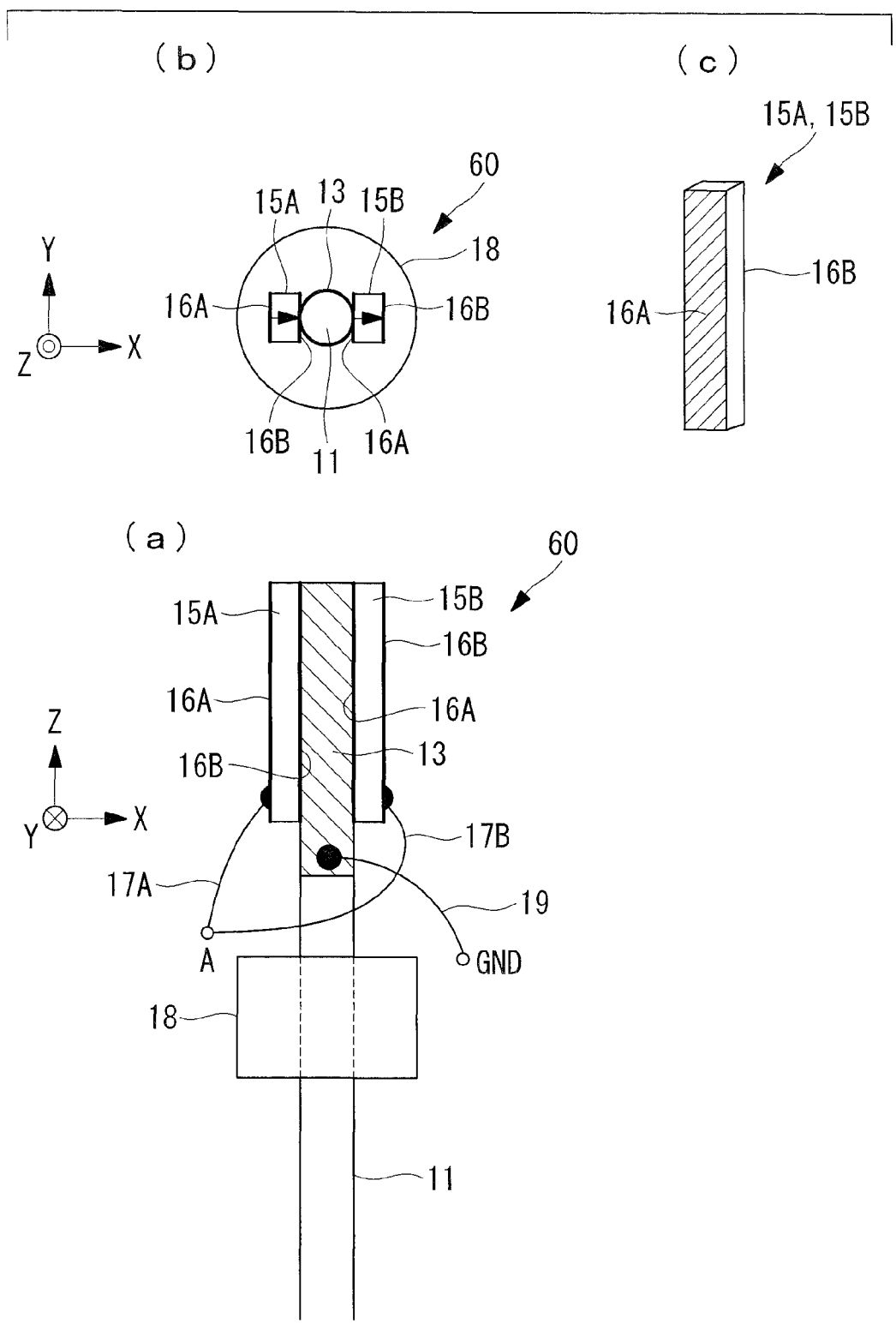
In FIG. 26, (a) is a diagram showing, in outline, the configuration of an optical fiber scanner according to a sixth embodiment of the present invention, viewed in a direction perpendicular to the longitudinal direction, (b) is a view of (a) in the longitudinal direction from the forward side of the optical fiber, and (c) is a perspective view in which only a piezoelectric element in (a) is picked out.

As shown in FIGS. 26(a) and (b), the optical fiber scanner 60 according to this embodiment differs from the fifth embodiment in that it is provided with a pair of piezoelectric elements that are disposed parallel to and opposing each other so as to flank the optical fiber 11 in a diameter direction thereof.

In the following, parts having the same configuration as those in the optical fiber scanner 50 according to the fifth embodiment are assigned the same reference signs and a description thereof will be omitted.

The pair of piezoelectric elements 15A and 15B are joined to the outer circumferential surface of the optical fiber 11 by using adhesives, with the conductive electrode 13 disposed therebetween. More specifically, the piezoelectric element 15A has its rear surface joined to the conductive electrode 13, and the piezoelectric element 15B has its front surface joined to the conductive electrode 13. Therefore, the polarization directions of the piezoelectric element 15A and the piezoelectric element 15B are the same direction as each other.

Also, on the pair of piezoelectric elements 15A and 15B, lead wires 17A and 17B are respectively joined to an electrode 16A or 16B on the surfaces thereof on the opposite sides from the surfaces that are joined to the conductive electrode 13, using conductive adhesive. These two lead wires 17A and 17B are joined together to constitute an A-phase. In addition, a single common GND line 19 is joined to the conductive electrode 13 with a conductive adhesive.

Figure 27:
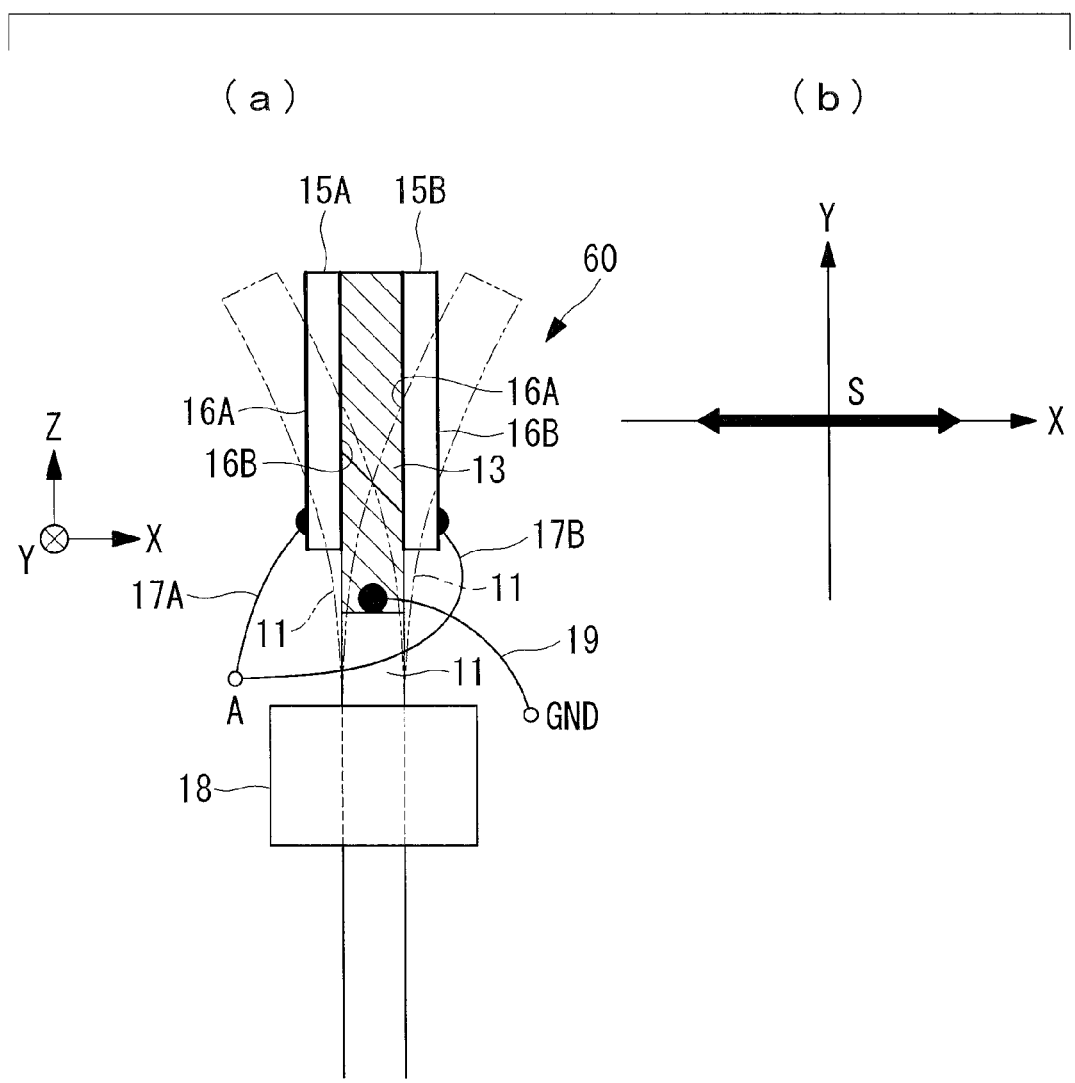
In FIG. 27, (a) is a diagram showing a state in which the distal end of the optical fiber in FIG. 26 is vibrated in the X direction, and (b) is a diagram showing the path traced out by the vibration of the distal end of the optical fiber in (a).

In the optical fiber scanner 60 according to this embodiment, when an alternating voltage corresponding to the frequency of the bending resonance vibration is applied to the A-phase of the pair of piezoelectric elements 15A and 15B via the lead wires 17A and 17B, the piezoelectric elements 15A and 15B together expand and contract in a direction perpendicular to the polarization directions, and thereby a bending resonance vibration is excited in the optical fiber 11, so that the distal end thereof vibrates in a direction intersecting the longitudinal direction (Z direction) thereof. Accordingly, as shown by the arrow S in FIG. 27(b), the distal end of the optical fiber 11 can be made to vibrate in the X direction.

As described above, with the optical fiber scanner 60 according to this embodiment, by using the two piezoelectric elements 15A and 15B, the vibration amplitude excited in the optical fiber 11 can be increased compared with the case where only a single piezoelectric element 15 is used.

Figure 28:
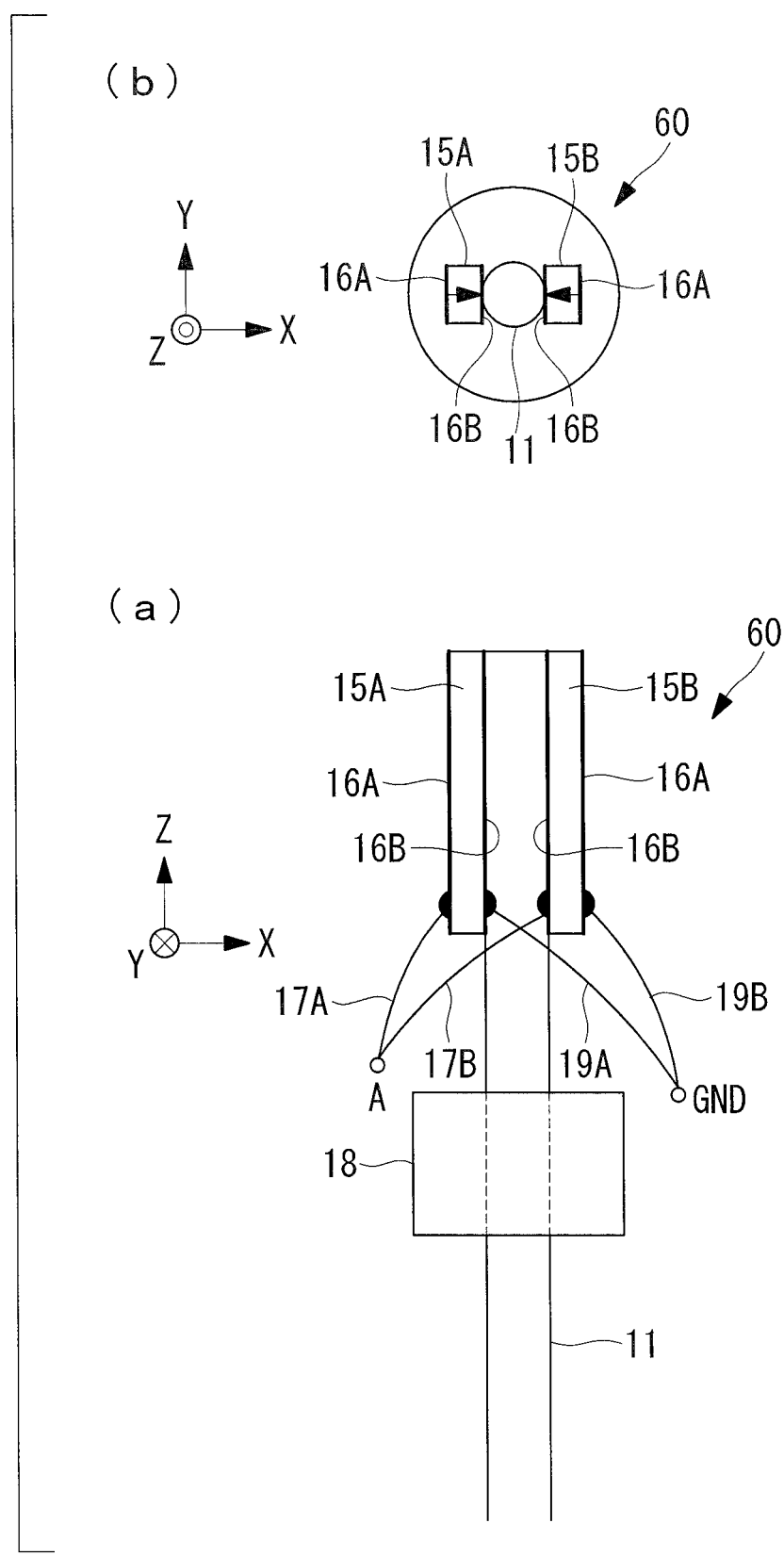
In FIG. 28, (a) is a diagram showing, in outline, the configuration of an optical fiber scanner according to a modification of the sixth embodiment of the present invention, viewed in a direction perpendicular to the longitudinal direction, and (b) is a view of the optical fiber in (a) in the longitudinal direction from the forward side thereof.

In this embodiment, as a first modification, similarly to the first modification of the fifth embodiment, the conductive electrode 13 may be eliminated, and the pair of piezoelectric elements 15A and 15B may be directly joined to the outer circumferential surface of the optical fiber 11. For example, FIGS. 28(a) and (b) show a state in which the rear surface of each of the piezoelectric elements 15A and 15B is joined to the outer circumferential surface of the optical fiber 11. The polarization directions (see arrows) of the piezoelectric elements 15A and 15B are different directions from each other, namely, directions pointing towards the optical fiber 11.

In this case, for example, on the piezoelectric element 15A, a common GND line 19A should be joined to the electrode 16B on the surface that is joined to the optical fiber 11 (rear surface), and the lead wire 17A should be joined to the electrode 16A on the surface at the opposite side (front surface). In addition, on the piezoelectric element 15B, the lead wire 17B should be joined to the electrode 16B on the surface that is joined to the optical fiber 11 (rear surface), and a common GND line 19B should be joined to the electrode 16A on the surface at the opposite side (front surface).

With this modification, it is possible to simplify the configuration by virtue of the omission of the conductive electrode 13.

Furthermore, in this embodiment and the modifications thereof, the conductive electrode 13 shown in the second to fourth modifications of the fifth embodiment may be employed, and the piezoelectric element 15 shown in the fifth modification of the fifth embodiment may be employed.

Seventh Embodiment

Next, an optical fiber scanner 70 according to a seventh embodiment of the present invention will be described below with reference to the drawings.

As shown in FIGS. 29(a) and (b), the optical fiber scanner 70 according to this embodiment differs from the sixth embodiment in that it is provided with another pair of piezoelectric elements 15C and 15D that are disposed so as to be shifted relative to the pair of piezoelectric elements 15A and 15B in the circumferential direction of the optical fiber 11.

In the following, parts having the same configuration as those in the optical fiber scanner 60 according to the sixth embodiment will be assigned the same reference signs, and a description thereof will be omitted.

Similarly to the pair of piezoelectric elements 15A and 15B, the pair of piezoelectric elements 15C and 15D are disposed parallel to and opposing each other so as to flank the optical fiber 11 in the diameter direction thereof and are joined to the outer circumferential surface of the optical fiber 11 by using adhesives, with a conductive electrode 13 disposed therebetween. In this embodiment, the rear surface of the piezoelectric element 15A and the front surface of the piezoelectric element 15B are joined to the conductive electrode 13, and the rear surface of the piezoelectric element 15C and the front surface of the piezoelectric element 15D are joined to the conductive electrode 13. Accordingly, the polarization directions of the piezoelectric element 15A and the piezoelectric element 15B are the same direction as each other, and the polarization directions of the piezoelectric element 15C and the piezoelectric element 15D are the same direction as each other.

Furthermore, the pair of piezoelectric elements 15A and 15B and the pair of piezoelectric elements 15C and 15D are disposed at positions that are shifted 90° in the circumferential direction of the optical fiber 11. For example, the pair of piezoelectric elements 15A and 15B are disposed so as to face each other in the X direction, and the pair of piezoelectric elements 15C and 15D are disposed so as to face each other in the Y direction. These four piezoelectric elements 15A, 15B, 15C, and 15D have width dimensions that are substantially equal to the diameter dimension of the optical fiber 11.

On the pair of piezoelectric elements 15A and 15B, using conductive adhesive, driving lead wires 17A and 17B constituting an A-phase are respectively joined to the electrode 16A or 16B on the surfaces that are on the opposite sides from the surfaces that are joined to the conductive electrode 13. On the pair of piezoelectric elements 15C and 15D, using conductive adhesive, driving lead wires 17C and 17D that constitute a B-phase are joined to the electrode 16A or 16B on the opposite sides from the surfaces that are joined to the conductive electrode 13. The common GND line 19 that is commonly provided for the four piezoelectric elements 15A, 15B, 15C, and 15D is joined to the conductive electrode 13 with conductive adhesive.

The operation of the thus-configured optical fiber scanner 70 will now be described.

Figure 30:
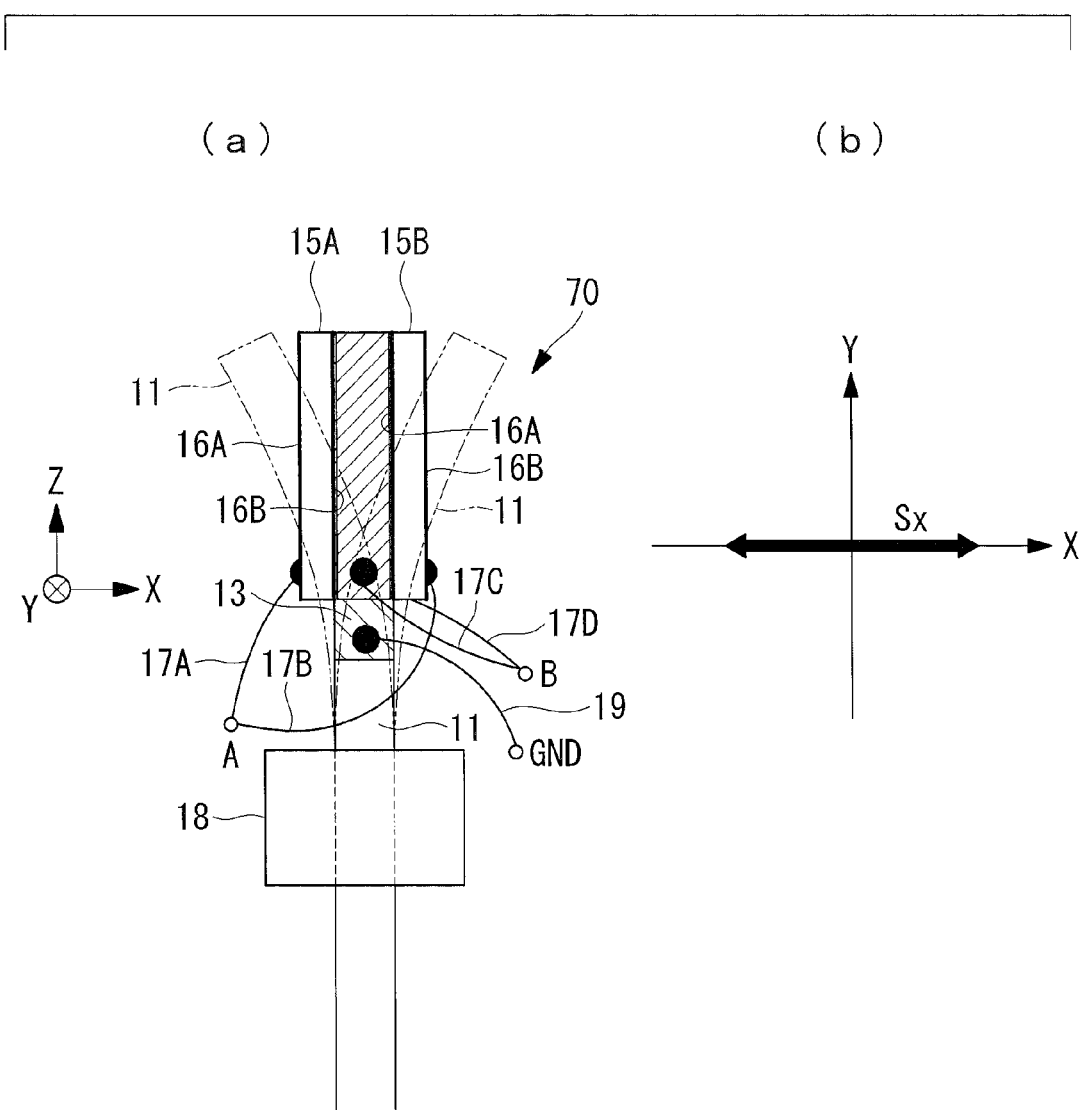
In FIG. 30, (a) is a diagram showing a state in which the distal end of the optical fiber in FIG. 29 is vibrated in the X direction, and (b) is a diagram showing the path traced out by the vibration of the distal end of the optical fiber in (a).

In the optical fiber scanner 70 according to this embodiment, when an alternating voltage corresponding to the frequency of a bending resonance vibration is applied to the A-phase of the pair of piezoelectric elements 15A and 15B via the lead wires 17A and 17B, the piezoelectric elements 15A and 15B together expand and contract in a direction perpendicular to the polarization directions thereof, and thereby, as shown in FIG. 30(a), the bending resonance vibration is excited in the optical fiber 11. In this bending resonance vibration, the vicinity of the ends at the base side of the piezoelectric elements 15A and 15B is a node, and the distal end of the optical fiber 11 is an antinode. Accordingly, as shown by the arrow Sx in FIG. 30(b), the distal end of the optical fiber 11 can be made to vibrate in a linear fashion in the X direction.

Figure 31:
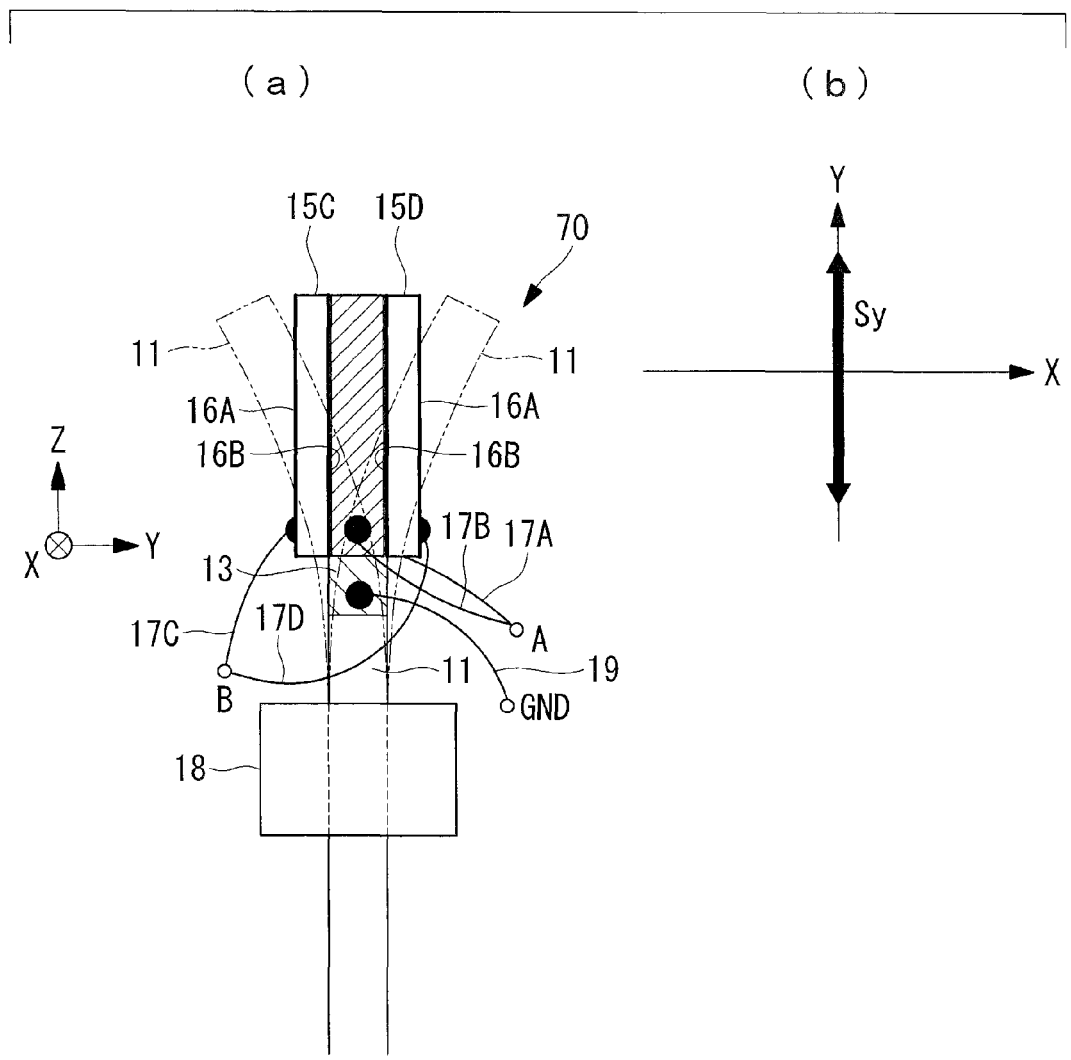
In FIG. 31, (a) is a diagram showing a state in which the distal end of the optical fiber in FIG. 29 is vibrated in the Y direction, and (b) is a diagram showing the path traced out by the vibration of the distal end of the optical fiber in (a).

On the other hand, when an alternating voltage corresponding to the frequency of the bending resonance vibration is applied in the thickness direction to the B-phase of the pair of piezoelectric elements 15C and 15D via the lead wires 17C and 17D, the piezoelectric elements 15C and 15D together expand and contract in a direction perpendicular to the polarization directions thereof, and thereby, as shown in FIG. 31(a), a bending resonance vibration is excited in the optical fiber 11. In this bending resonance vibration, the vicinity of the ends at the base side of the piezoelectric elements 15C and 15D is a node, and the distal end of the optical fiber 11 is an antinode. Accordingly, as shown by arrow Sy in FIG. 31(b), the distal end of the optical fiber 11 can be vibrated in a linear fashion in the Y direction.

Figure 32:
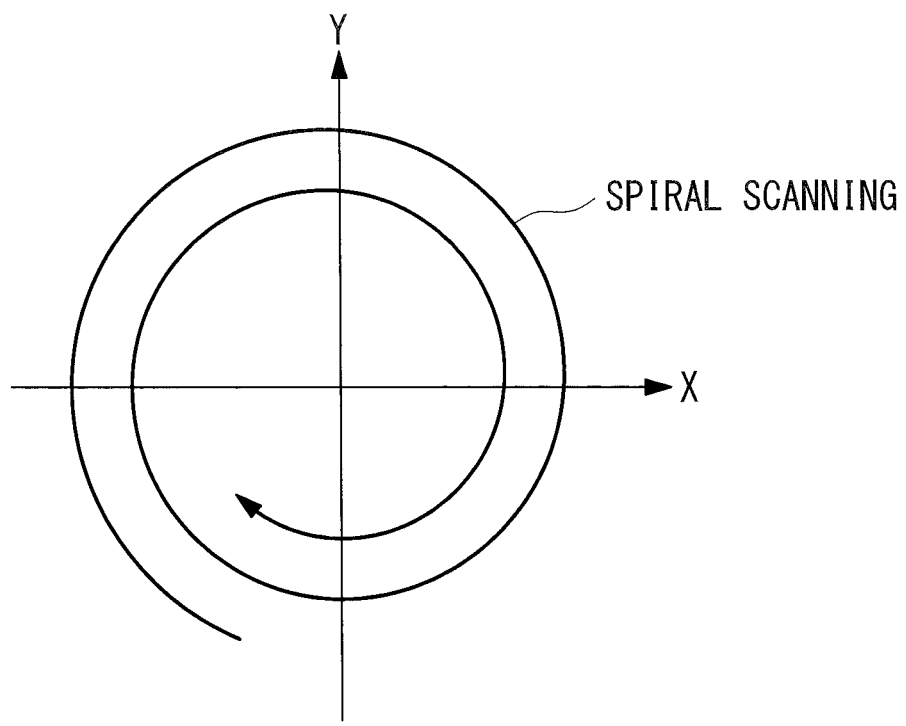
FIG. 32 is a diagram showing spiral scanning of the distal end of the optical fiber.

Thus, when the X-direction vibration and the Y-direction vibration are simultaneously generated in the optical fiber 11, and the phase of the alternating voltage applied to the piezoelectric elements 15A and 15B and the phase of the alternating voltage applied to the piezoelectric elements 15C and 15D are shifted by $\pi/2$, the distal end of the optical fiber 11 vibrates along a circular path. Then, when the amplitudes of the two alternating voltages during this process are temporally varied in a sinusoidal shape, as shown in FIG. 32, the distal end of the optical fiber 11 vibrates along a spiral path (spiral scanning). Accordingly, the illumination light can be two-dimensionally scanned along a spiral path (spiral scanning) on the subject.

In this case, with this embodiment, since the piezoelectric elements 15A, 15B, 15C, and 15D are disposed also at the distal end of the optical fiber 11, the distal end of the optical fiber 11 is forcibly vibrated in the X direction and the Y direction so as to accurately follow the expansion and contraction motion of the piezoelectric elements 15A, 15B, 15C, and 15D. Accordingly, the distal end of the optical fiber 11 is made to vibrate along the intended spiral path, and as a result, the illumination light can be two-dimensionally scanned along the intended spiral path on the subject X.

Figure 33:
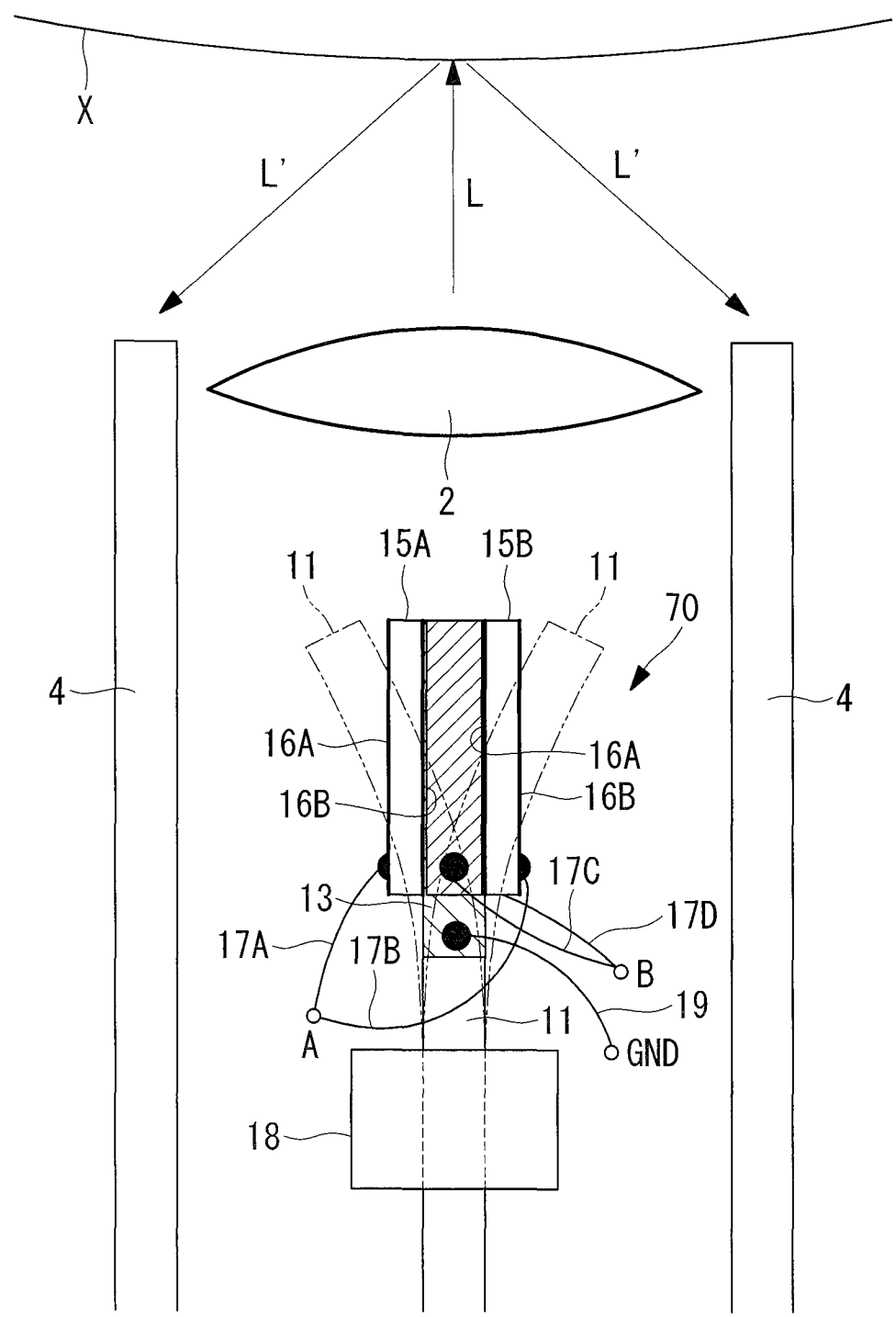
FIG. 33 is a diagram showing the application of the optical fiber scanner in FIG. 29 to a scanning-type observation apparatus.

Next, a case in which the optical fiber scanner 70 according to this embodiment is employed in a scanning-type observation apparatus will be described. FIG. 33 shows part of the configuration of a scanning-type observation apparatus provided with the optical scanner 70. This scanning-type observation apparatus includes a lens 2 disposed at the forward side of the optical fiber scanner 70 and a plurality of detection fibers 4 arrayed in the circumferential direction at the outer side of the optical fiber 11.

As shown in FIG. 33, with the lens 2 being disposed so as to face the subject X, when the distal end of the optical fiber 11 is made to vibrate in a spiral fashion, and the illumination light L that has propagated inside the optical fiber 11 emerges from the distal end, the illumination light L is focused by the lens 2, is radiated onto the subject X, and is two-dimensionally scanned on the subject X.

Reflected light L' from the subject X irradiated with the illumination light L is detected by the plurality of detection fibers 4. The scanning-type observation apparatus can form an image of the surface state of a scanning region of the illumination light L on the subject X by detecting the reflected light L' using the detection fibers 4 in synchronization with the scanning period of the illumination light L. In this case, since the illumination light L is scanned over an ideal, intended spiral path on the subject X, it is possible to obtain a distortion-free image.

This embodiment can be modified in the following ways.

Figure 34:
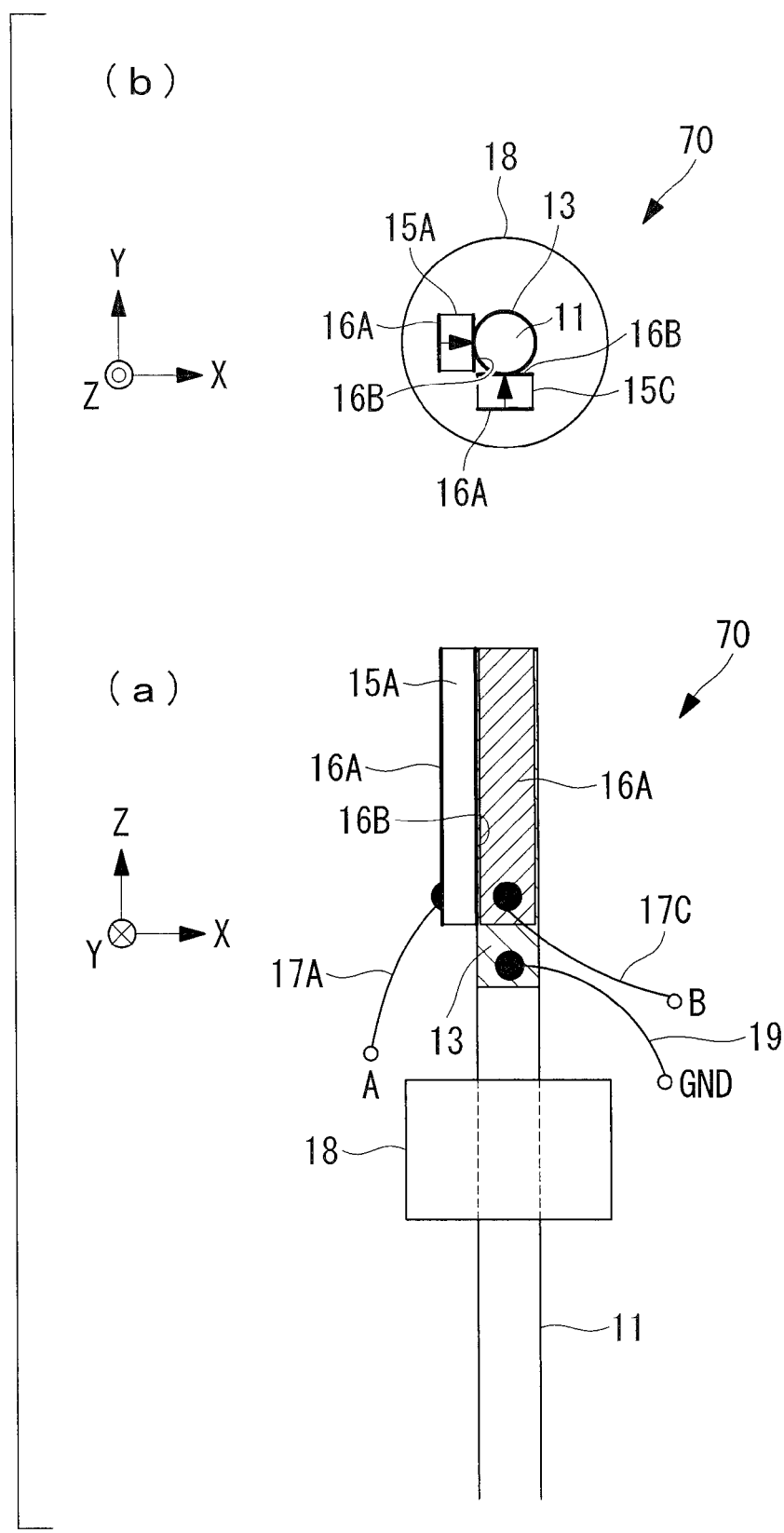
In FIG. 34, (a) is a diagram showing, in outline, the configuration of an optical fiber scanner according to a first modification of the seventh embodiment of the present invention, viewed in a direction perpendicular to the longitudinal direction, and (b) is a view of the optical fiber in (a) in the longitudinal direction from the forward side thereof.

As a first modification, instead of providing the four piezoelectric elements 15A, 15B, 15C, and 15D, as shown in FIGS. 34(a) and (b), the two piezoelectric elements 15A and 15C may be provided. The piezoelectric elements 15A and 15C are disposed at positions shifted by 90° in the circumferential direction of the optical fiber 11 so that their polarization directions are oriented perpendicular to each other.

With this modification, by applying alternating voltages to the two piezoelectric elements 15A and 15C with phases that are shifted by $\pi/2$, the distal end of the optical fiber 11 can be vibrated in a spiral fashion, and thus, it is possible to two-dimensionally scan the illumination light on the subject. Therefore, the configuration can be simplified compared with the case in which the four piezoelectric elements 15A, 15B, 15C, and 15D are used.

Figure 35:
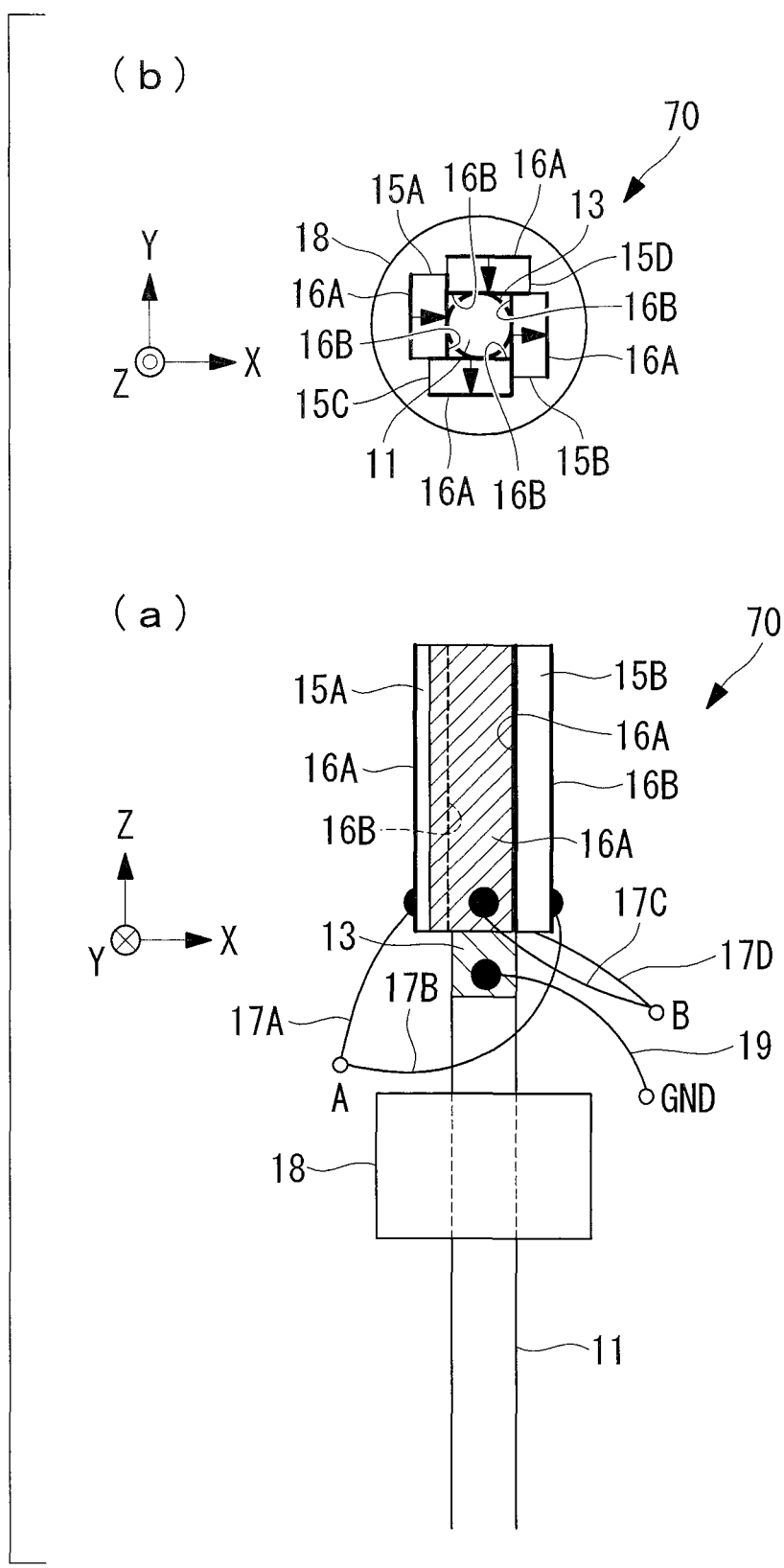
In FIG. 35, (a) is a diagram showing, in outline, the configuration of an optical fiber scanner according to a second modification of the seventh embodiment of the present invention, viewed in a direction perpendicular to the longitudinal direction, and (b) is a view of the optical fiber in (a) in the longitudinal direction from the forward side thereof.

As a second modification, as shown in FIGS. 35(a) and (b), the width dimension of each of the piezoelectric elements 15A, 15B, 15C, and 15D may be larger than the diameter dimension of the optical fiber 11. In this case, as shown in the same figure, each of the piezoelectric elements 15A, 15B, 15C, and 15D should be joined to the optical fiber 11 so as to be slightly shifted in the width direction thereof, so that either the front surfaces or rear surfaces and the side surfaces of neighboring piezoelectric elements 15A, 15B, 15C, and 15D in the circumferential direction of the optical fiber 11 are alternately in contact.

With this modification, the four piezoelectric elements 15A, 15B, 15C, and 15D can be positioned relative to each other in the circumferential direction of the optical fiber 11, thus simplifying assembly. In addition, the effective volumes of the piezoelectric elements 15A, 15B, 15C, and 15D are increased, and therefore, the amount of displacement in the expansion and contraction of the piezoelectric elements 15A, 15B, 15C, and 15D can be increased by inputting more energy thereto, and it is thus possible to increase the vibration amplitude of the optical fiber 11.

Figure 36:
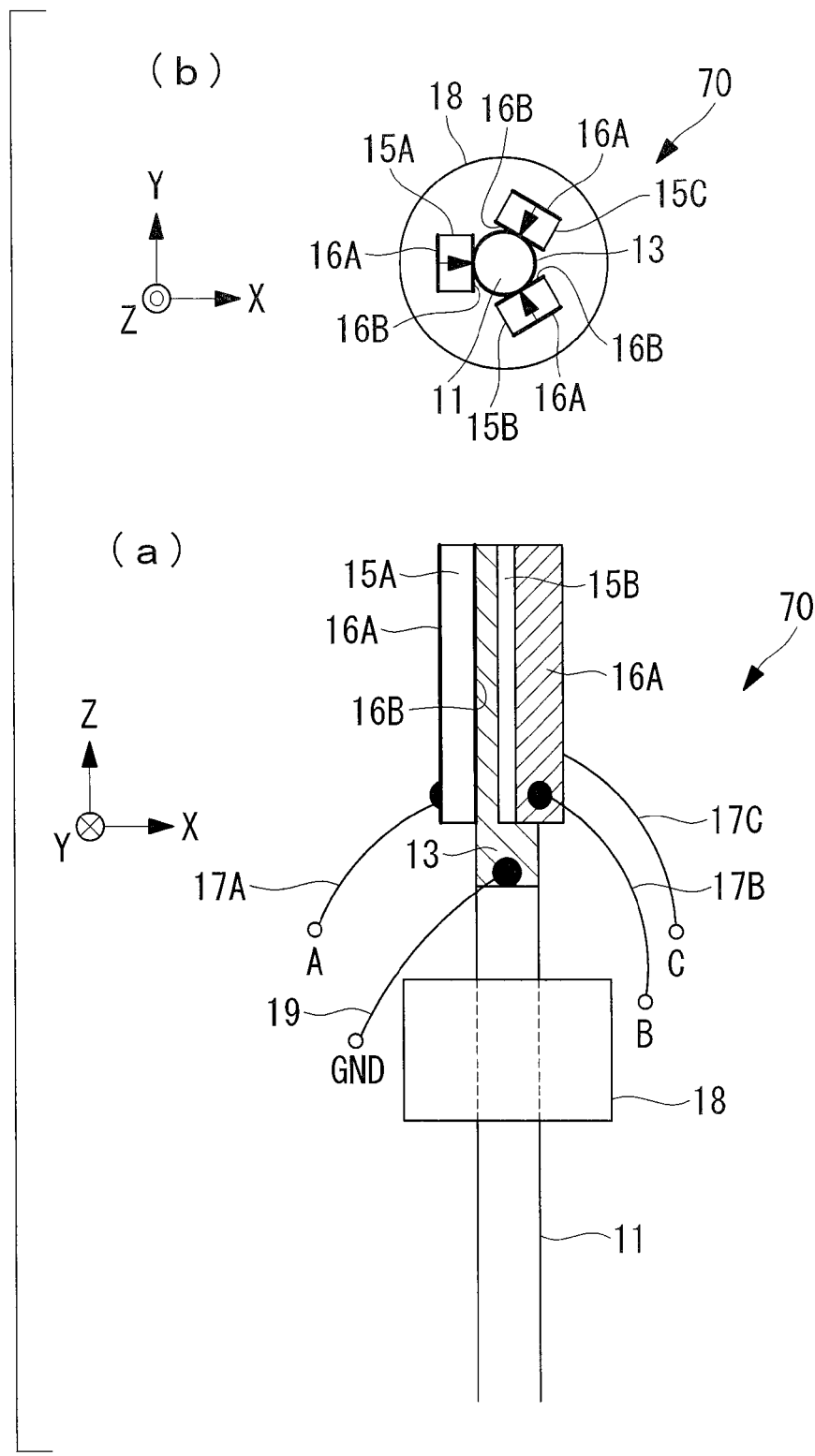
In FIG. 36, (a) is a diagram showing, in outline, the configuration of an optical fiber scanner according to a third modification of the seventh embodiment of the present invention, viewed in a direction perpendicular to the longitudinal direction thereof, and (b) is a view of the optical fiber in (a) in the longitudinal direction from the forward side thereof.

As a third modification, as shown in FIGS. 36(a) and (b), three piezoelectric elements 15A, 15B, and 15C may be disposed at positions 120° apart in the circumferential direction of the optical fiber 11 and joined thereto. In this case, the piezoelectric elements 15A, 15B, and 15C have their polarization directions pointing towards the optical fiber 11 and are joined to the conductive electrode 13 at the rear surfaces thereof. Also, driving lead wires 17A, 17B, and 17C that respectively constitute an A-phase, a B-phase, and a C-phase are joined to the electrodes 16A on surfaces (front surfaces) at the opposite sides from the surfaces of the piezoelectric elements 15A, 15B, and 15C that are joined to the conductive electrode 13, by using a conductive adhesive.

Thus, alternating voltages that are electrically shifted in phase by 120° from each other should be applied to the A-phase of the piezoelectric element 15A, the B-phase of the piezoelectric element 15B, and the C-phase of the piezoelectric element 15C. By doing so, the number of piezoelectric elements is reduced from 4 to 3, the distal end of the optical fiber 11 can be vibrated in a spiral manner, and thus the illumination light can be two-dimensionally scanned on the subject.

Figure 37:
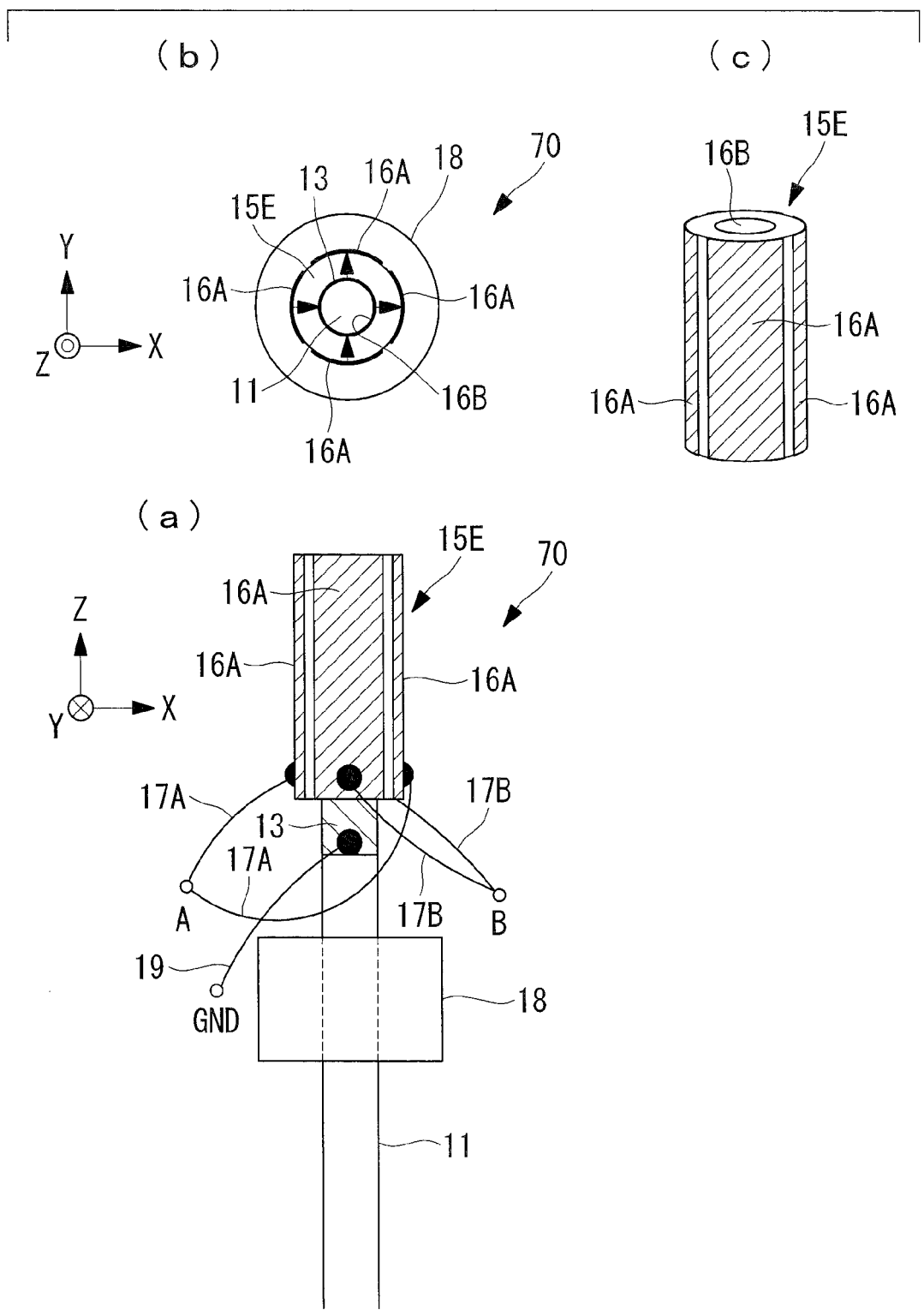
In FIG. 37, (a) is a diagram showing, in outline, the configuration of an optical fiber scanner according to a fourth modification of the seventh embodiment of the present invention, viewed in a direction perpendicular to the longitudinal direction thereof, (b) is a view of the optical fiber in (a) in the longitudinal direction from the forward side thereof, and (c) is a perspective view in which only a piezoelectric element in (a) is picked out.

As a fourth modification, as shown in FIGS. 37(a) and (b), a cylindrical piezoelectric element 15E may be used. This cylindrical piezoelectric element 15E has an inner diameter that is substantially the same as the outer diameter of the optical fiber 11. Four electrodes 16A that are arranged substantially uniformly in the circumferential direction are provided on the outer circumferential surface of the piezoelectric element 15E. Similarly, an electrode 16B is provided on the inner circumferential surface of the piezoelectric element 15E.

With this modification, even though the piezoelectric element 15E, which is formed of a single member, is used, similarly to the case in which the four piezoelectric elements 15A, 15B, 15C, and 15D are provided as separate elements, it is possible to vibrate the distal end of the optical fiber 11 in a spiral fashion. In addition, by forming the piezoelectric element 15E of a single member in this way, assembly can be simplified.

Figure 38:
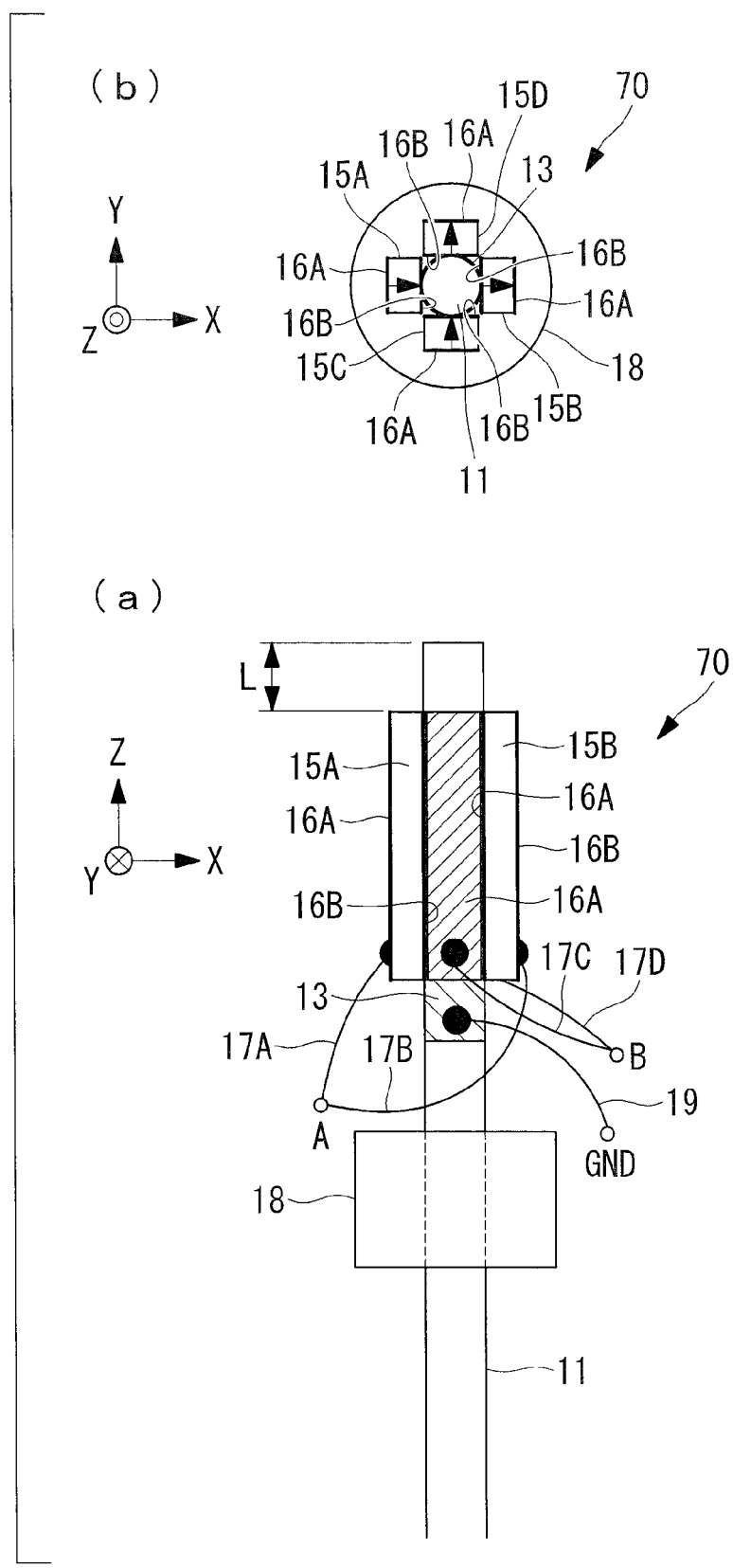
In FIG. 38, (a) is a diagram showing, in outline, the configuration of an optical fiber scanner according to a fifth modification of the seventh embodiment of the present invention, viewed in a direction perpendicular to the longitudinal direction, and (b) is a view of the optical fiber in (a) in the longitudinal direction from the forward side thereof.

As a fifth modification, as shown in FIGS. 38(a) and (b), the distal ends of the piezoelectric elements 15A, 15B, 15C, and 15D may be disposed at positions that are set back by distance L towards the base side from the distal end of the optical fiber 11. However, this distance L is set in such a range that the resonance frequency of the first-order bending vibration mode, in which one end serves as a fixed end, of the distal end portion of the optical fiber 11 of length L, which projects farther than the piezoelectric elements 15A, 15B, 15C, and 15D, is higher than the frequency of the alternating voltage for exciting a bending resonance vibration in the optical fiber 11.

Figure 29:
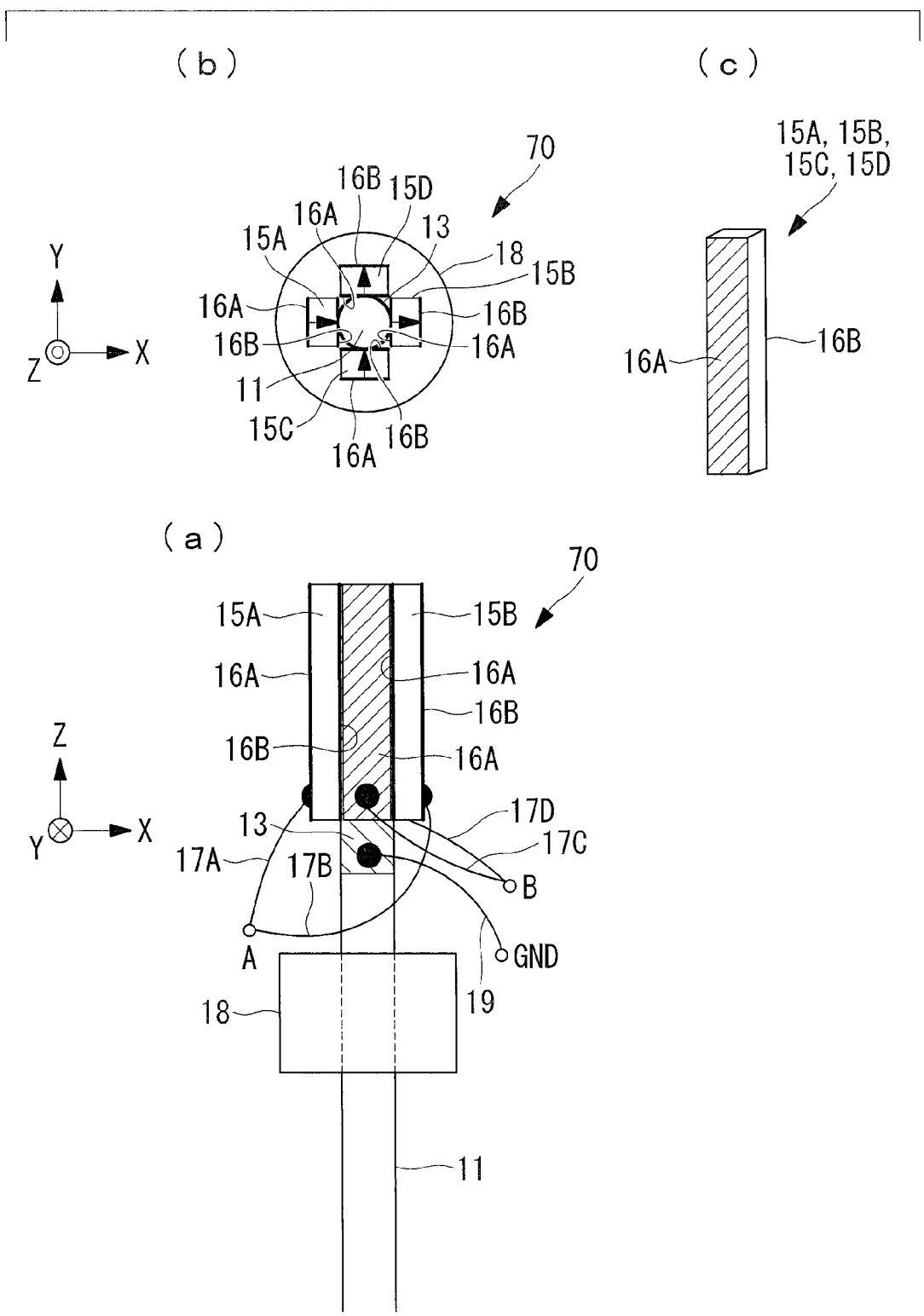
In FIG. 29, (a) is a diagram showing, in outline, the configuration of an optical fiber scanner according to a seventh embodiment of the present invention, viewed in a direction perpendicular to the longitudinal direction, (b) is a view of (a) in the longitudinal direction from the forward side of the optical fiber, and (c) is a perspective view in which only a piezoelectric element in (a) is picked out.

When the distance L is within the above-described range, when an alternating voltage is applied to cause the optical fiber 11 to undergo a bending resonance vibration, the part of the optical fiber 11 that projects from the piezoelectric elements 15A, 15B, 15C, and 15D does not have any influence on the bending resonance vibration, and the distal end of the optical fiber 11 vibrates along the intended spiral path, similarly to when the piezoelectric elements 15A, 15B, 15C, and 15D are disposed as shown in FIG. 29.

With this modification, by not providing the piezoelectric elements 15A, 15B, 15C, and 15D at the distal end of the optical fiber 11 where the amplitude is greatest, the optical fiber scanner 70 can prevent interference in other members located therearound, for example, the detection fibers 4 in FIG. 33. In addition, design restrictions and the positioning precision required during assembly of the piezoelectric elements 15A, 15B, 15C, and 15D used can be relaxed.

Figure 39:
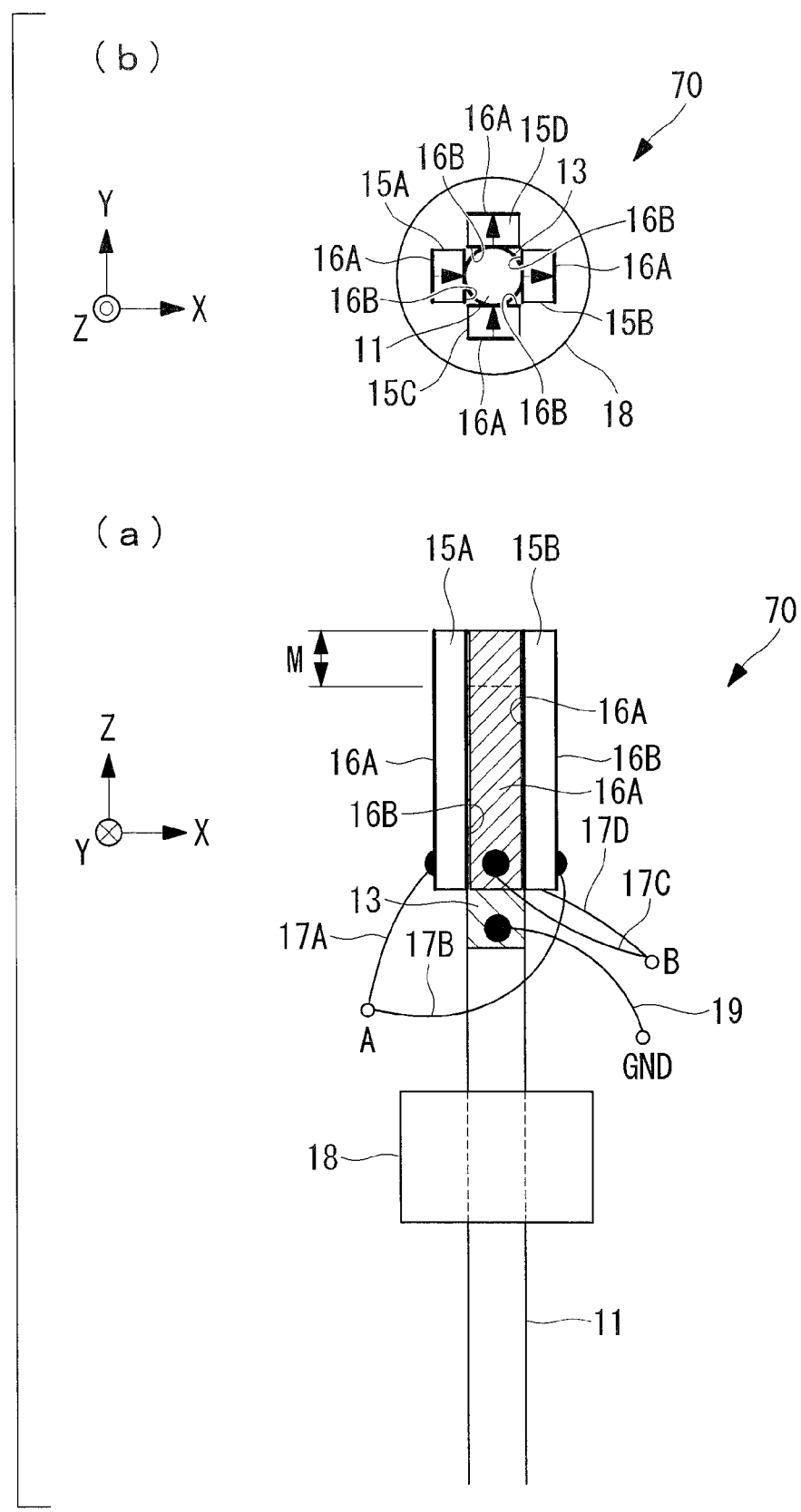
In FIG. 39, (a) is a diagram showing, in outline, the configuration of an optical fiber scanner according to a sixth modification of the seventh embodiment of the present invention, viewed in a direction perpendicular to the longitudinal direction, and (b) is a view of the optical fiber in (a) in the longitudinal direction from the forward side thereof.

As a sixth modification, as shown in FIGS. 39(a) and (b), the distal ends of the piezoelectric elements 15A, 15B, 15C, and 15D may be disposed at positions at which they protrude towards the forward side by distance M from the distal end of the optical fiber 11. However, this distance M is set in such a range that the resonance frequency of the first-order bending vibration mode, in which one end serves as a fixed end, of the distal end portions of the piezoelectric elements 15A, 15B, 15C, and 15D of length M, which project from the distal end of the optical fiber 11, is higher than the frequency of the alternating voltage for exciting a bending resonance vibration in the optical fiber 11.

When the distance M is within the above-described range, when an alternating voltage is applied to cause the optical fiber 11 to undergo a bending resonance vibration, the parts of the piezoelectric elements 15A, 15B, 15C, and 15D that project from the optical fiber 11 do not have any influence on the bending resonance vibration, and the distal end of the optical fiber 11 vibrates along the intended spiral path, similarly to when the piezoelectric elements 15A, 15B, 15C, and 15D are disposed as shown in FIG. 29.

With this modification, design restrictions and the positional precision required during assembly of the piezoelectric elements 15A, 15B, 15C, and 15D used can be relaxed.

Furthermore, in this embodiment and the modifications thereof, the conductive electrode 13 shown in the first to fourth modifications of the fifth embodiment may be employed, and the piezoelectric element shown in the fifth modification of the fifth embodiment may be employed.

Although the embodiments of the present invention have been described above with reference to the drawings, the specific configuration is not limited thereto, and design modifications that do not depart from the scope of the present invention are also encompassed. For example, the present invention is not limited to the above-described embodiments and modification and may be applied to embodiments in which these embodiments and modifications are suitably combined, without particular limitation.

The above-described embodiment leads to the following inventions.

A first aspect of the present invention is an optical fiber scanner including an elongated optical fiber in which illumination light is guided and can emerge from a distal end thereof; and at least one piezoelectric element having a plate shape polarized in a thickness direction thereof and being individually bonded to an outer circumferential surface of the optical fiber closer to a base side than to the distal end thereof.

According to the first aspect, when an alternating voltage is applied to the piezoelectric elements in the thickness direction thereof, the piezoelectric elements expand and contract in a direction perpendicular to the polarization directions thereof, in other words, in a direction perpendicular to the thickness directions, and thereby, a bending vibration is excited in the optical fiber so that the distal end thereof vibrates in a direction intersecting the longitudinal direction. Accordingly, the illumination light emerging from the distal end of the optical fiber can be scanned on the subject in association with the vibration of the distal end.

In this case, by separately bonding the plate-shaped piezoelectric elements to the outer circumferential surface of the optical fiber, the individual piezoelectric elements can be adhered to the outer circumferential surface of the optical fiber with superior precision. Accordingly, the expansion and contraction of the piezoelectric elements can be transferred to the optical fiber with high efficiency, and the optical fiber can be made to undergo a large bending vibration. In addition, by directly bonding the piezoelectric elements to the outer circumferential surface of the optical fiber, the force from the piezoelectric elements can be directly transferred to the optical fiber. Accordingly, attenuation of the force, as in the case where a resin material is interposed between the optical fiber and the piezoelectric elements, can be avoided, and therefore, the bending vibration of the optical fiber can be made even larger.

In the first aspect, the piezoelectric element may be bonded to the outer circumferential surface of the optical fiber over the entire length thereof.

With this configuration, the expansion and contraction can be losslessly transferred to the optical fiber over the entire length of the piezoelectric element.

In the first aspect, two of the piezoelectric elements, which are disposed at positions shifted in the circumferential direction of the optical fiber so that the polarization directions intersect each other, may be provided.

With this configuration, by applying alternating voltages to the individual piezoelectric elements with suitable phase shifts therebetween, the distal end of the optical fiber can be made to vibrate in a spiral fashion, and the illumination light can be scanned two-dimensionally.

In the first aspect, the two piezoelectric elements may be disposed at shifted positions so as not to overlap in the longitudinal direction of the optical fiber.

With this configuration, since the piezoelectric elements do not overlap in the circumferential direction and the longitudinal direction of the optical fiber, it is possible to use large-volume, wide piezoelectric elements without increasing the overall size of the scanner. Accordingly, a larger energy can be output from the piezoelectric elements, and the optical fiber can be made to vibrate with a large amplitude.

In the first aspect, a pair of the piezoelectric elements, which are disposed parallel to and opposing each other so as to flank the optical fiber, may be provided.

With this configuration, by making the pair of piezoelectric elements expand and contract in the same direction, the bending vibration excited in the optical fiber can be increased compared with a case in which there is only one piezoelectric element.

In the first aspect, another pair of the piezoelectric elements, which are disposed so as to be shifted in the circumferential direction of the optical fiber relative to the pair of piezoelectric elements and which are disposed parallel to and opposing each other so as to flank the optical fiber, may be provided.

With this configuration, by applying alternating voltages to the individual piezoelectric elements with suitable phase shifts therebetween, the distal end of the optical fiber can be made to vibrate in a spiral fashion, and the illumination light can be scanned two-dimensionally.

In the first aspect, the pair of piezoelectric elements may be disposed at shifted positions so as not to overlap in the longitudinal direction of the optical fiber.

With this configuration, compared with a case where there are two piezoelectric elements, a higher energy can be output to each pair of piezoelectric elements, and the optical fiber can be vibrated with a larger amplitude.

In the first aspect, three or more of the piezoelectric elements, which are arranged in the circumferential direction of the optical fiber with substantially equal gaps therebetween, may be provided.

With this configuration, by applying alternating voltages to the individual piezoelectric elements with suitable phase shifts therebetween, the distal end of the optical fiber can be made to vibrate in a spiral fashion, and the illumination light can be scanned two-dimensionally.

A second aspect of the present invention is an optical fiber scanner including an elongated optical fiber in which illumination light is guided and can emerge from a distal end thereof; and a piezoelectric element which has a plate shape polarized in a thickness direction thereof and which is bonded to an outer circumferential surface of the optical fiber at a position including the distal end of the optical fiber or the vicinity thereof and so that the thickness direction thereof points in a direction intersecting the longitudinal direction of the optical fiber.

According to the second aspect, when an alternating voltage is applied to the piezoelectric element in the thickness direction thereof, the piezoelectric element expands and contracts in a direction perpendicular to the polarization direction, in other words, in a direction perpendicular to the thickness direction, and thereby, a bending vibration is excited in the optical fiber so that the distal end thereof vibrates in a direction intersecting the longitudinal direction. Accordingly, the illumination light emerging from the distal end of the optical fiber can be scanned on the subject in association with the vibration of the distal end.

In this case, since the piezoelectric element is disposed at a position including the distal end of the optical fiber or the vicinity thereof, the distal end of the optical fiber is forcedly vibrated in a direction intersecting the expansion and contraction direction so as to accurately follow the expansion and contraction motion of the piezoelectric element. Accordingly, the distal end of the optical fiber vibrates along the intended path, and therefore, the illumination light emerging from the distal end of the optical fiber can be scanned along the intended path.

In the second aspect, a pair of the piezoelectric elements, which are disposed parallel to and opposing each other so as to flank the optical fiber in the diameter direction thereof, may be provided.

With this configuration, by causing the pair of piezoelectric elements to expand and contract in the same direction, the bending vibration excited in the optical fiber can be increased compared with a case where there is only one piezoelectric element.

In the second aspect, another pair of the piezoelectric elements, which are disposed parallel to and opposing each other so as to flank the optical fiber, may be provided at positions that are shifted by substantially 90° in the circumferential direction of the optical fiber relative to the pair of piezoelectric elements.

With this configuration, by applying alternating voltages to the individual piezoelectric elements with suitable phase shifts therebetween, the distal end of the optical fiber can be made to vibrate in a spiral fashion, and the illumination light can be scanned two-dimensionally.

In the second aspect, three or more of the piezoelectric elements, which are arranged in the circumferential direction of the optical fiber, may be provided.

With this configuration, by applying alternating voltages to the individual piezoelectric elements with suitable phase shifts therebetween, the distal end of the optical fiber can be made to vibrate in a spiral fashion, and the illumination light can be scanned two-dimensionally.

In the second aspect, the piezoelectric elements may be disposed at positions set back from the distal end of the optical fiber towards the base side of the optical fiber, and the distance between the distal ends of the piezoelectric elements and the distal end of the optical fiber may be set so that the frequency of a bending resonance vibration, in which one end serves as a fixed end, of a distal end portion of the optical fiber that protrudes farther towards the forward side than the piezoelectric elements do is higher than a frequency of an alternating voltage supplied to the piezoelectric elements for exciting a bending vibration in the optical fiber.

With this configuration, by not providing the piezoelectric elements at the distal end of the optical fiber, where the vibration amplitude is highest, it is possible to prevent the distal end of the optical fiber from interfering with members in the surroundings. In addition, the precision requirements, such as the shapes of the piezoelectric elements and their positioning precision on the optical fiber, can be relaxed. And even if the piezoelectric elements are disposed at positions set back from the distal end of the optical fiber, by setting the amount of set-back to the above-described range, the distal end of the optical fiber can be made to vibrate without being affected by shifts in the positions of the piezoelectric elements.

In the second aspect, the piezoelectric elements may be disposed at positions where the piezoelectric elements protrude farther towards the forward side of the optical fiber than the distal end of the optical fiber does, and the distance between the distal end of the piezoelectric elements and the distal end of the optical fiber may be set so that the frequency of a bending resonance vibration, in which one end serves as a fixed end, of distal end portions of the piezoelectric elements that protrude farther towards the forward side than the distal end of the optical fiber does is higher than a frequency of an alternating voltage supplied to the piezoelectric elements for exciting a bending vibration in the optical fiber.

With this configuration, the precision requirements, such as the shapes of the piezoelectric elements and their positioning precision on the optical fiber, can be relaxed. And even if the piezoelectric elements are disposed at positions where they protrude from the distal end of the optical fiber, by setting the amount of this protrusion to the above-described range, the distal end of the optical fiber can be made to vibrate without being affected by shifts in the position of the piezoelectric elements.

In the second aspect, the piezoelectric element may be a stacked-type piezoelectric element in which a plurality of piezoelectric layers are stacked in the thickness direction thereof.

By doing so, the amount of variation in the expansion and contraction of the piezoelectric elements when alternating voltages of the same magnitude are applied to the piezoelectric elements is increased, and therefore, it is possible to increase the vibration amplitude of the distal end of the optical fiber.

The first and second aspects may further include a conductive electrode member that is disposed between the outer circumferential surface of the optical fiber and the piezoelectric element.

With this configuration, using the electrode member as a GND electrode and joining a GND line to this electrode member simplifies the routing of the GND line. In particular, in a configuration provided with a plurality of electrode members, by using an electrode member as a common GND electrode, it is possible to effectively simplify the routing of the GND line.

REFERENCE SIGNS LIST 10, 20, 30, 40, 50, 60, 70 optical fiber scanner
11 optical fiber
13 conductive electrode (electrode member)
15, 15A, 15B, 15C, 15D, 15E piezoelectric element

The invention claimed is:

1. An optical fiber scanner comprising:
   an elongated optical fiber in which illumination light is guided and can emerge from a distal end of the optical fiber;
   a first pair of piezoelectric elements disposed parallel to and opposing each other so as to flank the optical fiber with their inner surfaces; and
   a second pair of piezoelectric elements disposed so as to be shifted in a circumferential direction of the optical fiber relative to the first pair of piezoelectric elements, the second pair of piezoelectric elements being disposed parallel to and opposing each other so as to flank the optical fiber with their inner surfaces;
   wherein:
   each of the first pair of piezoelectric elements and each of the second pair of piezoelectric elements have a plate shape polarized in a thickness direction of the plate shape and each of the first pair of piezoelectric elements and each of the second pair of piezoelectric elements are individually bonded to an outer circumferential surface of the optical fiber closer to a base side than to the distal end;
   a width dimension of each of the first pair of piezoelectric elements and the second pair of piezoelectric elements is larger than a diameter dimension of the optical fiber; and
   each of the first pair of piezoelectric elements and the second pair of piezoelectric elements is shifted in a width direction such that an inner surface of each of the first pair of piezoelectric elements directly contacts a side surface of a corresponding one of the second pair of piezoelectric elements and an inner surface of each of the second pair of piezoelectric elements directly contacts a side surface of a corresponding one of the first pair of piezoelectric elements.

2. An optical fiber scanner according to claim 1, wherein the first pair of piezoelectric elements and the second pair of piezoelectric elements are disposed at shifted positions so as not to overlap in the longitudinal direction of the optical fiber.

3. An optical fiber scanner according to claim 1, wherein each of the first pair of piezoelectric elements and each of the second pair of piezoelectric elements are individually bonded to the outer circumferential surface of the optical fiber over an entire length thereof.

4. An optical fiber scanner according to claim 1, further comprising an electrode provided on an outer circumferential surface of the optical fiber and to which a ground line for the first pair of piezoelectric elements and the second pair of piezoelectric elements is joined.

5. An optical fiber scanner according to claim 4, wherein the ground line is disposed closer to a base end of the optical fiber than the first pair of piezoelectric elements and the second pair of piezoelectric elements are.

6. An optical fiber scanner comprising:
an elongated optical fiber in which illumination light is guided and can emerge from a distal end of the optical fiber;
a first pair of piezoelectric elements disposed parallel to and opposing each other so as to flank the optical fiber with their inner surfaces; and
a second pair of piezoelectric elements disposed so as to be shifted in a circumferential direction of the optical fiber relative to the first pair of piezoelectric elements, the second pair of piezoelectric elements being disposed parallel to and opposing each other so as to flank the optical fiber with their inner surfaces;
wherein:
each of the first pair of piezoelectric elements and each of the second pair of piezoelectric elements have a plate shape polarized in a thickness direction of the plate shape and each of the first pair of piezoelectric elements and each of the second pair of piezoelectric elements are individually bonded to an outer circumferential surface of the optical fiber at a distal end portion of the optical fiber and the thickness direction points in a direction intersecting the longitudinal direction of the optical fiber;
a width dimension of each of the first pair of piezoelectric elements and the second pair of piezoelectric elements is larger than a diameter dimension of the optical fiber; and
each of the first pair of piezoelectric elements and the second pair of piezoelectric elements is shifted in a width direction such that an inner surface of each of the first pair of piezoelectric elements directly contacts a side surface of a corresponding one of the second pair of piezoelectric elements and an inner surface of each of the second pair of piezoelectric elements directly contacts a side surface of a corresponding one of the first pair of piezoelectric elements.

7. An optical fiber scanner according to claim 6, wherein the second pair of piezoelectric elements are provided at positions that are shifted by substantially 90° in the circumferential direction of the optical fiber relative to the first pair of piezoelectric elements.

8. An optical fiber scanner according to claim 6, wherein the first and second pairs of piezoelectric elements are disposed at positions set back from the distal end of the optical fiber toward the base side of the optical fiber, and
a distance between the distal ends of the first and second pairs of piezoelectric elements and the distal end of the optical fiber is set so that a frequency of a bending resonance vibration, in which one end serves as a fixed end, of the distal end portion of the optical fiber that protrudes farther towards a distal end side than the first and second pairs of piezoelectric elements protrude is higher than a frequency of an alternating voltage supplied to the first and second pairs of piezoelectric elements for exciting a bending vibration in the optical fiber.

9. An optical fiber scanner according to claim 6, wherein the first and second pairs of piezoelectric elements are disposed at positions where the first and second pairs of piezoelectric elements protrude farther towards a distal end side of the optical fiber than the distal end of the optical fiber protrudes, and
a distance between the distal ends of the first and second pairs of piezoelectric elements and the distal end of the optical fiber is set so that a frequency of a bending resonance vibration, in which one end serves as a fixed end, of distal end portions of the first and second pairs of piezoelectric elements that protrude farther towards the distal end side than the distal end of the optical fiber does is higher than a frequency of an alternating voltage supplied to the first and second pairs of piezoelectric elements for exciting a bending vibration in the optical fiber.

10. An optical fiber scanner according to claim 6, further comprising an electrode provided on an outer circumferential surface of the optical fiber and to which a ground line for the first pair of piezoelectric elements and the second pair of piezoelectric elements is joined.

11. An optical fiber scanner according to claim 10, wherein the ground line is disposed closer to a base end of the optical fiber than the first pair of piezoelectric elements and the second pair of piezoelectric elements are.

* * * * *